(12) United States Patent
Muneaux et al.

(10) Patent No.: US 8,063,061 B2
(45) Date of Patent: Nov. 22, 2011

(54) 6-HETEROARYLPYRIDOINDOLONE DERIVATIVES, THEIR PREPARATION AND THERAPEUTIC USE THEREOF

(75) Inventors: Yvette Muneaux, Les Matelles (FR); Samir Jegham, Montferrier-sur-Lez (FR); Bernard Bourrie, Saint-Gely-du-Fesc (FR); Pierre Casellas, Montpellier (FR); Paola Ciapetti, Altorf (FR); Jean-Marie Deroco, Murviel-les-Montpellier (FR); Camille-Georges Wermuth, Strasbourg (FR)

(73) Assignee: Sanofi-Aventis, Paris (FR)

( * ) Notice: Subject to any disclaimer, the term of this patent is extended or adjusted under 35 U.S.C. 154(b) by 896 days.

(21) Appl. No.: 12/100,079

(22) Filed: Apr. 9, 2008

(65) Prior Publication Data

US 2008/0262020 A1    Oct. 23, 2008

Related U.S. Application Data

(63) Continuation of application No. PCT/FR2006/002330, filed on Oct. 17, 2006.

(30) Foreign Application Priority Data

Oct. 20, 2005 (FR) ..................................... 05 10730

(51) Int. Cl.
*A61K 31/44* (2006.01)
*C07D 471/04* (2006.01)
(52) U.S. Cl. .......................................... 514/292; 546/86
(58) Field of Classification Search .................. 546/86; 514/292
See application file for complete search history.

(56) References Cited

U.S. PATENT DOCUMENTS

| | | | |
|---|---|---|---|
| 4,263,304 | A | 4/1981 | Ishizumi et al. |
| 4,835,160 | A | 5/1989 | Bisagni et al. |
| 5,880,126 | A | 3/1999 | Skuballa et al. |
| 6,503,888 | B1 | 1/2003 | Kaplitt et al. |
| 6,967,203 | B2 | 11/2005 | Bourrie et al. |
| 2002/0156016 | A1 | 10/2002 | Minuk |
| 2004/0122036 | A1 | 6/2004 | Bourrie et al. |
| 2005/0222192 | A1 | 10/2005 | Bourrie et al. |
| 2005/0288318 | A1 | 12/2005 | Bourrie et al. |
| 2007/0129365 | A1 | 6/2007 | Bourrie et al. |
| 2008/0214538 | A1 | 9/2008 | Bourrie et al. |
| 2009/0042924 | A1 | 2/2009 | Bourrie et al. |

FOREIGN PATENT DOCUMENTS

| | | |
|---|---|---|
| FR | 2 003 999 | 11/1969 |
| FR | 2 765 581 | 1/1999 |
| FR | 2 765 582 | 1/1999 |
| FR | 2 846 329 | 4/2004 |
| GB | 1 268 772 | 3/1972 |
| SU | 833971 | 5/1981 |
| WO | WO 99/51597 | 10/1999 |
| WO | WO 01/09129 | 2/2001 |
| WO | WO 02/087574 | 11/2002 |
| WO | WO 02/087575 | 11/2002 |
| WO | WO 2004/037821 | 5/2004 |
| WO | WO 2004/041817 | 5/2004 |
| WO | WO 2005/108398 | 11/2005 |

OTHER PUBLICATIONS

Burger et al, Zum Reaktionsverhalten von Trifluormethyl-Gruppen Synthese von 1,3-Azolen aus Trifluormethyl-substituierten Hetero-1,3-dienen, Chem. Ber., 1982 (115) pp. 2494-2507.
Colomb et al, Nuclear Texture Parameters as Discriminant Factors in Cell Cycle and Drug Sensitivity Studies, Cytometry, 1991 (12) pp. 15-25.
Derocq et al, The endogenous cannabinoid anandamide is a lipid messenger activating cell growth via a cannabinoid receptor-independent pathway in hematopoietic cell lines, FEBS Letters, 1998 (425) pp. 419-425.
Hassner et al, 4,5- and 2,5-additions to oxazoles, Tetrahedron, 1989 (45) 19 pp. 6249-6262.
Kruger et al, 2-Haloethyl 1-Thioglycosides as New Tools in glycoside Syntheses. Part 1: Preparation, Characteristics, General Reactions, Collect. Czech. Chem. Commun., 2004 (69) pp. 1843-1876.
Estenne et al, Derwent Patent Abstract No. 199909 (2003), (Abstract of FR 2 765 582).
Furihata, C., et al., In Vivo Short-Term Assays for Tumor Initiation and Promotion in the Grandular Stomach of Fischer Rats, Mutation Research, (1995), vol. 339, No. 1, pp. 15-35.
Furihata, C., et al., Unscheduled DNA Synthesis in Rat Stomach-Short-Term Assay of Potential Stomach Carcinogens, Banbury Report, (1982), vol. 13, pp. 123-135.
Goldman M.D., et al., Cecil, Textbook of Medicine, 21st edition, vol. 1, published 2000 by W.B. Saunders Co. (PA), pp. 1060-1074.
Golovko, T., et al., A New Approach to the Synthesis of Functionally-Substituted Pyrido 2, 3-D Indoles, Mendeleev Communications, (1995), vol. 6, pp. 226-227.
Goodman & Gilman, Section X. Chemotherapy of Neoplastic Diseases, Goodman & Gilman's the Pharmacological Basis of Therapeutics, 9th Ed., (1996) pp. 1225-1232 and pp. 1269-1271.
Molina, P., et al., Annulation of Pyridine to Indole by a Tandem Aza-Wittig/Electrocyclization Strategy: Synthesis of Pyrido 2, 3-B Indoles, Synthesis, (1989), vol. 11, pp. 878-880.
Nicholson-Guthrie et al, Urine GABA Levels in Ovarian Cancer Patients: elevated GABA in malignancy, Cancer Letters, vol. 162, Issue 1, (2001), pp. 27-30.

*Primary Examiner* — Rebecca Anderson
(74) *Attorney, Agent, or Firm* — Scully, Scott, Murphy & Presser, P.C.

(57) ABSTRACT

The disclosure relates to compounds of formula (I):

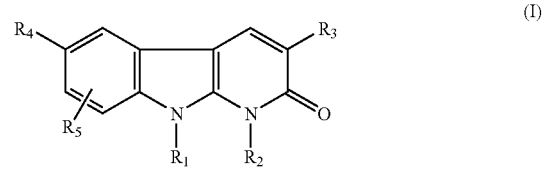

wherein $R_1$, $R_2$, $R_3$, $R_4$, are $R_5$ are as defined in the disclosure; their preparation method, compositions containing the same and therapeutic use thereof.

27 Claims, No Drawings

6-HETEROARYLPYRIDOINDOLONE DERIVATIVES, THEIR PREPARATION AND THERAPEUTIC USE THEREOF

The present invention relates to 6-heteroarylpyridoindolone derivatives, to the preparation thereof and to the therapeutic use thereof.

French patent No. 97 08409 describes compounds of formula:

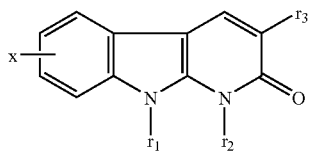

in which:
x is a hydrogen or chlorine atom or a methyl or methoxy group;
$r_1$ is a hydrogen atom or a methyl or ethyl group;
$r_2$ is a methyl or ethyl group; or else
$r_1$ and $r_2$ together form a $(CH_2)_3$ group;
$r_3$ is either a phenyl group optionally substituted with a halogen atom or a methyl or methoxy group, or a thienyl group.

In the description of that patent, it is mentioned that the compounds of formula (A) which have an affinity for $GABA_A$-receptor-associated omega modulatory sites, can be used in the treatment of conditions related to gabaergic transmission disorders associated with $GABA_A$-receptor subtypes, such as anxiety, sleep disorders, epilepsy, etc.

International patent applications WO 2002/087574 and WO 2002/087575 describe the use of the compounds of formula (A) as anticancer agents and the combination thereof with other anticancer agents.

International patent application WO 2004/041817 describes compounds of formula:

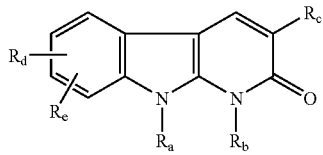

in which $R_a$, $R_b$, $R_c$, $R_d$ and $R_e$ have various values. These compounds exhibit an anticancer activity.

A subject of the present invention is compounds corresponding to formula (I):

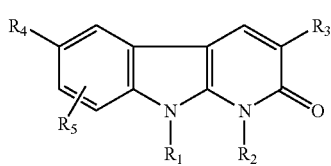

in which:
$R_1$ is a hydrogen atom or a $(C_1$-$C_4)$alkyl, CN, $CF_3$ or $CHF_2$ group;
$R_2$ is a hydrogen atom or a $(C_1$-$C_4)$alkyl group;
$R_3$ is a phenyl which is unsubstituted or substituted one or more times which substituents selected independently from a halogen atom, a $(C_1$-$C_4)$alkyl group and a $(C_1$-$C_4)$alkoxy group;
$R_4$ is a heterocyclic radical selected from:

(A)

(B)

(C)

(D)

(E)

(F)

$R_5$ is a hydrogen atom, a halogen atom, a $(C_1$-$C_4)$alkyl group or a $(C_1$-$C_4)$alkoxy group;
R6 is selected from a hydrogen atom,
a —$SO_2$—$R_{12}$ group,
a $(C_1$-$C_6)$alkyl or $(C_1$-$C_6)$ mono or perfluoro alkyl group,
a —$(CH_2)_n$—NR8R9,
a —$(CH_2)_n$—NH—CO—$(C_1$-$C_4)$alkyl group,
a —$(CH_2)_n$—NH—$SO_2$—$(C_1$-$C_4)$alkyl group,
a —$(CH_2)_n$—NH—$(CH_2)_m$—NR8R9 group,
a —$(CH_2)_n$—NH—$(CH_2)_m$—OR10 group,
a —$(CH_2)_n$—O—$(CH_2)_m$—NR8R9 group,
a —$(CH_2)_n$—O—$(CH_2)_m$—O—$(C_1$-$C_4)$alkyl group,
a —$(CH_2)_n$Hal group,
a —$(C_1$-$C_6)$alkyl-O—R10 group,
a —$CO_2$—$(CH_2)_m$—O—R10 group,
a —$(CH_2)_n$—COOR11 group,
a $(C_1$-$C_6)$alkylcarbonyl-, $(C_1$-$C_6)$ mono or perfluoro alkylcarbonyl-, —CO—NH—R10, or —CO—$(C_1$-$C_6)$alkyl-O—$(C_1$-$C_4)$alkyl group;
R7 is selected from a hydrogen atom,
a $(C_1$-$C_6)$alkyl, or $(C_1$-$C_6)$ mono or perfluoro alkyl group,
a —$(CH_2)_n$—NR8R9 group,
a —$(CH_2)_n$—NH—CO—$(C_1$-$C_4)$alkyl group,
a —$(CH_2)_n$—NH—$SO_2$—$(C_1$-$C_4)$alkyl group, a —(CH$_2$)$_n$—NH—(CH$_2$)$_m$—NR8R9 group,
a —(CH$_2$)$_n$—NH—(CH$_2$)$_m$—OR10 group,
a —(CH$_2$)$_n$—O—(CH$_2$)$_m$—NR8R9 group,
a —(CH$_2$)$_n$—O—(CH$_2$)$_m$—O—(C$_1$-C$_4$) alkyl group,
a —(CH$_2$)$_n$Hal group,
a —(C$_1$-C$_6$)alkyl-O—R10 group,
a —CO$_2$—(CH$_2$)$_m$—O—R10 group,
a —(CH$_2$)$_n$—COOR11 group,
a (C$_1$-C$_6$)alkylcarbonyl-, (C$_1$-C$_6$) mono or perfluoro alkylcarbonyl-, —CO—NH—R10, or —CO—(C$_1$-C$_6$)alkyl-O—(C$_1$-C$_4$)alkyl group;

R$_8$ and R$_9$ are each, independently of one another, a hydrogen atom or a (C$_1$-C$_4$)alkyl group;

or else R$_8$ and R$_9$, together with the nitrogen atom to which they are attached, constitute a heterocyclic radical selected from pyrrolidin-1-yl, piperidin-1-yl, morpholin-4-yl or piperazinyl optionally substituted on its second nitrogen atom;

R$_{10}$ is a hydrogen atom, a (C$_1$-C$_4$)alkyl group, a (C$_1$-C$_4$) alkylcarbonyl-group, a (C$_3$-C$_6$)cycloalkylcarbonyl- group, a (C$_3$-C$_6$)cycloalkyl(C$_1$-C$_4$)alkylcarbonyl- group, a (C$_3$-C$_6$)cycloalkyl group, a (C$_5$-C$_6$) heterocycloalkyl group, a (C$_1$-C$_6$) mono or perfluoro alkyl group, or a (C$_3$-C$_6$)cycloalkyl(C$_1$-C$_4$)alkyl group;

R$_{11}$ is a hydrogen atom or a (C$_1$-C$_6$)alkyl group;

R$_{12}$ is a (C$_1$-C$_6$)alkyl group, a (C$_1$-C$_6$) mono or perfluoro alkyl group, a cycloalkyl group, a cycloalkylalkyl- group, or a (C$_1$-C$_6$)alkyl-O—(C$_1$-C$_4$)alkyl-group;

m is 1 or 2
n is 0, 1 or 2;
Hal is a halogen atom;
in the form of a base or of an addition salt with an acid, and also in the form of a hydrate or of a solvate.

The compounds of formula (I) can contain one or more asymmetrical carbon atoms. They can therefore exist in the form of enantiomers or of diastereoisomers. These enantiomers and diastereoisomers, and also mixtures thereof, including racemic mixtures, are part of the invention.

The compounds of formula (I) can exist in the form of bases or of addition salts with acids. Such addition salts are part of the invention.

The salts are advantageously prepared with pharmaceutically acceptable acids, but the salts of other acids which can be used, for example, for the purification or isolation of the compounds of formula (I) are also part of the invention.

The compounds of formula (I) can also exist in the form of hydrates or of solvates, i.e. in the form of associations or combinations with one or more molecules of water or with a solvent. Such hydrates and solvates are also part of the invention.

In the context of the present invention:
a "halogen atom" is intended to mean: a fluorine, a chlorine, a bromine or an iodine;
a "(C$_1$-C$_6$)alkyl group" is intended to mean: a linear or branched, saturated aliphatic group containing 1 to 6 carbon atoms. By way of example, mention may be made of methyl, ethyl, propyl, isopropyl, butyl, isobutyl, sec-butyl, tert-butyl, pentyl or hexyl groups, and also isomers thereof,
a "(C$_1$-C$_6$)alkoxy group" is intended to mean: an O-alkyl radical where the alkyl group is as defined above;
a "(C$_3$-C$_6$)cycloalkyl group" is intended to mean: a cyclic alkyl group having from 3 to 6 carbon atoms, such as the cyclopropyl, cyclobutyl, cyclopentyl or cyclohexyl group;
a "(C$_5$-C$_6$)heterocycloalkyl group" is in particular the rings: tetrahydropyran, tetrahydrofuran, morpholinyl,
piperidine, pyrrolidine and piperazinyl, itself optionally substituted with an alkyl radical.

Among the compounds of formula (I), which are subjects of the invention, the following are distinguished:
the compounds of formula (IA) in which R$_4$ is a 1,3-thiazole substituted with R$_7$ and the substituents R$_1$ to R$_7$ are as defined for the compounds of formula (I);
the compounds of formula (IB) in which R4 is a 1,3,4-thiadiazole substituted with R7 and the substituents R1 to R7 are as defined for the compounds of formula (I);
the compounds of formula (IC) in which R4 is a 1,3-oxazole substituted with R7 and the substituents R$_1$ to R$_7$ are as defined for the compounds of formula (I);
the compounds of formula (ID) in which R$_4$ is an isoxazole substituted with R$_7$ and the substituents R$_1$ to R$_7$ are as defined for the compounds of formula (I);
the compounds of formula (IE) in which R$_4$ is a 1H-pyrazole
substituted with R$_6$ and R$_7$ and the substituents R$_1$ to R$_7$ are as defined for the compounds of formula (I);
the compounds of formula (IF) in which R$_4$ is a 1,2,3-triazole substituted with R$_6$ and R$_7$ and the substituents R$_1$ to R$_7$ are as defined for the compounds of formula (I).

Among the compounds of formula (I) which are subjects of the invention, mention may be made of the preferred compounds which are defined as follows:
R$_1$ is a hydrogen atom, a methyl or CHF$_2$;
R$_2$ is a methyl;
R$_3$ is a 2,4-dichlorophenyl; a 4F-phenyl or a 4Cl-phenyl;
R$_4$ is a heterocyclic radical selected from:

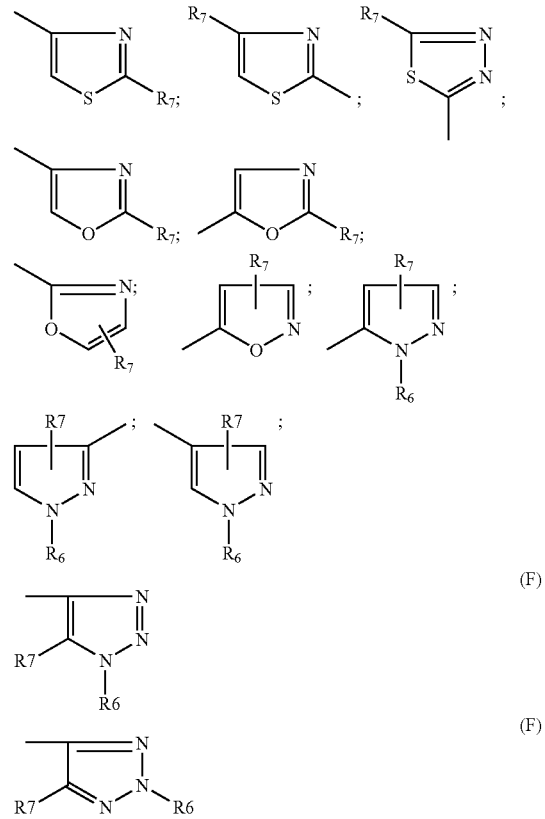

-continued

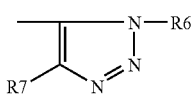
(F)

$R_5$ is a hydrogen atom;
$R_6$ is selected from a hydrogen atom,
an —$SO_2$—$R_{12}$ group,
a ($C_1$-$C_6$)alkyl or ($C_1$-$C_6$) mono or perfluoro alkyl group,
a —$(CH_2)_n$—NR8R9 group,
a —$(CH_2)_n$—NH—CO—($C_1$-$C_4$)alkyl group,
a —$(CH_2)_n$—NH—$SO_2$—($C_1$-$C_4$)alkyl group,
a —$(CH_2)_n$—NH—$(CH_2)_m$—NR8R9 group,
a —$(CH_2)_n$—O—$(CH_2)_m$—NR8R9 group,
a —$(CH_2)_n$—O—$(CH_2)_m$—O—($C_1$-$C_4$) alkyl group,
a —$(CH_2)_n$Hal group,
a —($C_1$-$C_6$)alkyl-O—R10 group,
a —$CO_2$—$(CH_2)_m$—O—R10 group,
a —$(CH_2)_n$—COOR11 group,
a ($C_1$-$C_6$)alkylcarbonyl-, ($C_1$-$C_6$) mono or perfluoro alkylcarbonyl-, or CO—NH—R10 group;
R7 is selected from a hydrogen atom,
a ($C_1$-$C_6$)alkyl or ($C_1$-$C_6$) mono or perfluoro alkyl group,
a —$(CH_2)_n$—NR8R9 group,
a —$(CH_2)_n$—NH—CO—($C_1$-$C_4$)alkyl group,
a —$(CH_2)_n$—NH—$SO_2$—($C_1$-$C_4$)alkyl group,
a —$(CH_2)_n$—NH—$(CH_2)_m$—NR8R9 group,
a —$(CH_2)_n$—O—$(CH_2)_m$—NR8R9 group,
a —$(CH_2)_n$—O—$(CH_2)_m$—O—($C_1$-$C_4$) alkyl group,
a —$(CH_2)_n$Hal group,
a —($C_1$-$C_6$)alkyl-O—R10 group,
a —$CO_2$—$(CH_2)_m$—O—R10 group,
a —$(CH_2)_n$—COOR11 group,
a ($C_1$-$C_6$)alkylcarbonyl-, ($C_1$-$C_6$) mono or perfluoro alkylcarbonyl-, or CO—NH—$R_{10}$ group;
the radicals $R_8$, $R_9$, $R_{10}$, $R_{11}$, and n and m having the definitions above, said products of formula (I) being in the form of a base or of an addition salt with an acid, and also in the form of a hydrate or of a solvate.

By way of non-limiting examples, mention may be made of the following radicals when R6 and/or R7 are:
the —$(CH_2)_n$—NR8R9 group, then this group can, for example, be $CH_2$—$NH_2$, $CH_2$—NHalk, $CH_2$—N(alk)$_2$ or $CH_2$-heterocycloalkyl;
the —$(CH_2)_n$—NH—$(CH_2)_m$—NR8R9 group, then this group can, for example, be —$(CH_2)_n$—NH—$(CH_2)_m$-heterocycloalkyl;
the —$(CH_2)_n$—O—$(CH_2)_m$—NR8R9 group, then this group can, for example, be —$(CH_2)_n$—O—$(CH_2)_m$-heterocycloalkyl;
the —$(CH_2)_n$Hal group, then this group can, for example, be $CH_2$—Cl,
the —($C_1$-$C_6$)alkyl-O—R10 group, then this group can, for example, be $CH_2$—OH, $CH_2$—O—$CH_3$ or $CH_2$—O—$C_2H_5$;
the CO—NH—R10 group, then this group can, for example, be —CO—NH—($C_1$-$C_4$)alkyl.

It may be noted that, when $R_6$ or $R_7$ is a —$(CH_2)_n$—NR8R9 group, a —$(CH_2)_n$—NH—$(CH_2)_m$—NR8R9, or a —$(CH_2)_n$—O—$(CH_2)_m$—NR8R9 group, in these groups, NR8R9 is in particular a heterocyclic radical selected from pyrrolidin-1-yl, piperidin-1-yl, morpholin-4-yl or piperazinyl optionally substituted on its second nitrogen atom with an alkyl radical.

A subject of the present invention is thus compounds corresponding to the formula:

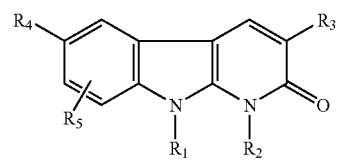
(I)

in which:
$R_1$ is a hydrogen atom or a ($C_1$-$C_4$) alkyl group;
$R_2$ is a hydrogen atom or a ($C_1$-$C_4$) alkyl group;
$R_3$ is a phenyl which is unsubstituted or substituted one or more times with substituents selected independently from a halogen atom, a ($C_1$-$C_4$) alkyl group and a ($C_1$-$C_4$) alkoxy group;
$R_4$ is a heterocyclic radical selected from:

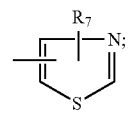
(A)

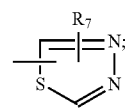
(B)

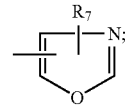
(C)

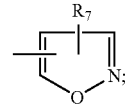
(D)

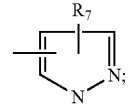
(E)

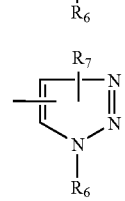
(F)

$R_5$ is a hydrogen atom, a halogen atom, a ($C_1$-$C_4$) alkyl group or a ($C_1$-$C_4$) alkoxy group;
$R_6$ is a hydrogen atom or a ($C_1$-$C_4$) alkyl group;
$R_7$ is a hydrogen atom, a ($C_1$-$C_4$) alkyl group, a —$(CH_2)_n$—NR8R9 group, a —$(CH_2)_n$Hal group, a —$CH_2$—O—$R_{10}$ group or a —$(CH_2)_n$—COOR$_{11}$ group;
$R_8$ and $R_9$ are each, independently of one another, a hydrogen atom or a ($C_1$-$C_4$) alkyl group;
or else $R_8$ and $R_9$, together with the nitrogen atom to which they are attached, constitute a heterocyclic radical selected from pyrrolidin-1-yl, piperidin-1-yl or morpholin-4-yl;

$R_{10}$ is a hydrogen atom, a ($C_1$-$C_4$) alkyl group, a ($C_1$-$C_4$) alkylcarbonyl group or a ($C_3$-$C_6$) cycloalkylcarbonyl group;

$R_{11}$ is a hydrogen atom or a ($C_1$-$C_4$) alkyl group;

n is 0 or 1;

Hal is a halogen atom;

in the form of a base or of an addition salt with an acid, and also in the form of a hydrate or of a solvate.

Among the compounds of formula (I) which are subjects of the invention, mention may be made of the preferred compounds which are defined as follows:

$R_1$ is a hydrogen atom or a methyl;

$R_2$ is a methyl;

$R_3$ is a 2,4-dichlorophenyl;

$R_4$ is a heterocyclic radical selected from:

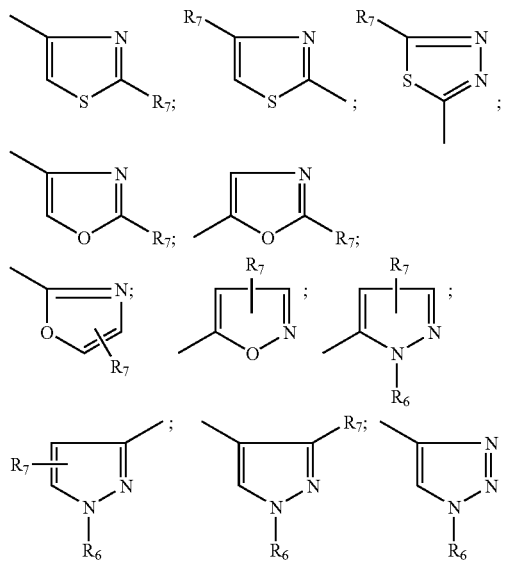

$R_5$ is a hydrogen atom;

$R_6$ is a hydrogen atom, a methyl or an ethyl;

$R_7$ is a hydrogen atom, a methyl, an amino, a methylamino, an aminomethyl, a (dimethylamino)methyl, a pyrrolidin-1-ylmethyl, a chloromethyl, a hydroxymethyl, an ethoxymethyl, a [(2,2-dimethylpropanoyl)oxy]methyl, a [(cyclopropyl-carbonyl)oxy]methyl, a methoxycarbonyl, a 2-methoxy-2-oxoethyl or a carboxymethyl;

in the form of a base or of an addition salt with an acid, and also in the form of a hydrate or of a solvate.

Among the compounds of the latter group, mention may be made of the compounds of formula (I) for which:

$R_1$ is a hydrogen atom or a methyl;

$R_2$ is a methyl;

$R_3$ is a 2,4-dichlorophenyl;

$R_4$ is:

a 2-methyl-1,3-thiazol-4-yl, a 2-amino-1,3-thiazol-4-yl, a 2-(methylamino)-1,3-thiazol-4-yl, a 2-(hydroxymethyl)-1,3-thiazol-4-yl, a 2-(ethoxymethyl)-1,3-thiazol-4-yl, a 2-[[(2,2-dimethylpropanoyl)oxy]methyl]-1,3-thiazol-4-yl, or a 2-[(cyclopropylcarbonyl)oxy]methyl;

a 1,3-thiazol-2-yl, a 4-methyl-1,3-thiazol-2-yl, a 4-amino-1,3-thiazol-2-yl, a 4-(aminomethyl)-1,3-thiazol-2-yl, a 4-[(dimethylamino)methyl]-1,3-thiazol-2-yl, a 4-(pyrrolidin-1-ylmethyl)-1,3-thiazol-2-yl, a 4-(chloromethyl)-1,3-thiazol-2-yl, a 4-(2-methoxy-2-oxoethyl)-1,3-thiazol-2-yl, or a 4-(carboxymethyl)-1,3-thiazol-2-yl;

a 1,3-oxazol-4-yl, a 2-methyl-1,3-oxazol-4-yl, a 2-amino-1,3-oxazol-4-yl, a 2-(hydroxymethyl)-1,3-oxazol-4-yl, a 2-(ethoxymethyl)-1,3-oxazol-4-yl, or a 2-[[(2,2-dimethylpropanoyl)oxy]methyl]-1,3-oxazol-4-yl;

a 1,3-oxazol-5-yl, a 2-methyl-1,3-oxazol-5-yl, or a 2-(ethoxymethyl)-1,3-oxazol-5-yl;

a 1,3-oxazol-2-yl, a 4-methyl-1,3-oxazol-2-yl, or a 5-methyl-1,3-oxazol-2-yl;

an isoxazol-5-yl, a 4-methylisoxazol-5-yl, or a 3-(methoxycarbonyl)isoxazol-5-yl;

a 1H-pyrazol-5-yl, a 1-ethyl-1H-pyrazol-5-yl, a 3-(methoxycarbonyl)-1H-pyrazol-5-yl, a 3-methyl-1H-pyrazol-5-yl, or a 3-amino-1H-pyrazol-5-yl;

a 1-methyl-1H-pyrazol-3-yl, or a 1-ethyl-1H-pyrazol-3-yl;

a 3-amino-1H-pyrazol-4-yl;

a 5-amino-1,3,4-thiadiazol-2-yl;

a 1H-1,2,3-triazol-4-yl;

$R_5$ is a hydrogen atom; in the form of a base or of an addition salt with an acid, and also in the form of a hydrate or of a solvate.

Among the compounds of formula (I), which are subjects of the invention, mention may in particular be made of the following compounds:

6-(2-amino-1,3-thiazol-4-yl)-3-(2,4-dichlorophenyl)-1-methyl-1,9-dihydro-2H-pyrido[2,3-b]indol-2-one;

3-(2,4-dichlorophenyl)-6-[2-(hydroxymethyl)-1,3-thiazol-4-yl]-1-methyl-1,9-dihydro-2H-pyrido[2,3-b]indol-2-one;

3-(2,4-dichlorophenyl)-1,9-dimethyl-6-(2-methyl-1,3-thiazol-4-yl)-1,9-dihydro-2H-pyrido[2,3-b]indol-2-one;

[4-[3-(2,4-dichlorophenyl)-1,9-dimethyl-2-oxo-2,9-dihydro-1H-pyrido[2,3-b]indol-6-yl]-1,3-thiazol-2-yl]methyl pivalate;

3-(2,4-dichlorophenyl)-6-[2-(ethoxymethyl)-1,3-thiazol-4-yl]-1,9-dimethyl-1,9-dihydro-2H-pyrido[2,3-b]indol-2-one;

3-(2,4-dichlorophenyl)-1,9-dimethyl-6-(2-methyl-1,3-oxazol-4-yl)-1,9-dihydro-2H-pyrido[2,3-b]indol-2-one;

3-(2,4-dichlorophenyl)-1,9-dimethyl-6-(2-methyl-1,3-oxazol-5-yl)-1,9-dihydro-2H-pyrido[2,3-b]indol-2-one;

6-(3-amino-1H-pyrazol-5-yl)-3-(2,4-dichlorophenyl)-1,9-dimethyl-1,9-dihydro-2H-pyrido[2,3-b]indol-2-one;

6-[4-(aminomethyl)-1,3-thiazol-2-yl]-3-(2,4-dichlorophenyl)-1,9-dimethyl-1,9-dihydro-2H-pyrido[2,3-b]indol-2-one;

6-(3-amino-1H-pyrazol-4-yl)-3-(2,4-dichlorophenyl)-1,9-dimethyl-1,9-dihydro-2H-pyrido[2,3-b]indol-2-one;

3-(2,4-dichlorophenyl)-1,9-dimethyl-6-(1H-pyrazol-5-yl)-1,9-dihydro-2H-pyrido[2,3-b]indol-2-one;

in the form of a base or of an addition salt with an acid, and also in the form of a hydrate or of a solvate.

Among the compounds of formula (I), which are subjects of the invention, mention may in particular be made of the following compounds:

3-(2,4-dichlorophenyl)-6-(1-methoxymethyl-1H-pyrazol-3-yl)-1,9-dimethyl-1,9-dihydropyrido[2,3-b]indol-2-one;

3-(4-bromophenyl)-6-(1-ethyl-1H-pyrazol-3-yl)-1,9-dimethyl-1,9-dihydropyrido[2,3-b]indol-2-one;

6-(2-aminothiazol-5-yl)-3-(2-chloro-4-fluorophenyl)-1,9-dimethyl-1,9-dihydropyrido[2,3-b]indol-2-one;

3-(2,4-dichlorophenyl)-6-(2-methoxymethylthiazol-4-yl)-1,9-dimethyl-1,9-dihydropyrido[2,3-b]indol-2-one;

3-(2,4-dichlorophenyl)-6-[1-(2,2-dimethylpropionyl)-4-methyl-1H-pyrazol-3-yl]-1,9-dimethyl-1,9-dihydropyrido[2,3-b]indol-2-one;

3-(2,4-dichlorophenyl)-6-(5-ethoxymethyl-1-methyl-1H-pyrazol-3-yl)-1,9-dimethyl-1,9-dihydropyrido[2,3-b]indol-2-one;

3-(4-fluorophenyl)-6-(1-methoxymethyl-1H-pyrazol-3-yl)-1,9-dimethyl-1,9-dihydropyrido[2,3-b]indol-2-one;

3-(4-fluorophenyl)-6-(1-methoxymethyl-4-methyl-1H-pyrazol-3-yl)-1,9-dimethyl-1,9-dihydropyrido[2,3-b]indol-2-one;

3-(4-chlorophenyl)-6-(2-ethoxymethylthiazol-4-yl)-1,9-dimethyl-1,9-dihydropyrido[2,3-b]indol-2-one;

3-(2,4-dichlorophenyl)-6-[1-(2,2-dimethylpropionyl)-1H-pyrazol-3-yl]-1,9-dimethyl-1,9-dihydropyrido[2,3-b]indol-2-one;

3-(2,4-dichlorophenyl)-6-(1-methoxymethyl-1H-[1,2,3]triazol-4-yl)-1,9-dimethyl-1,9-dihydropyrido[2,3-b]indol-2-one;

in the form of a base or of an addition salt with an acid, and also in the form of a hydrate or of a solvate.

In the subsequent text, the term "protective group Gp or G'p" is intended to mean a group which makes it possible, firstly, to protect a reactive function such as a hydroxyl or an amine during synthesis and, secondly, to regenerate the intact reactive function at the end of synthesis. Examples of protective groups and also of methods of protection and deprotection are given in "Protective Groups in Organic Synthesis", Green et al., 2nd Edition (John Wiley & Sons, Inc., New York, 1991).

In the subsequent text, the term "leaving group" is intended to mean a group which can be readily cleaved from a molecule by heterolytic bond cleavage, with the departure of a pair of electrons. This group can thus be readily replaced with another group during a substitution reaction, for example. Such leaving groups are, for example, halogens or an activated hydroxyl group such as a methanesulphonate, benzenesulphonate, p-toluenesulphonate, triflate, acetate, etc. Examples of leaving groups and also of references for the preparation thereof are given in "Advanced Organic Chemistry", J. March, 3rd Edition, Wiley Interscience, p. 310-316, 1985.

In accordance with the invention, the compounds of formula (I) can be prepared according to processes well known to those skilled in the art, such as those described hereinafter.

In accordance with the invention, the compounds of formula (IA) in which

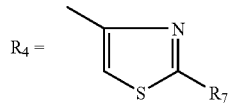

can be prepared according to a process which is characterized in that:
a compound of formula:

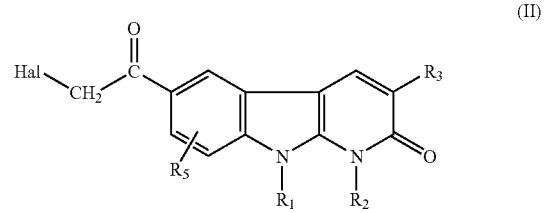

in which $R_1$, $R_2$, $R_3$ and $R_5$ are as defined for a compound of formula (I) and Hal is a halogen atom, is reacted with a compound of formula:

in which $R_7$ is as defined for a compound of formula (I).

The reaction is carried out in a solvent such as N-methylpyrrolidin-2-one, methanol or ethanol, at a temperature of between ambient temperature and the reflux temperature of the solvent.

In accordance with the invention, the compounds of formula (IA) in which

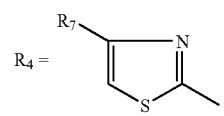

can be prepared according to a process which is characterized in that:
a compound of formula

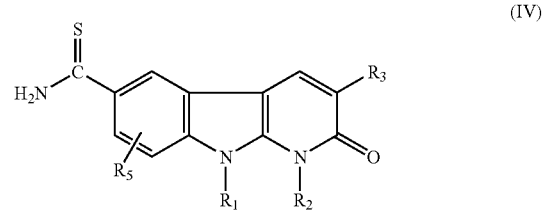

in which $R_1$, $R_2$, $R_3$ and $R_5$ are as defined for a compound of formula (I), is reacted with a compound of formula:

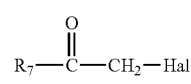

in which $R_7$ is as defined for a compound of formula (I) and Hal is a halogen atom.

The reaction is carried out without solvent or in a solvent such as acetonitrile or 1,4-dioxane, at a temperature of between ambient temperature and the reflux temperature of the solvent.

In particular, a compound of formula (IA) in which:

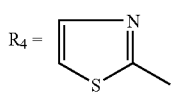

can be prepared by reaction of a compound of formula:

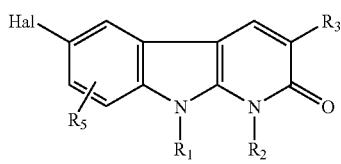

in which $R_1$, $R_2$, $R_3$ and $R_5$ are as defined for a compound of formula (I) and Hal is a halogen atom, with 2-(tributylstannyl)-1,3-thiazole, in the presence of $Cu_2O$, of palladium(II) acetate and of 1,3-bis(diphenylphosphino)propane, in a solvent such as N-methylpyrrolidon-2-one at a temperature of between ambient temperature and 100° C.

In accordance with the invention, the compounds of formula (IB) in which

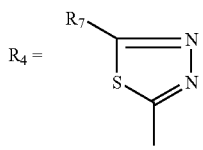

can be prepared according to a process which is characterized in that:

a compound of formula:

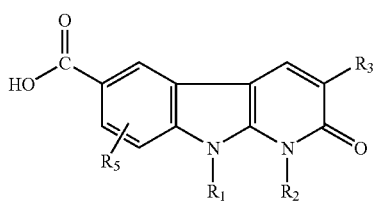

in which $R_1$, $R_2$, $R_3$ and $R_5$ are as defined for a compound of formula (I), is reacted with a compound of formula:

in which $R_7$ is as defined for a compound of formula (I).

The reaction is carried out in the presence of $POCl_3$, at a temperature of between ambient temperature and the reflux temperature of the reaction mixture.

In accordance with the invention, the compounds of formula (IC) in which

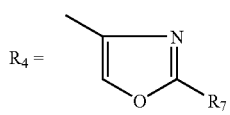

can be prepared according to a process which is characterized in that:

a compound of formula:

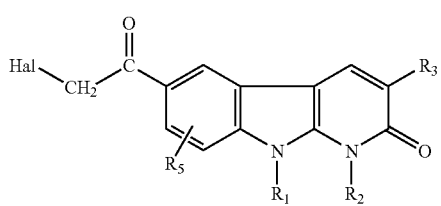

in which $R_1$, $R_2$, $R_3$ and $R_5$ are as defined for a compound of formula (I), and Hal is a halogen atom, is reacted with a compound of formula:

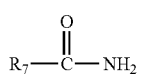

in which $R_7$ is as defined for a compound of formula (I).

The reaction is carried out without solvent or in a solvent such as N-methylpyrrolidin-2-one, methanol, or ethanol, at a temperature of between ambient temperature and 160° C.

In accordance with the invention, the compounds of formula (IC) in which

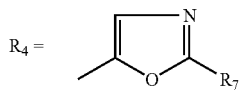

can be prepared according to a process which is characterized in that:

A) a compound of formula:

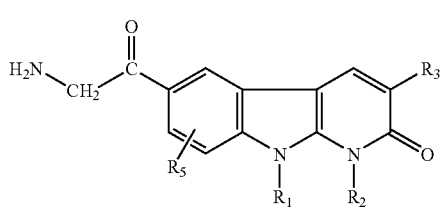

in which $R_1$, $R_2$, $R_3$ and $R_5$ are as defined for a compound of formula (I), is reacted with a functional derivative of an acid of formula:

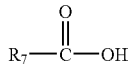
(XI)

in which $R_7$ is as defined for a compound of formula (I), so as to obtain a compound of formula:

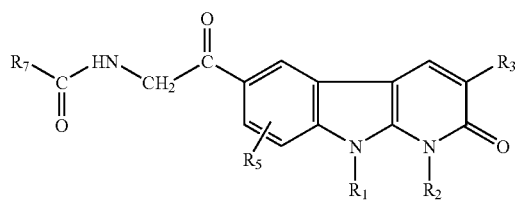
(XII)

B) The compound of formula (XII) thus obtained is cyclized through the action of an acid.

In step A), when a compound of formula (X) is treated with the acid of formula (XI) itself, the process is carried out in the presence of a coupling agent used in peptide chemistry, such as 1,3-dicyclohexylcarbodiimide or benzotriazol-1-yloxytris (dimethylamino)phosphonium hexafluorophosphate or benzotriazol-1-yloxytris(pyrrolidino)phosphonium hexafluorophosphate or 2-(1H-benzotriazol-1-yl)-1,1,3,3-tetramethyluronium tetrafluoroborate, in the presence of a base such as triethylamine, N,N-diisopropylethylamine or 4-dimethylaminopyridine, in a solvent such as dichloromethane, dichloroethane, N-N-dimethylformamide or tetrahydrofuran, at a temperature of between −10° C. and the reflux temperature of the solvent.

As functional derivative of the acid (XI), use may be made of the acid chloride, the anhydride, a mixed anhydride, a $C_1$-$C_4$ alkyl ester in which the alkyl is linear or branched, or an activated ester, for example p-nitrophenyl ester.

Thus, in the process according to the invention, it is also possible to react the acid chloride obtained by reaction of thionyl chloride or of oxalyl chloride with the acid of formula (XI), with the compound of formula (X), in a solvent, such as a chlorinated solvent (dichloromethane, dichloroethane, or chloroform, for example), an ether (tetrahydrofuran or dioxane, for example), or an amide (N,N-dimethylformamide, for example) under an inert atmosphere, at a temperature of between 0° C. and ambient temperature, in the presence of a tertiary amine such as triethylamine, N-methylmorpholine or pyridine.

A variant consists in preparing the mixed anhydride of the acid of formula (XI) by reaction of ethyl chloroformate with the acid of formula (XI), in the presence of a base such as triethylamine, and in reacting it with the compound of formula (X), in a solvent such as dichloromethane, under an inert atmosphere, at ambient temperature, in the presence of a base such as triethylamine.

In step B), the cyclization reaction is carried out through the action of an acid such as sulphuric acid, at a temperature of between 0° C. and ambient temperature.

In particular, a compound of formula (IC) in which:

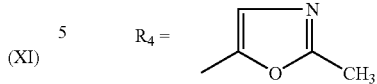

can be prepared by reaction of a compound of formula (X) with triethyl orthoacetate, in the presence of a catalytic amount of an acid such as 4-toluene sulphonic acid, at a temperature of between ambient temperature and 150° C.

In particular also, a compound of formula (IC) in which

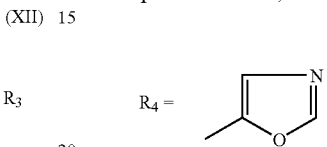

can be prepared by reaction of a compound of formula:

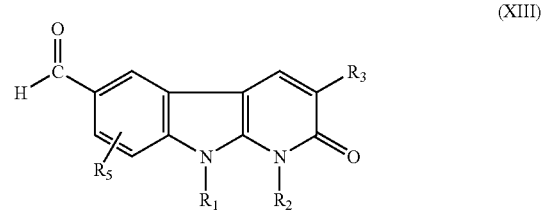
(XIII)

in which $R_1$, $R_2$, $R_3$ and $R_5$ are as defined for a compound of formula (I), with 1-[(isocyanomethyl)sulphonyl]-4-methylbenzene, in the presence of a base such as potassium carbonate, in a solvent such as methanol and at a temperature of between ambient temperature and the reflux temperature of the solvent.

In accordance with the invention, the compounds of formula (IC) in which

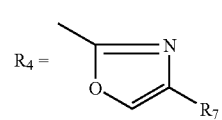

can be prepared according to a process which is characterized in that:
a compound of formula:

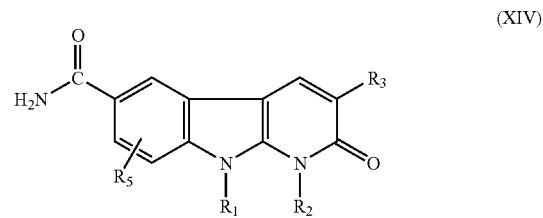
(XIV)

in which $R_1$, $R_2$, $R_3$, and $R_5$ are as defined for a compound of formula (I), is reacted with a compound of formula:

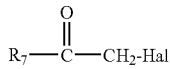 (V)

in which $R_7$ is as defined for a compound of formula (I) and Hal is a halogen atom. The reaction is carried out according to the operating conditions described in Chem. Ber., 1982, 115 (7), 2494-2507.

In accordance with the invention, the compounds of formula (IC) in which

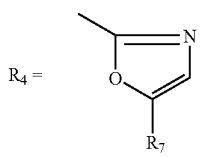

can be prepared according to a process which is characterized in that:

a compound of formula (XIV) is reacted with a compound of formula (V) according to the operating conditions described in Tetrahedron, 1989, 45(19), 6249-6262.

In particular, a compound of formula (IC) in which:

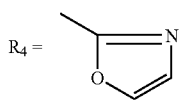

can be prepared by reaction of a compound of formula (XIV) with 1,3-dioxol-2-one, in the presence of an acid such as $H_3PO_4$, at a temperature of between ambient temperature and 170° C.

In particular also, a compound of formula (IC) in which

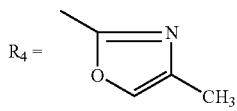

can be prepared by reaction of a compound of formula:

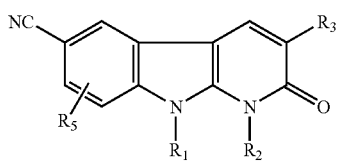 (XV)

in which $R_1$, $R_2$, $R_3$ and $R_5$ are as defined for a compound of formula (I), with propargyl alcohol, in the presence of an acid such as sulphuric acid, at a temperature of between −20° C. and ambient temperature.

In particular, finally, a compound of formula (IC) in which

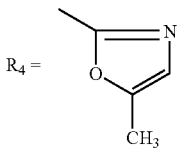

can be prepared by cyclization of a compound of formula:

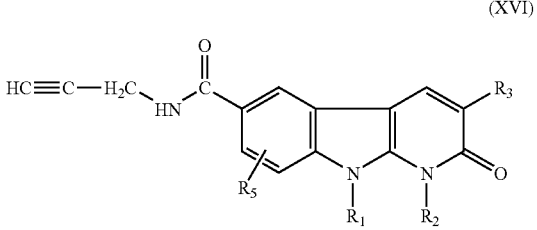 (XVI)

in which $R_1$, $R_2$, $R_3$ and $R_5$ are as defined for a compound of formula (I). The cyclization reaction is carried out in the presence of mercury acetate and of an acid such as acetic acid, at a temperature of between ambient temperature and 120° C.

In accordance with the invention, the compounds of formula (ID) in which

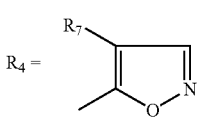

can be prepared according to a process which is characterized in that:
a compound of formula:

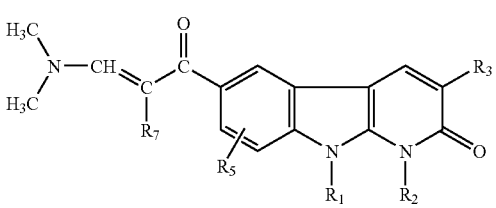 (XVII)

in which $R_1$, $R_2$, $R_3$, $R_5$ and $R_7$ are as defined for a compound of formula (I), is reacted with hydroxylamine. The reaction is carried out in a solvent such as methanol and at a temperature of between ambient temperature and the reflux temperature of the solvent.

In accordance with the invention, the compounds of formula (ID) in which

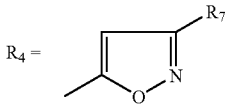

can be prepared according to a process which is characterized in that:

a compound of formula:

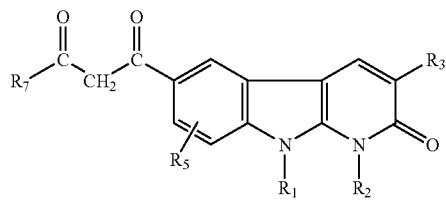
(XVIII)

in which $R_1$, $R_2$, $R_3$, $R_5$ and $R_7$ are as defined for a compound of formula (I), is reacted with hydroxylamine. The reaction is carried out in a solvent such as methanol and at a temperature of between ambient temperature and the reflux temperature of the solvent.

In accordance with the invention, the compounds of formula (ID) in which

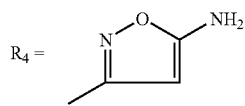

can be prepared according to a process which is characterized in that a compound of formula (XX):

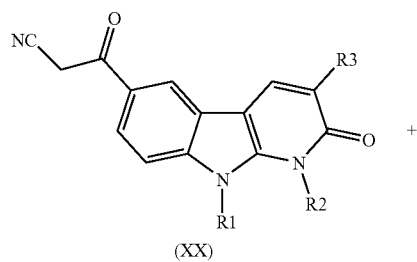

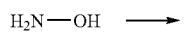

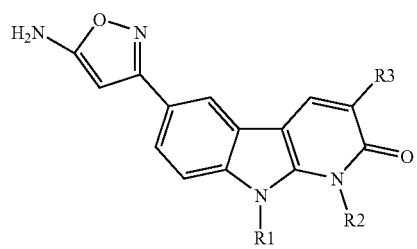

in which $R_1$, $R_2$ and $R_3$ are as defined for a compound of formula (I), is reacted with hydroxylamine. The reaction is carried out in a solvent such as methanol and at a temperature of between ambient temperature and the reflux temperature of the solvent.

In accordance with the invention, a compound of formula (IE) in which

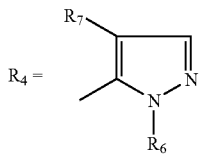

can be prepared according to a process which is characterized in that:

a compound of formula:

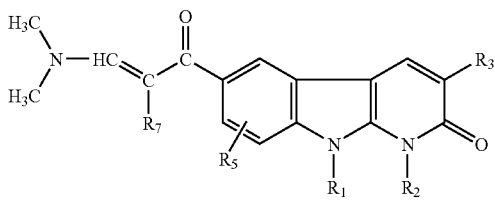
(XVII)

in which $R_1$, $R_2$, $R_3$, $R_5$ and $R_7$ are as defined for a compound of formula (I), is reacted with a compound of formula:

$$NH_2-NH-R_6 \qquad (XIX)$$

in which $R_6$ is as defined for a compound of formula (I). The reaction is carried out in a solvent such as methanol and at a temperature of between ambient temperature and the reflux temperature of the solvent.

In accordance with the invention, a compound of formula (IE) in which

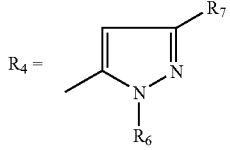

can be prepared according to a process which is characterized in that:

a compound of formula:

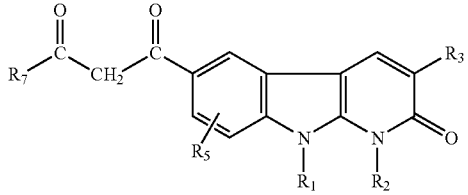
(XVIII)

in which $R_1$, $R_2$, $R_3$, $R_5$ and $R_7$ are as defined for a compound of formula (I), is reacted with a hydrazine of formula (XIX). The reaction is carried out in a solvent such as methanol or ethanol and at a temperature of between ambient temperature and the reflux temperature of the solvent.

In particular, a compound of formula (IE) in which

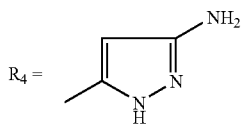

can be prepared by reaction of a compound of formula:

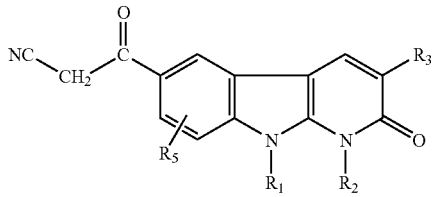

in which $R_1$, $R_2$, $R_3$, and $R_5$ as are as defined for a compound of formula (I), with hydrazine. The reaction is carried out in a solvent such as ethanol and at a temperature of between ambient temperature and the reflux temperature of the solvent.

In particular, a compound of formula (IE) in which

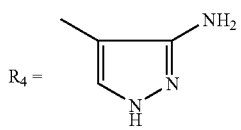

can be prepared by reaction of a compound of formula:

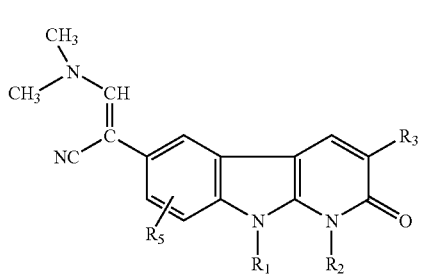

in which $R_1$, $R_2$, $R_3$, and $R_5$ are as defined for a compound of formula (I), with hydrazine. The reaction is carried out in the presence of an acid such as acetic acid, in a solvent such as MeOH and at a temperature of between ambient temperature and the reflux temperature of the solvent.

In accordance with the invention, a compound of formula (IF) in which

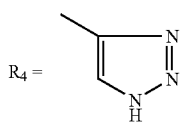

can be prepared according to a process which is characterized in that:

a compound of formula:

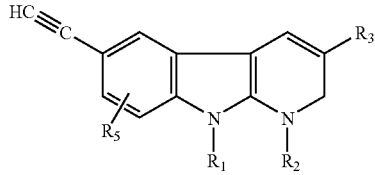

in which $R_1$, $R_2$, $R_3$ and $R_5$ are as defined for a compound of formula (I), is reacted with sodium azide. The reaction is carried out in the presence of ammonium chloride, in a solvent such as N,N-dimethylformamide, at a temperature of between ambient temperature and 200° C.

A compound of formula (I) in which $R_1$ and/or $R_2$ are/is a $(C_1-C_4)$alkyl group can also be prepared by reaction of a compound of formula (I) in which $R_1$ and/or $R_2$ are/is a hydrogen atom, with a $(C_1-C_4)$alkyl halide, in the presence of a base such as sodium hydride, in a solvent such as N,N-dimethylformamide and at a temperature of between ambient temperature and the reflux temperature of the solvent.

The compounds of formula (I) in which $R_4$ is a heterocycle substituted with $R_7=-(CH_2)_n-NR_8R_9$ can also be prepared by reaction of a corresponding compound of formula (I) in which $R_7=-(CH_2)_n$-Hal, with an amine of formula $HNR_8R_9$, in the presence of a base such as an alkaline metal carbonate, in a solvent such as dimethyl sulphoxide or N,N-dimethylformamide and at a temperature of between ambient temperature and the reflux temperature of the solvent.

The compounds of formula (I) in which $R_4$ is a heterocycle substituted with $R_7=-CH_2-O-R_{10}$, with $R_{10}=(C_1-C_4)$ alkyl, can also be prepared by reaction of a corresponding compound of formula (I) in which $R_7=-CH_2-OH$, with a $(C_1-C_4)$alkyl halide, in the presence of a base such as sodium hydride, in a solvent such as N,N-dimethylformamide and at a temperature of between ambient temperature and the reflux temperature of the solvent.

The compounds of formula (I) in which $R_4$ is a heterocycle substituted with $R_7=-CH_2-O-R_{10}$, with $R_{10}=(C_1-C_4)$ alkylcarbonyl or $(C_3-C_6)$cycloalkylcarbonyl, can also be prepared by reaction of a corresponding compound of formula (I) in which $R_7=-CH_2-OH$ with a $(C_1-C_4)$alkylcarbonyl halide or $(C_3-C_6)$cycloalkylcarbonyl halide, in the presence of a base such as pyridine, at a temperature of between 0° C. and ambient temperature.

The compounds of formula (I) in which $R_4$ is a heterocycle substituted with $R_6=(C_1-C_4)$alkyl can also be prepared by reaction of a corresponding compound of formula (I) in which $R_6=H$, with a $(C_1-C_4)$alkyl halide, in the presence of a base such as sodium hydride, in a solvent such as N,N-dimethylformamide and at a temperature of between 0° C. and the reflux temperature of the solvent.

The compounds of formula (I) thus obtained can be subsequently separated from the reaction medium and purified according to conventional methods, for example by crystallization or chromatography.

The compounds of formula (I) thus obtained are isolated in the form of a free base or of a salt, according to conventional techniques.

The compounds of formula (II) are prepared by reaction of a compound of formula:

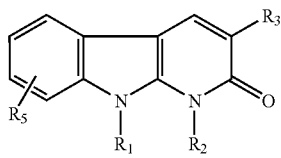
(XXIII)

in which $R_1$, $R_2$, $R_3$ and $R_5$ are as defined for a compound of formula (I), with the compound of formula:

(XXIV)

in which Hal is a halogen atom, according to the conditions of the Friedels and Craft reaction. Thus, the reaction is carried out in the presence of a Lewis acid such as aluminium chloride, in a solvent such as dichloromethane and at a temperature of between 0° C. and ambient temperature.

The compounds of formula (III) are known or are prepared according to known methods.

The compounds of formula (IV) are prepared by reaction of a compound of formula:

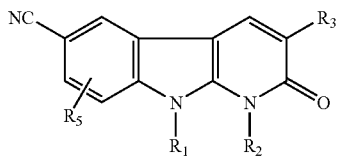
(XV)

in which $R_1$, $R_2$, $R_3$, and $R_5$ are as defined for a compound of formula (I), with O,O'-diethyldithiophosphate, in a mixture of N-methylpyrrolidin-2-one and water, at a temperature of between ambient temperature and 100° C.

The compounds of formula (V) are known or are prepared according to known methods.

The compounds of formula (VI) are known and are prepared according to the methods described in WO 2004/041817.

The compounds of formula (VII) are prepared by conventional hydrolysis of the compounds of formula:

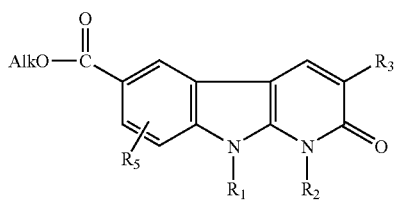
(XXV)

in which $R_1$, $R_2$, $R_3$, and $R_5$ are as defined for a compound of formula (I), and Alk is a $(C_1-C_2)$alkyl. The reaction is carried out through the action of a base such as potassium hydroxide, in a solvent such as methanol, or ethanol, as a mixture with water, at a temperature of between ambient temperature and the reflux temperature of the solvent.

The compounds of formulae (VIII) and (IX) are known or are prepared according to known methods.

The compounds of formula (X) are prepared by reaction of the compounds of formula (II) with hexamethylenetetramine, in a solvent such as chloroform, at ambient temperature, followed by acid hydrolysis.

The compounds of formula (XI) are known or are prepared according to known methods.

The compounds of formula (XIII) are prepared by reaction of the compounds of formula (XV) with $NaH_2PO_2$, in the presence of a base such as pyridine, of an acid such as acetic acid and of a catalyst such as Raney® nickel at a temperature of between ambient temperature and the reflux temperature of the reaction medium.

The compounds of formula (XIV) are prepared by reaction of the compounds of formula (VI) with 1,1,1,3,3,3-hexamethyldisilazane, in the presence of $PdCl_2(PPh_3)_2$, in a solvent such as N,N-dimethylformamide, at a temperature of between ambient temperature and the reflux temperature of the solvent.

The compounds of formula (XV) are known and are prepared according to the methods described in WO 2004/041817.

The compounds of formula (XVI) are prepared by reaction of the compounds of formula (VII) with propargylamine according to the peptide coupling methods previously described.

The compounds of formula (XVII) are prepared by reaction of the compounds of formula:

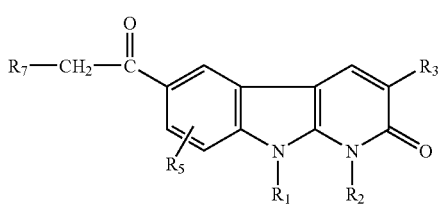
(XXVI)

in which $R_1$, $R_2$, $R_3$, $R_5$ and $R_7$ are as defined for a compound of formula (I), with Bredereck's reagent (tert-butoxybis(dimethylamino)methane) under hot conditions.

The compounds of formula (XVIII) are prepared by reaction of the compounds of formula (XXVI) in which $R_7$=H, with a compound of formula:

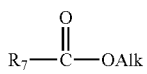
(XXVII)

in which $R_7$ is as defined for a compound of formula (I), and Alk is a $(C_1-C_4)$alkyl, in the presence of a base such as sodium hydride, in a solvent such as N,N-dimethylformamide and at a temperature of between 0° C. and the reflux temperature of the solvent.

The compounds of formula (XIX) are known or are prepared according to known methods.

The compounds of formula (XX) are prepared by reaction of a compound of formula (II) with potassium cyanide, in a solvent such as ethanol as a mixture with water and at a temperature of between ambient temperature and the reflux temperature of the solvent.

The compounds of formula (XXI) are prepared by reaction of a compound of formula:

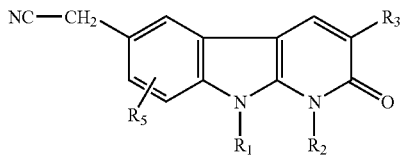

(XXVIII)

in which $R_1$, $R_2$, $R_3$, and $R_5$ are as defined for a compound of formula (I), with Bredereck's reagent under hot conditions.

The compounds of formula (XXII) are prepared by reaction of a compound of formula (VI) with (trimethylsilyl)acetylene, in the presence of $Pd(PPh_3)_4$, in a solvent such as pyrrolidine, at a temperature of 150° C., followed by basic hydrolysis.

The compounds of formulae (XXIII) and (XXV) are known and are prepared according to the methods described in WO2004/041817.

The compounds of formulae (XXIV) and (XXVII) are known or are prepared according to known methods.

The compounds of formula (XXVI) are prepared by reaction of the compounds of formula (XXIII) with compounds of formula:

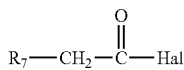

(XXIX)

in which $R_7$ is as defined for a compound of formula (I) and Hal is a halogen atom, in the presence of a Lewis acid such as aluminium chloride, in a solvent such as dichloromethane and at a temperature of between 0° C. and ambient temperature.

The compounds of formula (XXVIII) are prepared according to SCHEME I below:

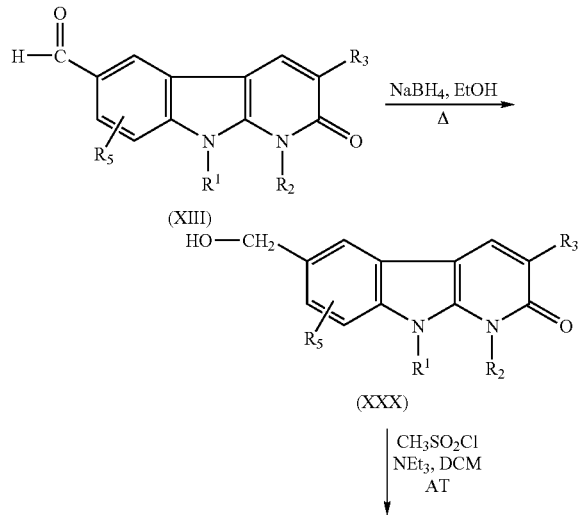

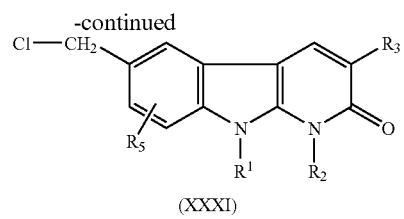

(XXXI)

Unless otherwise indicated, the proton nuclear magnetic resonance (H NMR) spectra are recorded in DMSO-$d_6$, the reference is placed is DMSO-$d_6$ which is at 2.50 ppm of tetramethylsilane.

The signals observed in NMR are expressed in the following way: s: singlet; bs: broad singlet; d: doublet; s.d: split doublet; t: triplet; st: split triplet; q: quadruplet; m: unresolved peak; mt: multiplet.

The following examples describe the preparation of certain compounds in accordance with the invention. These examples are not limiting and merely illustrate the present invention. The numbers of the compounds exemplified refer to those given in Table I hereinafter, which illustrates the chemical structures and the physical properties of some compounds according to the invention.

In the preparations and examples which will follow, the following abbreviations are used:
DIPEA: diisopropylethylamine
TEA: triethylamine
DMF: dimethylformamide
PE: petroleum ether
NMP: N-methylpyrrolidin-2-one
LAH: lithium aluminium hydride
THF: tetrahydrofuran
Ether: diethyl ether
DCM: dichloromethane
EtOAc: ethyl acetate
AcOH: acetic acid
dppp: 1,3-bis(diphenylphosphino)propane
iPrOH: propan-2-ol
Bredereck's reagent: tert-butoxybis(dimethylamino)methane
PyBOP: (benzotriazol-1-yloxy)tripyrrolidinophosphonium hexafluorophosphate
CNBr: cyanogen bromide
AT: ambient temperature
Mp: melting point
Preparations
Preparation 1.1

6-(Bromoacetyl)-3-(2,4-dichlorophenyl)-1-methyl-1, 9-dihydro-2H-pyrido[2,3-b]-indol-2-one A) N'-Phenylformic hydrazide 25 g of $K_2CO_3$ are added to a solution of 20 g of phenylhydrazine hydrochloride in 150 ml of methyl formate and 60 ml of water, and the mixture is refluxed for 1 hour and left at AT for 12 hours with stirring. The precipitate formed is filter-dried, and washed with a propan-2-ol/petroleum ether mixture. 18.8 g of the expected compound are obtained.

B) N-Methyl-N'-phenylacetohydrazide

A solution of 170 ml of 2M LiAlH$_4$ in THF is refluxed, a suspension of 18.8 g of the compound from the preceding stage in 120 ml of THF is slowly added and the refluxing is continued for 15 hours. The reaction mixture is cooled in an ice bath, 6 ml of water followed by 20 ml of 1N NaOH are added, dropwise, the mineral salts are filtered off and washed with EtOAc, and the filtrate is concentrated under vacuum. The residue is taken up in 150 ml of EtOAc, a solution of 48 g of $K_2CO_3$ in 100 ml of water is added, followed by 11 ml of acetic anhydride, and the mixture is left at AT for 2 hours with stirring. After separation by settling out, the organic phase is dried over $MgSO_4$ and the solvent is evaporated off under vacuum. The residue is taken up with petroleum ether and the crystalline product formed is filtered-dried. 19.9 g of the expected compound are obtained.

C) N-[1,3-Dihydro-2H-indol-2-ylidene]methanamine hydrochloride

A solution of 19.9 g of the compound from the preceding stage in 80 ml of $POCl_3$ is heated at 80° C. for 16 hours. After cooling to AT, ether is added, and the precipitate formed is filter-dried and washed with ether. The precipitate is taken up in 60 ml of EtOH, the product is refluxed for 4 hours, and the precipitate is filter-dried and washed with ether. 12 g of the expected compound are obtained.

D) 3-(2,4-Dichlorophenyl)-1-methyl-1,9-dihydro-2H-pyrido[2,3-b]indol-2-one

A solution of 5 g of the compound from the preceding stage in 25 ml of AcOH is heated at 110° C. for 15 minutes, 7.5 g of methyl 2-(2,4-dichlorophenyl)-3-(dimethylamino)acrylate are added and the mixture is heated at 110° C. for 16 hours. Water is added to the reaction mixture, and the precipitate formed is filter-dried and washed with a propan-2-ol/petroleum ether mixture (50/50; v/v). 7.8 g of the expected compound are obtained.

E) 6-(Bromoacetyl)-3-(2,4-dichlorophenyl)-1-methyl-1,9-dihydro-2H-pyrido[2,3-b]indol-2-one A solution of 2 g of the compound from the preceding stage in 60 ml of DCM is cooled to 0° C., 3.1 g of $AlCl_3$ are added, followed by 1 ml of bromoacetyl chloride, and the mixture is left at 0° C. for 1 hour with stirring. The reaction mixture is poured over ice, extracted with EtOAc and chromatographed on silica gel, elution being carried out with the EtOAc/cyclohexane (50/50; v/v) mixture, and then with EtOAc. 1.2 g of the expected compound are obtained.

$^1$H NMR: DMSO-$d_6$ (300 MHz): δ (ppm): 3.71: s: 3H, 4.94: s: 2H, 7.44-7.48: m: 2H, 7.59: d: 1H, 7.70: s: 1H, 7.90: d: 1H, 8.32: s: 1H, 8.68: s: 1H, 12.61: s: 1H.

Preparation 1.2

6-(Bromoacetyl)-3-(2,4-dichlorophenyl)-1,9-dimethyl-1,9-dihydro-2H-pyrido[2,3-b]indol-2-one

A) N,1-Dimethyl-1H-indol-2-amine

This compound is prepared according to the procedure described in WO 2004/041817, Mp=249° C.

B) 3-(2,4-Dichlorophenyl)-1,9-dimethyl-1,9-dihydro-2H-pyrido[2,3-b]indol-2-one A solution of 3 g of the compound from the preceding stage in 15 ml of AcOH is refluxed for 15 minutes, 4.2 g of methyl 2-(2,4-dichlorophenyl)-3-(dimethylamino)acrylate are added, and the mixture is refluxed for 16 hours. Water is added to the reaction mixture, and the precipitate formed is filter-dried and washed with MeOH and then with EtOAc. 4.1 g of the expected product are obtained.

C) 6-(Bromoacetyl)-3-(2,4-dichlorophenyl)-1,9-dimethyl-1,9-dihydro-2H-pyrido[2,3-b]indol-2-one A solution of 1.2 g of the compound from the preceding stage in 40 ml of DCM is cooled to 0° C., 1.8 g of $AlCl_3$ are added, followed, dropwise, by 0.6 ml of bromoacetyl chloride, and the mixture is left at AT for 1 hour with stirring. The reaction mixture is poured over ice, the product is extracted with DCM, the organic phase is dried over $Na_2SO_4$ and the solvent is evaporated off under vacuum. The residue is chromatographed on silica gel, elution being carried out with the EtOAc/cyclohexane (75/25; v/v) mixture, and then with EtOAc. 1 g of the expected compound is obtained.

$^1$H NMR: DMSO-$d_6$ (300 MHz): δ (ppm): 4.01: s: 3H, 4.19: s: 3H, 4.93: s: 2H, 7.41-7.49: m: 2H, 7.69: d: 1H, 7.75: d: 1H, 7.91: sd: 1H, 8.34: s: 1H, 8.67: d: 1H.

Preparation 1.3

6-(Chloroacetyl)-3-(2,4-dichlorophenyl)-1,9-dimethyl-1,9-dihydro-2H-pyrido[2,3-b]indol-2-one A solution of 0.7 g of the compound from stage B of preparation 1.2 in 25 ml of DCM is cooled to 0° C., 1.04 g of $AlCl_3$ are added, followed, dropwise, by 0.19 ml of chloroacetyl chloride, and the mixture is left at AT for 1 hour with stirring. The reaction mixture is poured over ice, the product is extracted with DCM, the organic phase is dried over $Na_2SO_4$ and the solvent is evaporated off under vacuum. The residue is chromatographed on silica gel, elution being carried out with the EtOAc/cyclohexane (75/25; v/v) mixture, then with EtOAc and, finally, with the EtOAc/MeOH/$NH_3$ (90/10/1; v/v/v) mixture. The product obtained is taken up in an EtOAc/cyclohexane (25/75; v/v) mixture and the precipitate formed is filter-dried.

0.56 g of the expected compound is obtained.

$^1$H NMR: DMSO-$d_6$ (300 MHz): δ (ppm): 4.03: s: 3H, 4.21: s: 3H, 5.22: s: 2H, 7.43-7.51: m: 2H, 7.70: d: 1H, 7.76: d: 1H, 7.91: sd: 1H, 8.35: s: 1H, 8.66: s: 1H.

Preparation 1.4

6-Bromo-3-(2,4-dichlorophenyl)-1-methyl-1,9-dihydro-2H-pyrido[2,3-b]indol-2-one This compound is prepared according to the procedure described in Example 114 in WO 2004/041817, Mp=386° C. (decomp).

Preparation 1.5

3-(2,4-Dichlorophenyl)-1,9-dimethyl-2-oxo-2,9-dihydro-1H-pyrido[2,3-b]indole-6-carbonitrile

A) N'-(4-Cyanophenyl)acetohydrazide 2.7 g of sodium acetate are added to a solution of 5 g of 4-cyanophenylhydrazine hydrochloride in 40 ml of acetic acid and the mixture is then heated at 80° C. for 20 hours. The reaction mixture is concentrated under vacuum, the residue is taken up with water, the product is extracted with EtOAc, the organic phase is washed with a saturated NaCl solution and dried over $MgSO_4$, and the solvent is evaporated off under vacuum. The residue is triturated in a PE/EtOAc (90/10; v/v) mixture and the precipitate formed is filter-dried. 4.8 g of the expected compound are obtained.

$^1$H NMR: CDCl$_3$ (300 MHz): δ (ppm): 1.92: s: 3H, 6.75: d: 2H, 7.53: d: 2H, 8.25: s: 1H, 9.76: s: 1H.

B) N'-(4-Cyanophenyl)-N,N'-dimethylacetohydrazide

A solution of 4.8 g of the compound obtained in the preceding stage in 20 ml of DMF is added, dropwise and at AT, to a suspension of 2.8 g of NaH at 60% in oil, in 50 ml of DMF, and the mixture is left stirring until no more gas is given off. 6.8 ml of methyl iodide are subsequently added and the mixture is then left at AT for 2 hours with stirring. The reaction mixture is poured into a saturated NH$_4$Cl solution, the product is extracted with EtOAc, the organic phase is washed with a saturated NaCl solution and dried over MgSO$_4$, and the solvent is evaporated off under vacuum. The residue is taken up in PE and the precipitate formed is filter-dried. 4.5 g of the expected compound are obtained.
$^1$H NMR: CDCl$_3$ (300 MHz): δ (ppm): 2.04: s: 3H, 3.03: s: 3H, 3.21: s: 3H, 6.70: d: 3H, 7.57: d: 2H.

C) 1-Methyl-2-(methylamino)-1H-indole-5-carbonitrile

A solution of 4.0 g of the compound obtained in the preceding stage in 30 ml of POCl$_3$ is heated at 75° C. for 1 hour 30 minutes. After cooling to AT, the precipitate formed is filter-dried and washed with ether. 3.4 g of the expected compound are obtained.

D) 3-(2,4-Dichlorophenyl)-1,9-dimethyl-2-oxo-2,9-dihydro-1H-pyrido[2,3-b]indole-6-carbonitrile A mixture of 0.4 g of the compound obtained in the preceding stage in 4 ml of acetic acid is heated at 100° C. for 15 minutes, then 0.43 g of methyl 2-(2,4-dichloro-phenyl)-3-(dimethylamino)acrylate are added and the mixture is heated at 100° C. for 3 hours. After cooling to AT, water is added to the reaction mixture, and the beige precipitate formed is filter-dried and washed with water. The precipitate is taken up in MeOH and the solvent is concentrated under vacuum. 0.5 g of the expected compound is obtained.
$^1$H NMR: DMSO-d$_6$ (300 MHz): δ (ppm): 4.02: s: 3H, 4.21: s: 3H, 7.42-7.51: m: 2H, 7.66-7.70: m: 2H, 7.83: d: 1H, 8.31: s: 1H, 8.42: s: 1H.

Preparation 1.6

3-(2,4-Dichlorophenyl)-1,9-dimethyl-2-oxo-2,9-dihydro-1H-pyrido[2,3-b]indole-6-carbothioamide 0.4 ml of O,O'-diethyldithiophosphate is added to a solution of 0.5 g of the compound from preparation 1.5 in 10 ml of NMP and 1.5 ml of water, and the mixture is heated at 90° C. overnight. After cooling to AT, the reaction mixture is poured into a saturated NH$_4$Cl solution, and the precipitate formed is filter-dried, washed with water and then with the propan-2-ol/PE (50/50; v/v) mixture. The precipitate is taken up with MeOH and the solvent is concentrated under vacuum. The residue is chromatographed on silica gel, elution being carried out with the DCM/MeOH mixture from (99/1; v/v) to (98/2; v/v). 0.41 g of the expected compound is obtained.

Preparation 1.7

3-(2,4-Dichlorophenyl)-1,9-dimethyl-2-oxo-2,9-dihydro-1H-pyrido[2,3-b]indole-6-carbaldehyde 3.4 g of NaH$_2$PO$_2$ and 1.7 ml of Raney® nickel are added to a solution of 0.45 g of the compound from preparation 1.5 in 30 ml of pyridine, 10 ml of acetic acid and 6 ml of water, and the mixture is heated at 65° C. for 36 hours. The catalyst is filtered off, washing with MeOH is performed, and the filtrate is concentrated under vacuum. The residue is taken up with water, the product is extracted with EtOAc, the organic phase is washed with a saturated NaCl solution and dried over MgSO$_4$, and the solvent is evaporated off under vacuum. The residue is taken up in an EtOAc/PE (50/50; v/v) mixture and the precipitate formed is filter-dried. 0.2 g of the expected compound is obtained, Mp=284° C.

Preparation 1.8

2-[3-(2,4-Dichlorophenyl)-1,9-dimethyl-2-oxo-2,9-dihydro-1H-pyrido[2,3-b]indol-6-yl]-3-(dimethylamino)acrylonitrile A) 3-(2,4-Dichlorophenyl)-6-(hydroxymethyl)-1,9-dimethyl-1,9-dihydro-2H-pyrido[2,3-b]indol-2-one 0.06 g of NaBH$_4$ is added to a solution of 0.5 g of the compound from preparation 1.7 in 15 ml of EtOH, and the mixture is refluxed for 5 hours. After cooling to AT, 1 ml of 6N NaOH is added and the mixture is concentrated under vacuum. The residue is triturated in water, and the precipitate formed is filter-dried and washed with water. The precipitate is taken up in MeOH and the solvent is evaporated off under vacuum. 0.49 g of the expected compound are obtained.

B) 6-(Chloromethyl)-3-(2,4-dichlorophenyl)-1,9-dimethyl-1,9-dihydro-2H-pyrido[2,3-b]indol-2-one 0.27 ml of methylsulphonyl chloride is added to a solution of 0.49 g of the compound from the preceding stage and 0.53 ml of triethylamine in 10 ml of DCM, and the mixture is left at AT for 3 days with stirring. The reaction mixture is chromatographed on silica gel, elution being carried with the EtOAc/cyclohexane (75/25; v/v) mixture. 0.4 g of the expected compound is obtained.

C) [3-(2,4-Dichlorophenyl)-1,9-dimethyl-2-oxo-2,9-dihydro-1H-pyrido[2,3-b]indol-6-yl]acetonitrile 3 ml of DMSO are added, dropwise, to a mixture of 0.2 g of the compound from the preceding stage and 0.049 g of NaCN in 2 ml of DCM, and the mixture is left at AT overnight with stirring. Water and EtOAc are added, the mixture is separated by settling out, the organic phase is washed with water and dried over Na$_2$SO$_4$, and the solvent is evaporated off under vacuum. The residue is taken up with MeOH and the product is evaporated under vacuum. 0.18 g of the expected compound is obtained.

D) 2-[3-(2,4-Dichlorophenyl)-1,9-dimethyl-2-oxo-2, 9-dihydro-1H-pyrido[2,3-b]indol-6-yl]-3-(dimethylamino)acrylonitrile A mixture of 0.18 g of the compound from the preceding stage and 5 ml of Bredereck's reagent is heated at 100° C. overnight. After cooling to AT, PE and water are added, and the precipitate formed is filter-dried, washed with water and then with PE/propan-2-ol (50/50; v/v) mixture. The precipitate is taken up in MeOH and the product is evaporated under vacuum. 0.15 g of the expected compound is obtained.
$^1$H NMR: DMSO-d$_6$ (300 MHz): δ (ppm): 3.19: s: 6H, 4.00: s: 3H, 4.13: s: 3H, 7.22-7.26: sd: 1H, 7.39-7.46: m: 3H, 7.54: d: 1H, 7.68: s: 1H, 7.80: s: 1H, 8.18: s: 1H.

Preparation 1.9

3-(2,4-Dichlorophenyl)-6-[3-(dimethylamino)prop-2-enoyl]-1-methyl-9-[[2-(trimethylsilyl)ethoxy]methyl]-1,9-dihydro-2H-pyrido[2,3-b]indol-2-one A) 6-Acetyl-3-(2,4-dichlorophenyl)-1-methyl-1,9-dihydro-2H-pyrido[2,3-b]indol-2-one A solution of 1.5 g of the compound from stage D of preparation 1.1 in 60 ml of DCM is cooled to 0° C., 2.33 g of $AlCl_3$ and then 0.624 ml of acetyl chloride are added, and the mixture is left at AT for 2 hours with stirring. The reaction mixture is poured over ice, the product is extracted with DCM, the precipitate formed is filter-dried, the filter-drying liquors are extracted with DCM, and the organic phase is dried over $MgSO_4$ and evaporated under vacuum. The residue and the precipitate are combined, the combination is triturated in the MeOH/ether mixture and the product is filter-dried. 1.36 g of the expected compound are obtained.

B) 6-Acetyl-3-(2,4-dichlorophenyl)-1-methyl-[[2-(trimethylsilyl)ethoxy]methyl]-1,9-dihydro-2H-pyrido[2,3-b]indol-2-one 0.311 g of NaH at 60% in oil and then 0.69 ml of 2-(trimethylsilyl)ethoxymethyl chloride are added to a solution of 1 g of the compound from the preceding stage in 13 ml of DMF, and the mixture is left at AT for 5 hours with stirring. A saturated NaCl solution is added, the mixture is extracted with EtOAc, the organic phase is washed with a saturated NaCl solution and dried over $MgSO_4$, and the solvent is evaporated off under vacuum. The residue is chromatographed on silica gel, elution being carried out with cyclohexane and then with the gradient of the cyclohexane/EtOAc mixture of (90/10; v/v) to (50/50; v/v). 0.639 g of the expected compound is obtained.

C) 3-(2,4-Dichlorophenyl)-6-[3-(dimethylamino)prop-2-enoyl]-1-methyl-9-[[2-(trimethylsilyl)ethoxy]methyl]-1,9-dihydro-2H-pyrido[2,3-b]indol-2-one A solution of 0.25 g of the compound from the preceding stage in 5 ml of Bredereck's reagent is heated at 100° C. overnight. After cooling to AT, PE is added, and the precipitate formed is filter-dried, washed with PE and dried. 0.236 g of the expected compound is obtained.

Preparation 1.10

3-(2,4-Dichlorophenyl)-6-[3-(dimethylamino)prop-2-enoyl]-1,9-dimethyl-1,9-dihydro-2H-pyrido[2,3-b]indol-2-one A) N'-(4-Iodophenyl)acetohydrazide A mixture of 10 g of 4-iodophenylhydrazine in 80 ml of acetic acid is refluxed for 5 hours. The reaction mixture is concentrated under vacuum, the residue is taken up with water, and the precipitate formed is filter-dried and washed with a propan-2-ol/PE (50/50; v/v) mixture. 9 g of the expected compound are obtained.

B) N'-(4-iodophenyl)-N,N'-dimethylacetohydrazide

A solution of 9 g of the compound from the preceding stage in 30 ml of DMF is added to a suspension of 3.9 g of NaH at 60% in oil, in 50 ml of DMF, and the mixture is left at AT for 5 minutes with stirring. 6.1 ml of methyl iodide are subsequently added and the mixture is left at AT for 1 hour with stirring. The reaction mixture is poured into a saturated $NH_4Cl$ solution, the product is extracted with EtOAc, the organic phase is washed with a saturated NaCl solution and dried over $MgSO_4$, and the solvent is evaporated off under vacuum. The oily residue is triturated in PE and the precipitate formed is filter-dried. 6.7 g of the expected compound are obtained.

C) N-[5-Iodo-1-methyl-1,3-dihydro-2H-indol-2-ylidene)methanamine hydrochloride

A mixture of 6.7 g of the compound from the preceding stage and 50 ml of $POCl_3$ are heated at 80° C. for 16 hours. After cooling to AT, ether is added, and the precipitate formed is filter-dried and washed with ether. The precipitate is taken up in 20 ml of EtOH and the product is refluxed for 5 hours. The precipitate formed is filter-dried and washed with ether. 4.4 g of the expected compound are obtained.

D) 3-(2,4-Dichlorophenyl)-6-iodo-1,9-dimethyl-1,9-dihydro-2H-pyrido[2,3-b]indol-2-one A solution of 1.4 g of the compound from the preceding stage in 8 ml of acetic acid is refluxed for 15 minutes, 1.2 g of methyl 2-(2,4-dichlorophenyl)-3-(dimethylamino)acrylate are added and the mixture is then refluxed for 16 hours. The reaction mixture is poured into water, the product is extracted with EtOAc, the organic phase is washed with a saturated NaCl solution and dried over $MgSO_4$, and the solvent is evaporated off under vacuum. The residue is chromatographed on silica gel, elution being carried out with the EtOAc/cyclohexane (75/25; v/v) mixture. The product obtained is taken with an EtOAc/cyclohexane (25/75; v/v) mixture and the precipitate formed is filter-dried. 1.3 g of the expected compound are obtained, Mp=223-225° C.

E) 6-Acetyl-3-(2,4-dichlorophenyl)-1,9-dimethyl-1,9-dihydro-2H-pyrido[2,3-b]indol-2-one 0.5 g of $Cu_2O$ is added to a solution of 0.4 g of the compound from the preceding stage in 15 ml of NMP, and the reaction mixture is then degassed by sparging with argon for 30 minutes. 0.075 g of palladium(II) acetate, 0.273 g of 1,3-bis(diphenylphosphino)propane and 0.64 ml of tributyl-(1-ethoxyvinyl)stannane are subsequently added and the mixture is then heated at 80° C. for 8 hours. The reaction mixture is poured into 100 ml of 1N HCl, the mixture is left stirring for 10 minutes, and the precipitate formed is filter-dried. The precipitate is chromatographed on silica gel, elution being carried out with the EtOAc/cyclohexane (75/25; v/v) mixture. The product obtained is triturated in an EtOAc/cyclohexane (75/25; v/v) mixture and the precipitate formed is filter-dried. 0.15 g of the expected compound is obtained, Mp=254-255° C.

F) 3-(2,4-Dichlorophenyl)-6-[3-(dimethylamino)prop-2-enoyl]-1,9-dimethyl-1,9-dihydro-2H-pyrido[2,3-b]indol-2-one A solution of 0.5 g of the compound from the preceding stage in 5 ml of Bredereck's reagent is heated at 100° C. overnight. After cooling to ambient temperature, PE is added, and the precipitate formed is filter-dried and washed with PE. 0.575 g of the expected compound is obtained.

Preparation 1.11

3-(2,4-Dichlorophenyl)-1,9-dimethyl-2-oxo-2,9-dihydro-1H-pyrido[2,3-b]indole-6-carboxamide A solution of 1.28 g of the compound from stage D of preparation 1.10, 0.055 g of $PdCl_2(PPh_3)_2$ and 2.24 ml of 1,1,1,3,3,3-hexamethyldisilazane in 8.5 ml of DMF is sparged with CO for 5 minutes, and then the mixture is heated at 80° C. for 12 hours under an atmosphere of CO. After cooling to AT, 1.39 ml of MeOH are added and the mixture is left stirring for 10 minutes. The reaction mixture is poured into 56 ml of 2N $H_2SO_4$, and the precipitate formed is filter-dried and washed with water and then with EtOAc. The filtrate is extracted with EtOAc, the organic phase is washed with a saturated $NaHCO_3$ solution and with a saturated NaCl solution and dried over $MgSO_4$, and the solvent is evaporated off under vacuum. The precipitate and the residue are chromatographed on silica gel, elution being carried with the EtOAc/cyclohexane (80/20; v/v) mixture. 0.6 g of the expected compound is obtained.
$^1$H NMR: $CDCl_3$ (300 MHz): δ (ppm): 4.09: s: 3H, 4.17: s: 3H, 7.28-7.45: m: 3H, 7.50: d: 1H, 7.79: sd: 1H, 8.02: s: 1H, 8.25: d: 1H.

Preparation 1.12

4-[3-(2,4-Dichlorophenyl)-1,9-dimethyl-2-oxo-2,9-dihydro-1H-pyrido[2,3-b]indol-6-yl]-2,4-dioxobutanoate A solution of 0.3 g of the compound from stage E of preparation 1.10 in 4 ml of DMF is cooled to 5° C., 0.036 g of NaH at 60% in oil and 0.1 g of dimethyl oxalate are added, and the mixture is left at AT for 1 hour with stirring and then heated at 50° C. for 1 hour. After cooling to AT, a 2.4N HCl solution is added, the mixture is extracted with EtOAc, the organic phase is washed with water and dried over $MgSO_4$, and the solvent is evaporated off under vacuum. 0.46 g of the expected compound is obtained, which compound is used as it is.

Preparation 1.13

3-(2,4-Dichlorophenyl)-6-[3-(dimethylamino)-2-methylprop-2-enoyl]-1,9-dimethyl-1,9-dihydro-2H-pyrido[2,3-b]indol-2-one A) 3-(2,4-Dichlorophenyl)-1,9-dimethyl-6-propionyl-1,9-dihydro-2H-pyrido[2,3-b]indol-2-one A solution of 0.9 g of the compound from stage B of preparation 1.2 in 50 ml of DCM is cooled to 0° C., 1.34 g of $AlCl_3$ is added, in small portions, followed, dropwise, by 0.5 ml of propionyl chloride, and the mixture is left at 0° C. for 2 hours with stirring. The reaction mixture is poured over ice, the product is extracted with DCM, the organic phase is dried over $Na_2SO_4$, and the solvent is evaporated off under vacuum. The residue is taken up in a PE/EtOAc (90/10; v/v) mixture and the precipitate formed is filter-dried. 0.65 g of the expected compound is obtained.

B) 3-(2,4-Dichlorophenyl)-6-[3-(dimethylamino)-2-methylprop-2-enoyl]-1,9-dimethyl-1,9-dihydro-2H-pyrido[2,3-b]indol-2-one A mixture of 0.6 g of the compound from the preceding stage and 2 ml of Bredereck's reagent is heated at 100° C. for 16 hours. After cooling to AT, PE is added and the precipitate formed is filter-dried. 0.63 g of the expected compound is obtained.
$^1$H NMR: DMSO-$d_6$ (300 MHz): δ (ppm): 2.04: s: 3H, 2.98: s: 6H, 4.02: s: 3H, 4.17: s: 3H, 6.89: s: 1H, 7.26: d: 1H, 7.44: m: 2H, 7.59: d: 1H, 7.68: s: 1H, 7.89: s: 1H, 8.29: s: 1H.

Preparation 1.14

1-[3-(2,4-Dichlorophenyl)-1,9-dimethyl-2-oxo-2,9-dihydro-1H-pyrido[2,3-b]indol-6-yl]butane-1,3-dione A mixture of 0.052 g of NaH at 60% in oil and 0.12 ml of EtOAc in 2 ml of THF is left stirring for 10 minutes and then a solution of 0.246 g of the compound from stage E of preparation 1.10, 2 drops of EtOH and 0.0035 g of dibenzo-18-crown-6 in 2 ml of THF is added and the mixture is heated at 80° C. for 3 hours. After cooling to AT, a 1N HCl solution is added, the mixture is extracted with EtOAc, and the solvent is evaporated off under vacuum. The residue is taken up with MeOH, and the precipitate formed is filter-dried and washed with MeOH. 0.242 g of the expected compound is obtained.
$^1$H NMR: DMSO-$d_6$ (300 MHz): δ (ppm): 2.17: s: 2H, 2.25: s: 1H, 4.02: s: 3H, 4.20: s: 3H, 6.63: s: 1H, 7.40-7.52: m: 2H, 7.67-7.80: m: 2H, 7.85-7.95: m: 1H, 8.36: d: 1H, 8.62: d: 1H.

Preparation 1.15

3-(2,4-Dichlorophenyl)-6-ethynyl-1,9-dimethyl-1,9-dihydro-2H-pyrido[2,3-b]indol-2-one A) 3-(2,4-Dichlorophenyl)-1,9-dimethyl-6-[(trimethylsilyl)ethynyl]-1,9-dihydro-2H-pyrido[2,3-b]indol-2-one A solution of 0.5 g of the compound from stage D of preparation 1.10, 0.161 ml of (trimethylsilyl)acetylene and 0.06 g of Pd $(PPh_3)_4$ in 5 ml of pyrrolidine is sparged with argon for 5 minutes and then the mixture is heated at 150° C. in a microwave. The reaction mixture is chromatographed on silica gel, elution being carried out with the EtOAc/cyclohexane (70/30; v/v) mixture. 0.292 g of the expected compound is obtained.

B) 3-(2,4-Dichlorophenyl)-6-ethynyl-1,9-dimethyl-1,9-dihydro-2H-pyrido[2,3-b]indol-2-one 0.079 g of KOH is added to a solution of 0.29 g of the compound from the preceding stage in 6.7 ml of THF, 1.7 ml of MeOH and 0.3 ml of water and the mixture is left at AT for 3 hours with stirring. The mixture is concentrated under vacuum and the residue is chromatographed on silica gel, elution being carried out with the EtOAc/cyclohexane (80/20; v/v) mixture. The product obtained is triturated in MeOH, and the precipitate formed is filter-dried and washed with MeOH. 0.2 g of the expected compound is obtained, Mp=184-185° C.

Preparation 1.16

3-(2,4-Dichlorophenyl)-1,9-dimethyl-2-oxo-2,9-dihydro-1H-pyrido[2,3-b]indole-6-carboxylic acid A) Methyl 4-(2-acetylhydrazino)benzoate 5.5 g of methyl 4-hydrazinobenzoate are dissolved in 38.2 ml of AcOH containing 2.4 g of sodium acetate, and the mixture is heated at 80° C. for 18 hours. The mineral is filter-dried, then evaporation is performed and the product is taken up with a minimum of Et₂O. The product is filter-dried so as to obtain 7.97 g of the expected compound.

B) Methyl 4-(2-acetyl-1,2-dimethylhydrazino)benzoate 2.95 g of NaH at 95% are suspended in 90 ml of DMF and 8.135 g of the compound from the preceding stage in solution in a minimum amount of DMF are added dropwise, and then, after a few minutes, 9.75 ml of methyl iodide are added dropwise. The mixture is stirred at AT for 1 hour. The medium is poured into a saturated NH₄Cl solution and extracted with EtOAc. The organic phase is washed with NaCl, dried, and evaporated to give 5.4 g of the expected compound.

C) Methyl 1-methyl-2-(methylamino)-1H-indole-5-carboxylate 5.4 g of the compound from the preceding stage and 62 ml of phosphorus oxychloride are mixed and the mixture is heated at 80° C. for 2 and a half hours. The medium is evaporated off and the product is taken up with EtOAc. The solid formed is filter-dried, washed with EtOAc, and dried to give 4 g of the expected compound.

NMR MeOD (250 MHz): 3.2 ppm: s: 3H, 3.6 ppm: s: 3H, 3.9 ppm: s: 3H, 7.3-7.4 ppm: m: 2H, 8.1-8.2 ppm: m: 2H.

D) Methyl 3-(2,4-dichlorophenyl)-1,9-dimethyl-2-oxo-2,9-dihydro-1H-pyrido[2,3-b]indole-6-carboxylate A mixture of 25.47 g of the compound obtained in the preceding stage and 27.4 g of methyl 2-(2,4-dichlorophenyl)-3-(dimethylamino)acrylate in 100 ml of acetic acid is heated at 100° C. for 2 hours. The hot reaction mixture is poured into 500 ml of a water/ice mixture, and the precipitate formed is filter-dried, washed with water then with ether, and dried. 22 g of the expected compound are obtained.

E) 3-(2,4-Dichlorophenyl)-1,9-dimethyl-2-oxo-2,9-dihydro-1H-pyrido[2,3-b]indole-6-carboxylic acid A solution of 5.14 g of KOH pellets in 90 ml of water is added to a mixture of 9.5 g of the compound obtained in the preceding stage in 100 ml of MeOH, and the mixture is refluxed for 18 hours. After cooling to AT and then in an ice bath, the reaction mixture is acidified to PH=1 by the addition of a 5N HCl solution, diluting with water to allow stirring. The precipitate formed is filter-dried, washed with water and dried. 9.1 g of the expected compound is obtained.

Preparation 1.17

3-(2,4-Dichlorophenyl)-1,9-dimethyl-2-oxo-N-prop-2-yn-1-yl-2,9-dihydro-1H-pyrido[2,3-b]indole-6-carboxamide A mixture of 0.2 g of the compound from preparation 1.16, 0.038 ml of propargylamine, 0.285 g of PyBOP and 0.096 ml of DIPEA in 7 ml of DCM and 1.3 ml of DMF is left at AT overnight with stirring. The reaction mixture is concentrated under vacuum, the residue is taken up with a saturated NH₄Cl solution, the product is extracted with EtOAc, the organic phase is dried over MgSO4 and the solvent is evaporated off under vacuum. The residue is taken up in an MeOH/DCM mixture and the precipitate formed is filter-dried. 0.21 g of the expected compound is obtained.

EXAMPLE 1

Compound No. 1

3-(2,4-Dichlorophenyl)-1-methyl-6-(2-methyl-1,3-thiazol-4-yl)-1,9-dihydro-2H-pyrido[2,3-b]indol-2-one 0.08 g of thioacetamide is added to a solution of 0.5 g of the compound from preparation 1.1 in 3 ml of NMP, and the mixture is then heated at 150° C. for 30 minutes. After cooling to AT, water and EtOAc are added, the mixture is separated by settling out, the organic phase is washed with a saturated NH4Cl solution and with a saturated NaCl solution and dried over Na2SO4, and the solvent is evaporated off under vacuum. The residue is taken up in an MeOH/PE (50/50; v/v) mixture, and the precipitate formed is filter-dried and washed with EtOAc. 0.21 g of the expected compound is obtained, Mp>350° C. (decomp).

1H NMR: DMSO-d6 (300 MHz): δ (ppm): 2.72: s: 3H, 3.70: s: 3H, 7.46-7.52: m: 3H, 7.69: s: 1H, 7.77-7.85: m: 2H, 8.25: s: 1H, 8.44: s: 1H, 12.21: s: 1H.

EXAMPLE 2

Compound No. 2

6-(2-Amino-1,3-thiazol-4-yl)-3-(2,4-dichlorophenyl)-1-methyl-1,9-dihydro-2H-pyrido[2,3-b]indol-2-one 0.04 g of thiourea is added to a solution of 0.2 g of the compound from preparation 1.1 in 7 ml of MeOH, and the mixture is then refluxed for 18 hours. The precipitate formed is filter-dried, triturated in a saturated K2CO3 solution, filter-dried, and washed with water and then with the propan-2-ol/PE (50/50; v/v) mixture. 0.17 g of the expected compound is obtained.

1H NMR: DMSO-d6 (300 MHz): δ (ppm): 3.71: s: 3H, 7.06: s: 1H, 7.43-7.50: m: 2H, 7.57: s: 2H, 7.70: s: 1H, 8.19: s: 1H, 8.25: s: 1H, 8.60-8.85: bs: 2H; 12.40: s: 1H.

EXAMPLE 3

Compound No. 3

3-(2,4-Dichlorophenyl)-6-[2-(hydroxymethyl)-1,3-thiazol-4-yl]-1-methyl-1,9-dihydro-2H-pyrido[2,3-b]indol-2-one A) [4-[3-(2,4-Dichlorophenyl)-1-methyl-2-oxo-2,9-dihydro-1H-pyrido[2,3-b]indol-6-yl]1,3-thiazol-2-yl] methyl pivalate 0.12 g of 2-amino-2-thioxoethyl pivalate is added to a solution of 0.33 g of the compound from preparation 1.1 in 15 ml of EtOH and the mixture is refluxed for 3 days. The reaction mixture is taken up in DCM and MeOH and chromatographed on silica gel, elution being carried out with the EtOAc/cyclohexane (75/25; v/v) mixture. 0.18 g of the expected compound is obtained.

B) 3-(2,4-Dichlorophenyl)-6-[2-(hydroxymethyl)-1,3-thiazol-4-yl]-1-methyl-1,9-dihydro-2H-pyrido[2,3-b]indol-2-one A suspension of 0.18 g of the compound from the preceding stage in 5 ml of MeOH is added to a solution of 0.016 g of sodium in 10 ml of MeOH and the mixture is left at AT for 16 hours with stirring. Water is added, the mixture is extracted with EtOAc, the organic phase is dried over MgSO4, and the solvent is evaporated off under vacuum. The residue is chromatographed on silica gel, elution being carried out with the EtOAc/cyclohexane (90/10; v/v) mixture. 0.06 g of the expected compound is obtained.

1H NMR: DMSO-d6 (300 MHz): δ (ppm): 3.69: s: 3H, 4.80: s: 2H, 6.11: m: 1H, 7.46-7.52: m: 3H, 7.69: s: 1H, 7.82: d: 1H, 7.88: s: 1H, 8.25: s: 1H, 8.44: s: 1H, 12.20: s: 1H.

EXAMPLE 4

Compound No. 4

3-(2,4-Dichlorophenyl)-1-methyl-6-(2-methyl-1,3-oxazol-4-yl)-1,9-dihydro-2H-pyrido[2,3-b]indol-2-one 0.064 g of acetamide is added to a solution of 0.2 g of the compound from preparation 1.1 in 2 ml of NMP, and the mixture is heated at 150° C. for 2 hours. Water is added, the mixture is extracted with EtOAc, the organic phase is dried over Na2SO4, and the solvent is evaporated off under vacuum. The residue is chromatographed on silica gel, elution being carried out with the EtOAc/cyclohexane (75/25; v/v) mixture. The product obtained is taken up in 5 ml of MeOH, titration is carried out, and the precipitate formed is filter-dried and washed with PE. 0.12 g of the expected compound is obtained.

1H NMR: DMSO-d6 (300 MHz): δ (ppm): 2.45: s: 3H, 3.67: s: 3H, 7.44-7.52: m: 3H, 7.60: d: 1H, 7.67: s: 1H, 8.20-8.34: m: 3H, 12.18: s: 1H.

EXAMPLE 5

Compound No. 5

3-(2,4-Dichlorophenyl)-1-methyl-6-(2-methyl-1,3-oxazol-5-yl)-1,9-dihydro-2H-pyrido[2,3-b]indol-2-one A) 6-(Aminoacetyl)-3-(2,4-dichlorophenyl)-1-methyl-1,9-dihydro-2H-pyrido[2,3-b]indol-2-one hydrochloride A mixture of 0.845 g of the compound from preparation 1.1 and 0.255 g of hexamethylenetetramine in 13 ml of chloroform is left at AT for 20 hours with stirring. The precipitate formed is filter-dried, and washed with DCM then with ether. The precipitate is taken up in 3.5 ml of EtOH, 0.395 ml of 37% HCl is added, and the mixture is heated at 50° C. for 16 hours. The precipitate formed is filter-dried, washed with water and dried under vacuum. 0.547 g of the expected compound is obtained.

B) 3-(2,4-Dichlorophenyl)-1-methyl-6-(2-methyl-1,3-oxazol-5-yl)-1,9-dihydro-2H-pyrido[2,3-b]indol-2-one 6 mg of para-toluenesulphonic acid monohydrate are added to a solution of 0.5 g of the compound from the preceding stage in 10 ml of triethyl orthoacetate, and the mixture is heated at 140° C. for 45 minutes. After cooling to AT, the reaction mixture is dissolved with DCM and chromatographed on silica gel, elution being carried out with EtOAc and then with the EtOAc/MeOH (97/3; v/v) mixture. 0.045 g of the expected compound is obtained, Mp=338-340° C.

EXAMPLE 6

Compound No. 6

3-(2,4-Dichlorophenyl)-1,9-dimethyl-6-(2-methyl-1,3-thiazol-4-yl)-1,9-dihydro-2H-pyrido[2,3-b]indol-2-one 0.047 g of thioacetamide is added to a solution of 0.2 g of the compound from preparation 1.2 in 20 ml of MeOH, and then the mixture is refluxed for 48 hours. The precipitate formed is filter-dried and washed with PE. The precipitate is dissolved in DCM and chromatographed on silica gel, elution being carried out with the DCM/MeOH (99/1; v/v) mixture. 0.13 g of the expected compound is obtained, Mp=253-254° C.: 1H NMR: DMSO-d6 (300 MHz): δ (ppm): 2.70: s: 3H, 3.99: s: 3H, 4.15: s: 3H, 7.44: m: 2H, 7.62-7.67: m: 2H, 7.79: s: 1H, 7.86: d: 1H, 8.26: s: 1H, 8.43: s: 1H.

EXAMPLE 7

Compound No. 7

3-(2,4-Dichlorophenyl)-1,9-dimethyl-6-[2-(methylamino)-1,3-thiazol-4-yl]-1,9-dihydro-2H-pyrido[2,3-b]indol-2-one 0.045 g of N-methylthiourea is added to a solution of 0.2 g of the compound from preparation 1.2 in 10 ml of MeOH, and then the mixture is refluxed for 16 hours. The precipitate formed is filter-dried and washed with a propan-2-ol/PE (50/50; v/v) mixture. 0.19 g of the expected compound is obtained.

1H NMR: DMSO-d6 (300 MHz): δ (ppm): 3.03: s: 3H, 4.03: s: 3H, 4.20: s: 3H, 7.08: s: 1H, 7.42-7.48: m: 2H, 7.70-7.72: m: 3H, 8.23: s: 1H, 8.30: s: 1H.

EXAMPLE 8

Compound No. 8

[4-[3-(2,4-Dichlorophenyl)-1,9-dimethyl-2-oxo-2,9-dihydro-1H-pyrido[2,3-b]indol-6-yl]-1,3-thiazol-2-yl]methyl pivalate 0.25 g of 2-amino-2-thioxoyethyl pivalate is added to a solution of 0.45 g of the compound from preparation 1.2 in 20 ml of EtOH, and the mixture is refluxed for 3 days. The precipitate formed is filter-dried and washed with an MeOH/PE (50/50; v/v) mixture. The precipitate is dissolved in DCM and chromatographed on silica gel, elution being carried out with the DCM/MeOH (99/1; v/v) mixture. The product obtained is taken up in PE and the precipitate is filter-dried. 0.4 g of the expected compound is obtained, Mp=193-195° C.

1H NMR: DMSO-d6 (300 MHz): δ (ppm): 1.23: s: 9H, 4.02: s: 3H, 4.18: s: 3H, 5.46: s: 2H, 7.47: s: 2H, 7.68: s: 2H, 7.89: m: 1H, 8.04: s: 1H, 8.28: s: 1H, 8.48: s: 1H.

EXAMPLE 9

Compound No. 9

3-(2,4-Dichlorophenyl)-6-[2-(hydroxymethyl)-1,3-thiazol-4-yl]-1,9-dimethyl-1,9-dihydro-2H-pyrido[2,3-b]indol-2-one 0.2 g of compound No. 8 is added to a solution of 0.017 g of sodium in 20 ml of MeOH, and the mixture is left at AT for 6 hours with stirring. The precipitate formed is filter-dried, and washed with water, with a propan-2-ol/PE (50/50; v/v) mixture and then with DCM. 0.16 g of the expected compound is obtained, Mp=261-262° C.

1H NMR: DMSO-d6 (300 MHz): δ (ppm): 4.01: s: 3H, 4.17: s: 3H, 4.80: s: 2H, 6.12: s: 1H, 7.46: s: 2H, 7.64-7.69: m: 2H, 7.88-7.92: m: 2H, 8.28: s: 1H, 8.46: s: 1H.

EXAMPLE 10

Compound No. 10

3-(2,4-Dichlorophenyl)-6-[2-(ethoxymethyl)-1,3-thiazol-4-yl]-1,9-dimethyl-1,9-dihydro-2H-pyrido[2,3-b]indol-2-one 0.02 g of NaH at 60% in oil is added to a solution of 0.13 g of compound No. 9 in 10 ml of DMF, and the mixture is left at AT for 30 minutes with stirring. 0.05 ml of iodoethane is subsequently added and the mixture is left at AT for 1 hour with stirring. The reaction mixture is poured into a saturated NH4Cl solution, the product is extracted with EtOAc, the organic phase is washed with a saturated NaCl solution and dried over Na2SO4, and the solvent is evaporated off under vacuum. The residue is chromatographed on silica gel, elution being carried out with EtOAc. The product obtained is taken up with PE and the precipitate formed is filter-dried. 0.1 g of the expected compound is obtained.

1H NMR: DMSO-d6 (300 MHz): δ (ppm): 1.20: t: 3H, 3.64: q: 2H, 4.02: s: 3H, 4.18: s: 3H, 4.81: s: 2H, 7.46: s: 2H, 7.65-7.69: m: 2H, 7.89: d: 1H, 7.99: s: 1H, 8.28: s: 1H, 8.47: s: 1H.

EXAMPLE 11

Compound No. 11

[4-[3-(2,4-Dichlorophenyl)-1,9-dimethyl-2-oxo-2,9-dihydro-1H-pyrido[2,3-b]indol-6-yl]-1,3-thiazol-2-yl]methyl cyclopropanecarboxylate 0.1 ml of cyclopropanecarbonyl chloride is added to a solution of 0.1 g of compound No. 9 in 5 ml of pyridine and the mixture is left at AT for 48 hours with stirring. The reaction mixture is poured into water, the product is extracted with EtOAc, the organic phase is washed with a saturated NH4Cl solution and dried over Na2SO4, and the solvent is evaporated off under vacuum. The residue is chromatographed on silica gel, elution being carried out with the EtOAc/cyclohexane (90/10; v/v) mixture. The product obtained is taken up in an EtOAc/cyclohexane (10/90; v/v) mixture and the precipitate formed is filter-dried. 0.105 g of the expected compound is obtained.

1H NMR: DMSO-d6 (300 MHz): δ (ppm): 0.91-0.99: m: 4H, 1.77: m: 1H, 4.03: s: 3H, 4.18: s: 3H, 5.44: s: 2H, 7.47: m: 2H, 7.67-7.70: m: 2H, 7.90: d: 1H, 8.05: s: 1H, 8.29: s: 1H, 8.49: s: 1H.

EXAMPLE 12

Compound No. 12

3-(2,4-Dichlorophenyl)-1,9-dimethyl-6-(1,3-oxazol-4-yl)-1,9-dihydro-2H-pyrido[2,3-b]indol-2-one A solution of 0.1 g of the compound from preparation 1.2 in 1 ml of formamide is heated at 160° C. for 35 minutes. After cooling, the reaction mixture is poured into a saturated NaHCO3 solution, the product is extracted with DCM, the organic phase is dried over MgSO4, and the solvent is evaporated under vacuum. The residue is chromatographed on silica gel, elution being carried out with EtOAc. 0.042 g of the expected compound is obtained, Mp=221-222° C.

1H NMR: DMSO-d6 (300 MHz): δ (ppm): 4.01: s: 3H, 4.17: s: 3H, 7.43-7.50: m: 2H, 7.67-7.75: m: 3H, 8.25: s: 1H, 8.32: s: 1H, 8.47: d: 1H, 8.55: s: 1H.

EXAMPLE 13

Compound No. 13

3-(2,4-Dichlorophenyl)-1,9-dimethyl-6-(2-methyl-1,3-oxazol-4-yl)-1,9-dihydro-2H-pyrido[2,3-b]indol-2-one 0.22 g of acetamide is added to a solution of 0.3 g of the compound from preparation 1.2 in 2 ml of NMP and the mixture is heated at 150° C. for 30 minutes. After cooling, the mixture is extracted with EtOAc, the organic phase is washed with a saturated NH4Cl solution and with a 1N HCl solution and dried over Na2SO4, and the solvent is evaporated off under vacuum. The residue is chromatographed on silica gel, elution being carried out with the EtOAc/cyclohexane (90/10; v/v) mixture. 0.11 g of the expected compound is obtained, Mp=222-223° C.

1H NMR: DMSO-d6 (300 MHz): δ (ppm): 2.47: s: 3H, 4.01: s: 3H, 4.16: s: 3H, 7.46: m: 2H, 7.62-7.69: m: 3H, 8.25: s: 1H, 8.26: s: 1H, 8.38: s: 1H.

EXAMPLE 14

Compound No. 14

6-(2-Amino-1,3-oxazol-4-yl)-3-(2,4-dichlorophenyl)-1,9-dimethyl-1,9-dihydro-2H-pyrido[2,3-b]indol-2-one 0.22 g of urea is added to a solution of 0.3 g of the compound from preparation 1.2 in 2 ml of NMP and the mixture is heated at 150° C. for 30 minutes. After cooling, water is added and the precipitate formed is filter-dried. The precipitate dissolved in MeOH is chromatographed on silica gel, elution being carried out with the EtOAc/cyclohexane (75/25; v/v) mixture. 0.04 g of the expected compound is obtained, Mp=295-297° C.

1H NMR: DMSO-d6 (300 MHz): δ (ppm): 3.95: s: 3H, 4.10: s: 3H, 6.62: s: 2H, 7.37-7.43: m: 2H, 7.51: s: 2H, 7.63: s: 1H, 7.75: s: 1H, 8.06: s: 1H, 8.13: s: 1H.

EXAMPLE 15

Compound No. 15

3-(2,4-Dichlorophenyl)-6-[2-(hydroxymethyl)-1,3-oxazol-4-yl]-1,9-dimethyl-1,9-dihydro-2H-pyrido[2,3-b]indol-2-one 0.39 g of 2-(tetrahydro-2H-pyran-2-yloxy)acetamide is added to a solution of 0.2 g of the compound from preparation 1.2 in 2 ml of NMP and the mixture is heated at 150° C. for 1 hour 30 minutes. The reaction mixture is poured into water and the precipitate formed is filter-dried. The precipitate dissolved in an EtOAc/DCM mixture is chromatographed on silica gel, elution being carried out with EtOAc. The product obtained is taken up in the EtOAc/cyclohexane (10/90; v/v) mixture and the precipitate is filter-dried. 0.035 g of the expected compound is obtained.

1H NMR: DMSO-d6 (300 MHz): δ (ppm): 4.02: s: 3H, 4.18: s: 3H, 4.56: d: 2H, 5.72: t: 1H, 7.47: m: 1H, 7.69: m: 3H, 8.26: s: 1H, 8.30: s: 1H, 8.49: s: 1H.

EXAMPLE 16

Compound No. 16

3-(2,4-Dichlorophenyl)-6-[2-(ethoxymethyl)-1,3-oxazol-4-yl]-1,9-dimethyl-1,9-dihydro-2H-pyrido[2,3-b]indol-2-one 0.032 g of NaH at 60% in oil is added to a solution of 0.12 g of compound No. 15 in 4 ml of DMF and the mixture is left at AT for 30 minutes with stirring. 0.06 ml of iodoethane is subsequently added and the mixture is left at AT for 1 hour with stirring. The reaction mixture is poured into water, the mixture is extracted with EtOAc, the organic phase is washed with a saturated NH4Cl solution and dried over Na2SO4, and the solvent is evaporated off under vacuum. The residue is taken up in an EtOAc/PE (20/80; v/v) mixture and the precipitate formed is filter-dried. 0.07 g of the expected compound is obtained.

1H NMR: DMSO-d6 (300 MHz): δ (ppm): 1.15: t: 3H, 3.56: q: 2H, 4.02: s: 3H, 4.17: s: 3H, 4.58: s: 2H, 7.43-7.50: m: 2H, 7.67: m: 3H, 8.27: s: 1H, 8.31: s: 1H, 8.53: s: 1H.

EXAMPLE 17

Compound No. 17

[4-[3-(2,4-Dichlorophenyl)-1,9-dimethyl-2-oxo-2,9-dihydro-1H-pyrido[2,3-b]indol-6-yl]-1,3-oxazol-2-yl]methyl pivalate 0.14 ml of pivaloyl chloride is added to a solution of 0.1 g of compound No. 15 in 4 ml of pyridine and the mixture is left at AT for 2 hours with stirring. Water is added, the mixture is extracted with EtOAc, the organic phase is washed with a saturated NH4Cl solution and dried over Na2SO4, and the solvent is evaporated off under vacuum. The residue is chromatographed on silica gel, elution being carried out with the EtOAc/cyclohexane (75/25; v/v) mixture. The product obtained is taken up in an ether/PE mixture and the precipitate formed is filter-dried. 0.07 g of the expected compound is obtained.

1H NMR: DMSO-d6 (300 MHz): δ (ppm): 1.19: s: 9H, 4.02: s: 3H, 4.18: s: 3H, 5.24: s: 2H, 7.43-7.50: m: 2H, 7.69: s: 3H, 8.26: s: 1H, 8.56: s: 1H.

EXAMPLE 18

Compound No. 18

3-(2,4-Dichlorophenyl)-1,9-dimethyl-6-(2-methyl-1,3-oxazol-5-yl)-1,9-dihydro-2H-pyrido[2,3-b]indol-2-one A) 6-(Aminoacetyl)-3-(2,4-dichlorophenyl)-1,9-dimethyl-1,9-dihydro-2H-pyrido[2,3-b]indol-2-one hydrochloride This compound is prepared according to the procedure described in stage A of Example 5 using the compound from preparation 1.2.

B) 3-(2,4-Dichlorophenyl)-1,9-dimethyl-6-(2-methyl-1,3-oxazol-5-yl)-1,9-dihydro-2H-pyrido[2,3-b]indol-2-one This compound is prepared according to the procedure described in stage B of Example 5, Mp=239-240° C.

EXAMPLE 19

Compound No. 19

3-(2,4-Dichlorophenyl)-6-[2-(ethoxymethyl-1,3-oxazol-5-yl)-1,9-dimethyl-1,9-dihydro-2H-pyrido[2,3-b]indol-2-one A) N-[2-[3-(2,4-Dichlorophenyl)-1,9-dimethyl-2-oxo-2,9-dihydro-1H-pyrido[2,3-b]indol-6-yl]-2-oxoethyl]-2-ethoxyacetamide A mixture of 0.25 g of the compound from stage A of Example 18, 0.058 ml of ethoxyacetic acid, 0.318 g of PyBOP and 0.29 ml of DIPEA in 3 ml of DCM is left at AT for 16 hours with stirring. A saturated NH4Cl solution is added, the mixture is extracted with DCM, the organic phase is dried over MgSO4, and the solvent is evaporated off under vacuum. The residue is chromatographed on silica gel, elution being carried out with EtOAc and then with the EtOAc/MeOH (95/5; v/v) mixture. 0.268 g of the expected compound is obtained.

B) 3-(2,4-Dichlorophenyl)-6-[2-(ethoxymethyl-1,3-oxazol-5-yl)-1,9-dimethyl-1,9-dihydro-2H-pyrido[2,3-b]indol-2-one A solution of 0.268 g of the compound from the preceding stage in 0.5 ml of concentrated H2SO4 is left at AT for 20 hours with stirring. Water is added, the mixture is extracted with EtOAc, the organic phase is dried over MgSO4, and the solvent is evaporated off under vacuum. The product is chromatographed on silica gel, elution being carried out with the EtOAc/cyclohexane (50/50; v/v) mixture and then with EtOAc. 0.04 g of the expected compound is obtained, Mp=179-180° C.

EXAMPLE 20

Compound No. 20

6-(3-Amino-1H-pyrazol-5-yl)-3-(2,4-dichlorophenyl)-1,9-dimethyl-1,9-dihydro-2H-pyrido[2,3-b]indol-2-one A) 3-[3-(2,4-Dichlorophenyl)-1,9-dimethyl-2-oxo-2,9-dihydro-1H-pyrido[2,3-b]-indol-6-yl]-2-oxopropanenitrile 0.19 g of KCN is added to a solution of 0.7 g of the compound from preparation 1.2 in 11 ml of EtOH and 2 ml of water and the mixture is refluxed for 4 hours. The precipitate formed is filter-dried and dissolved in an MeOH/EtOAc mixture and the product is chromatographed on silica gel, elution being carried out with the EtOAc/cyclohexane (75/25; v/v) mixture and then with EtOAc. 0.2 g of the expected compound is obtained.

B) 6-(3-Amino-1H-pyrazol-5-yl)-3-(2,4-dichlorophenyl)-1,9-dimethyl-1,9-dihydro-2H-pyrido[2,3-b]indol-2-one 0.2 ml of hydrazine monohydrate is added to a solution of 0.2 g of the compound from the preceding stage in 10 ml of EtOH and the mixture is refluxed for 16 hours. The reaction mixture is chromatographed on silica gel, elution being carried out with EtOAc and then with the EtOAc/MeOH/NH3 (90/10/0.2; v/v/v) mixture. 0.05 g of the expected compound is obtained, Mp=284-286° C.

EXAMPLE 21

Compound No. 21

6-(2-Amino-1,3-thiazol-4-yl)-3-(2,4-dichlorophenyl)-1,9-dimethyl-1,9-dihydro-2H-pyrido[2,3-b]indol-2-one 0.053 g of thiourea is added to a solution of 0.25 g of the compound from preparation 1.3 in 12 ml of MeOH and the mixture is refluxed for 16 hours. The precipitate formed is filter-dried and washed with a saturated K2CO3 solution, with MeOH and with an EtOAc/PE (50/50; v/v) mixture. 0.18 g of the expected compound is obtained, Mp=272-273° C.

EXAMPLE 22

Compound No. 22

3-(2,4-Dichlorophenyl)-1-methyl-6-(1,3-thiazol-2-yl)-1,9-dihydro-2H-pyrido[2,3-b]indol-2-one 0.37 g of Cu2O is added to a solution of 0.25 g of the compound from preparation 1.4 in 10 ml of NMP, and then the reaction mixture is degassed for 10 minutes. 0.055 g of palladium(II) acetate, 0.2 g of 1,3-bis(diphenylphosphino)propane and 1 g of 2-(tributylstannyl)-1,3-thiazole are subsequently added, and then the mixture is heated at 100° C. for 16 hours. After cooling to AT, the reaction mixture is poured into a solution of AcOH at 30%, the mixture is extracted with EtOAc, the organic phase is dried over MgSO4, and the solvent is evaporated off under vacuum. The residue is chromatographed on silica gel, elution being carried out with EtOAc. The product obtained is taken up in EtOAc and the precipitate formed is filter-dried. 0.06 g of the expected compound is obtained.

1H NMR: DMSO-d6 (300 MHz): δ (ppm): 3.71: s: 3H, 7.46-7.88: m: 7H, 8.37: s: 1H, 8.50: s: 1H, 12.37: s: 1H.

EXAMPLE 23

Compound No. 23

3-(2,4-Dichlorophenyl)-1,9-dimethyl-6-(1,3-thiazol-2-yl)-1,9-dihydro-2H-pyrido[2,3-b]indol-2-one 0.25 g of compound No. 22 are added to a suspension of 0.35 g of NaH at 60% in oil, in 10 ml of DMF, and the mixture is left at AT, with stirring, until no more gas is given off. 0.07 ml of methyl iodide is subsequently added and the mixture is left at AT for 1 hour with stirring. Water is added, the mixture is extracted with EtOAc, the organic phase is dried over MgSO4, and the solvent is evaporated off under vacuum. The residue is chromatographed on silica gel, elution being carried out with EtOAc. The product obtained is taken up in an EtOAc/cyclohexane (25/75; v/v) mixture, and the precipitate formed is filter-dried and washed with PE.

1H NMR: DMSO-d6 (300 MHz): δ (ppm): 4.04: s: 3H, 4.20: s: 3H, 7.43-7.51: m: 2H, 7.69-7.75: m: 3H, 7.88-7.94: m: 2H, 8.41: s: 1H, 8.51: s: 1H.

EXAMPLE 24

Compound No. 24

3-(2,4-Dichlorophenyl)-1,9-dimethyl-6-(4-methyl-1,3-oxazol-2-yl)-1,9-dihydro-2H-pyrido[2,3-b]indol-2-one 10 ml of concentrated H2SO4 are cooled to −15° C., 0.6 g of the compound from preparation 1.5 and 0.092 ml of propargyl alcohol are added, and the mixture is left at 0° C. for 3 hours, with stirring, and then at AT overnight. The reaction mixture is poured into an ice/H2O mixture, Na2CO3 is added to a pH=7, the mixture is extracted with EtOAc, the organic phase is washed with a saturated NaCl solution and dried over MgSO4, and the solvent is evaporated off under vacuum. The residue is chromatographed on silica gel, elution being carried out with EtOAc and then with the EtOAc/MeOH (99/1; v/v) mixture. The product obtained is taken up in the propan-2-ol/PE (50/50; v/v) mixture and the precipitate formed is filter-dried. 0.015 g of the expected compound is obtained, Mp=258-261° C.

EXAMPLE 25

Compound No. 25

3-(2,4-Dichlorophenyl)-1,9-dimethyl-6-(4-methyl-1,3-thiazol-2-yl)-1,9-dihydro-2H-pyrido[2,3-b]indol-2-one A mixture of 0.2 g of the compound from preparation 1.6 and 3 ml of chloroacetone are heated at 80° C. overnight, in a sealed tube. After cooling to AT, the reaction mixture is poured into a saturated NaHCO3 solution, and the precipitate formed is filter-dried and washed with water then with the propan-2-ol/PE (50/50; v/v) mixture. 0.175 g of the expected compound is obtained, Mp=255-257° C.

EXAMPLE 26

Compound No. 26

6-(4-Amino-1,3-thiazol-2-yl)-3-(2,4-dichlorophenyl)-1,9-dimethyl-1,9-dihydro-2H-pyrido[2,3-b]indol-2-one A mixture of 0.2 g of the compound from preparation 1.6 and 0.04 ml of bromoacetonitrile in 5 ml of acetonitrile is refluxed overnight. After cooling to AT, MeOH is added and the mixture is concentrated under vacuum. The residue is chromatographed on silica gel, elution being carried out with the EtOAc/cyclohexane (90/10; v/v) mixture. The product obtained is taken up in a PE/MeOH/ether mixture and the precipitate formed is filter-dried. 0.06 g of the expected compound is obtained, Mp>300° C. (decomp.).

1H NMR: DMSO-d6 (300 MHz): δ (ppm): 4.02: s: 3H, 4.18: s: 3H, 5.39: s: 2H, 5.87: s: 1H, 7.43-7.50: m: 2H, 7.60-7.70: m: 3H, 8.35-8.39: m: 2H.

EXAMPLE 27

Compound No. 27

6-[4-(Chloromethyl)-1,3-thiazol-2-yl]-3-(2,4-dichlorophenyl)-1,9-dimethyl-1,9-dihydro-2H-pyrido[2,3-b]indol-2-one 0.073 g of 1,3-dichloroacetone is added to a suspension of 0.2 g of the compound from preparation 1.6 in 6 ml of 1,4-dioxane and the mixture is refluxed overnight. After cooling to AT, the mixture is concentrated under vacuum, the residue is taken up in water, then with an ether/MeOH (50/50; v/v) mixture, and with ether, and the precipitate formed is filter-dried. The precipitate is chromatographed on silica gel, elution being carried out with the DCM/MeOH (99/1; v/v) mixture. The product obtained is taken up in ether and filter-dried. 0.145 g of the expected compound is obtained, Mp=277-281° C. (decomp.).

EXAMPLE 28

Compound No. 28

6-[4-(Aminomethyl)-1,3-thiazol-2-yl]-3-(2,4-dichlorophenyl)-1,9-dimethyl-1,9-dihydro-2H-pyrido[2,3-b]indol-2-one A) 6-[4-(Azidomethyl)-1,3-thiazol-2-yl]-3-(2,4-dichlorophenyl)-1,9-dimethyl-1,9-dihydro-2H-pyrido[2,3-b]indol-2-one 0.16 g of NaN3 is added to a solution of 0.4 g of compound No. 27 in 15 ml of DMSO and the mixture is heated at 50° C. overnight. The reaction mixture is poured into water and the precipitate formed is filter-dried. The precipitate is taken up in an EtOAc/MeOH mixture and the solvents are concentrated under vacuum. The residue is triturated in an ether/MeOH mixture and the precipitate formed is filter-dried. 0.33 g of the expected compound is obtained.

B) 6-[4-(Aminomethyl)-1,3-thiazol-2-yl]-3-(2,4-dichlorophenyl)-1,9-dimethyl-1,9-dihydro-2H-pyrido[2,3-b]indol-2-one A mixture of 0.33 g of the compound from the preceding stage and 0.033 g of Pd/C at 10% in 10 ml of MeOH and 40 ml of acetic acid is hydrogenated for 24 hours, at AT and under a pressure of 4 bar. The catalyst is filtered off, and the filtrate is washed with MeOH and concentrated under vacuum. The residue is taken up with a saturated K2CO3 solution, the product is extracted with EtOAc, the organic phase is dried over Na2SO4, and the solvent is evaporated off under vacuum. The residue is chromatographed on silica gel, elution being carried out with the DCM/MeOH/triethylamine (95/5/1; v/v/v) mixture. The product obtained is triturated in ether and the precipitate formed is filter-dried. 0.12 g of the expected compound is obtained, Mp=261-266° C.

EXAMPLE 29

Compound No. 29

3-(2,4-Dichlorophenyl)-1,9-dimethyl-6-[4-(pyrrolidin-1-ylmethyl)-1,3-thiazol-2-yl]-1,9-dihydro-2H-pyrido[2,3-b]indol-2-one 0.068 g of K2CO3 and 0.021 ml of pyrrolidine are added to a solution of 0.1 g of compound No. 27 in 3 ml of DMF, and the mixture is heated at 80° C. overnight. After cooling to AT, the reaction mixture is poured into a 1 N HCl solution, the acidic aqueous phase is washed with EtOAc, basified by adding a 2N NaOH solution and extracted with EtOAc, the organic phase is dried over Na2SO4, and the solvent is evaporated off under vacuum. The residue is triturated in water, the precipitate formed is filter-dried and taken up in MeOH and the solvent is concentrated under vacuum. The residue is dissolved in an MeOH/pyridine mixture and the product is chromatographed on silica gel, elution being carried out with the EtOAc/MeOH/NH4OH 28% (89/10/1; v/v/v) mixture. The product obtained is triturated in ether and the precipitate formed is filter-dried. 0.03 g of the expected compound is obtained, Mp=222-226° C.

EXAMPLE 30

Compound No. 31

Methyl[2-[3-(2,4-dichlorophenyl)-1,9-dimethyl-2-oxo-2,9-dihydro-1H-pyrido[2,3-b]-indol-6-yl]-1,3-thiazol-4-yl]acetate 0.07 g of methyl 4-chloro-3-oxobutanoate is added to a suspension of 0.16 g of the compound from preparation 1.6 in 6 ml of 1,4-dioxane, and the mixture is refluxed overnight. After cooling to AT, the reaction mixture is concentrated under vacuum, the residue is triturated with water, then with a PE/propan-2-ol (50/50; v/v) mixture, then with an ether/MeOH (50/50; v/v) mixture, and then with ether, and the precipitate formed is filter-dried. 0.145 g of the expected compound is obtained, Mp=198-201° C.

EXAMPLE 31

Compound No. 32

[2-[3-(2,4-Dichlorophenyl)-1,9-dimethyl-2-oxo-2,9-dihydro-1H-pyrido[2,3-b]indol-6-yl]-1,3-thiazol-4-yl]acetic acid 0.168 g of lithium hydroxide monohydrate is added to a solution of 0.345 g of compound No. 31 in 10 ml of MeOH and 3.5 ml of water and the mixture is refluxed for 48 hours. After cooling to AT, the reaction mixture is poured into a 2N NaOH solution, the aqueous phase is washed with EtOAc, the product is acidified by adding a 6N HCl solution and extracted with EtOAc, the organic phase is dried over Na2SO4, and the solvent is evaporated off under vacuum. The residue is chromatographed on silica gel, elution being carried out with the EtOAc/MeOH/AcOH (94.5/5/0.5; v/v/v), then (89/10/1; v/v/v), mixture. 0.09 g of the expected compound is obtained, Mp=234-239° C.

EXAMPLE 32

Compound No. 33

3-(2,4-Dichlorophenyl)-1,9-dimethyl-6-(1,3-oxazol-5-yl)-1,9-dihydro-2H-pyrido[2,3-b]indol-2-one 0.073 g of 1-[(isocyanomethyl)sulphonyl]-4-methylbenzene and 0.062 g of K2CO3 are added to a solution of 0.145 g of the compound from preparation 1.7 in 4 ml of MeOH, and the mixture is then refluxed for 3 hours. The reaction mixture is concentrated under vacuum, the residue is taken up in water, and the precipitate formed is filter-dried and washed with water. The precipitate is chromatographed on silica gel, elution being carried out with the EtOAc/cyclohexane (80/20; v/v) mixture and then with EtOAc. The product obtained is taken up in an MeOH/DCM mixture, and the precipitate formed is filter-dried and washed with MeOH. 0.048 g of the expected compound is obtained, Mp=170-174° C.

EXAMPLE 33

Compound No. 34

6-(3-Amino-1H-pyrazol-4-yl)-3-(2,4-dichlorophenyl)-1,9-dimethyl-1,9-dihydro-2H-pyrido[2,3-b]indol-2-one 0.044 ml of hydrazine monohydrate and then 0.029 ml of acetic acid are added to a solution of 0.15 g of the compound from preparation 1.8 in 5 ml of MeOH, and the mixture is refluxed overnight. The reaction mixture is concentrated under vacuum, the residue is dissolved in a DCM/EtOAc mixture and the product is chromatographed on silica gel, elution being carried out with EtOAc, with the EtOAc/MeOH (95/5; v/v) mixture and then with the EtOAc/MeOH/triethylamine (90/10/2; v/v/v) mixture. The product obtained is triturated in ether and the precipitate formed is filter-dried. 0.05 g of the expected compound is obtained, Mp=240-245° C.

EXAMPLE 34

Compound No. 35

3-(2,4-Dichlorophenyl)-6-isoxazol-5-yl-1-methyl-1,9-dihydro-2H-pyrido[2,3-b]indol-2-one A) 3-(2,4-Dichlorophenyl)-6-isoxazol-5-yl-1-methyl-9-[[2-(trimethylsilyl)ethoxy]methyl]-1,9-dihydro-2H-pyrido[2,3-b]indol-2-one A solution of 0.236 g of the compound from preparation 1.9 and 0.043 g of hydroxylamine hydrochloride in 3 ml of MeOH is refluxed for 3 hours. After cooling to AT, PE is added, and the precipitate formed is filter-dried, washed with ether and dried. 0.147 g of the expected compound is obtained.

B) 3-(2,4-Dichlorophenyl)-6-isoxazol-5-yl-1-methyl-1,9-dihydro-2H-pyrido[2,3-b]-indol-2-one A mixture of 0.147 g of the compound from the preceding stage, 10 ml of 3M HCl and 5 ml of THF is heated at 100° C. for 3 days. After cooling to AT, the mixture is basified by adding a 1N NaOH solution and extracted with EtOAc, and the organic phase is concentrated under vacuum. The residue is chromatographed on silica gel, elution being carried out with the cyclohexane/EtOAc (50/50; v/v) mixture, with EtOAc, and then with the EtOAc/MeOH (95/5; v/v) mixture. The product obtained is taken up with MeOH, and the precipitate formed is filter-dried and washed with MeOH and with ether. 0.053 g of the expected compound is obtained, Mp=320-323° C.

EXAMPLE 35

Compound No. 36

3-(2,4-Dichlorophenyl)-1-methyl-6-(1H-pyrazol-5-yl)-1,9-dihydro-2H-pyrido[2,3-b]indol-2-one A) 3-(2,4-Dichlorophenyl)-1-methyl-6-(1H-pyrazol-5-yl)-9-[[2-(trimethylsilyl)ethoxy]methyl]-1,9-dihydro-2H-pyrido[2,3-b]indol-2-one A solution of 0.208 g of the compound from preparation 1.9 and 0.068 ml of hydrazine monohydrate in 4 ml of MeOH is refluxed for 24 hours. After cooling to AT, PE is added and the precipitate formed is filter-dried, washed with PE and dried. 0.149 g of the expected compound is obtained.

B) 3-(2,4-Dichlorophenyl)-1-methyl-6-(1H-pyrazol-5-yl)-1,9-dihydro-2H-pyrido-[2,3-b]indol-2-one A mixture of 0.098 g of the compound from the preceding stage, 6.7 ml of 3M HCl and 3.3 ml of THF is heated at 100° C. for 2 days. After cooling to AT, the solution is basified by adding a 1N NaOH solution, the product is extracted with EtOAc, and the organic phase is concentrated under vacuum. The residue is taken up with MeOH, and the precipitate formed is filter-dried and washed with MeOH and then with ether. 0.02 g of the expected compound is obtained, Mp=246-250° C.

EXAMPLE 36

Compound No. 37

3-(2,4-Dichlorophenyl)-1-methyl-6-(1-methyl-1H-pyrazol-3-yl)-1,9-dihydro-2H-pyrido[2,3-b]indol-2-one A) 3-(2,4-Dichlorophenyl)-1-methyl-6-(1-methyl-1H-pyrazol-3-yl)-9-[[2-(trimethylsilyl)ethoxy]methyl]-1,9-dihydro-2H-pyrido[2,3-b]indol-2-one 0.011 g of NaH at 60% in oil and then 0.017 ml of iodomethane are added to a solution of 0.099 g of the compound from stage A of Example 35 in 2 ml of DMF, and the mixture is left at AT overnight with stirring. A saturated NaHCO3 solution is added, the mixture is extracted with EtOAc, the organic phase is dried over MgSO4, and the solvent is evaporated off under vacuum. The residue is chromatographed on silica gel, elution being carried out with the EtOAc/cyclohexane (60/40; v/v) mixture and then EtOAc. 0.111 g of the expected compound is obtained.

B) 3-(2,4-Dichlorophenyl)-1-methyl-6-(1-methyl-1H-pyrazol-3-yl)-1,9-dihydro-2H-pyrido[2,3-b]indol-2-one A mixture of 0.111 g of the compound from the preceding stage, 7.4 ml of 3M HCl and 3.7 ml of THF is heated at 100°

C. for 4 days. After cooling to AT, the mixture is basified by adding 1N NaOH, the product is extracted with EtOAc, the organic phase is dried over MgSO4, and the solvent is evaporated off under vacuum. The residue is chromatographed on silica gel, elution being carried out with the EtOAc/cyclohexane (80/20; v/v) mixture and then with EtOAc. 0.028 g of the expected compound is obtained.

1H NMR: DMSO-d6 (400 MHz): 3.7 s: 3H, 3.95: s: 3H, 6.65: s: 1H; 7.40-7.50: m: 2H, 7.55-7.70: m: 3H, 7.75: d: 1H; 8.15: s: 1H; 8.25: s: 1H; 10.70: bs: 1H.

EXAMPLE 37

Compound No. 38

3-(2,4-Dichlorophenyl)-6-(1-ethyl-1H-pyrazol-5-yl)-1-methyl-1,9-dihydro-2H-pyrido[2,3-b]indol-2-one A) 3-(2,4-Dichlorophenyl)-6-(1-ethyl-1H-pyrazol-5-yl)-1-methyl-9-[[2-(trimethylsilyl)ethoxy]methyl]-1,9-dihydro-2H-pyrido[2,3-b]indol-2-one A solution of 0.15 g of the compound from preparation 1.9 and 0.118 g of ethylhydrazine oxalate in 5 ml of MeOH is refluxed overnight. After cooling to AT, a saturated NaHCO3 solution is added, the mixture is extracted with DCM, the organic phase is dried over MgSO4, and the solvent is evaporated off under vacuum. 0.158 g of the expected compound is obtained.

B) 3-(2,4-Dichlorophenyl)-6-(1-ethyl-1H-pyrazol-5-yl)-1-methyl-1,9-dihydro-2H-pyrido[2,3-b]indol-2-one A mixture of 0.158 g of the compound from the preceding stage, 10 ml of 3M HCl and 5 ml of THF is heated at 100° C. for 3 days. After cooling to AT, the mixture is basified by adding 1N NaOH, the product is extracted with EtOAc, the organic phase is dried over MgSO4, and the solvent is evaporated off under vacuum. The residue is chromatographed on silica gel, elution being carried out with the EtOAc/cyclohexane (80/20; v/v) mixture. The product obtained is taken up in MeOH and left to crystallize overnight. The crystalline product formed is filter-dried, and washed with MeOH and then ether. 0.045 g of the expected compound is obtained, Mp=255-258° C.

EXAMPLE 38

Compound No. 39

3-(2,4-Dichlorophenyl)-6-isoxazol-5-yl-1,9-dimethyl-1,9-dihydro-2H-pyrido[2,3-b]indol-2-one A mixture of 0.221 g of the compound from preparation 1.10, 0.042 ml of acetic acid and 0.051 g of hydroxylamine hydrochloride in 3 ml of MeOH is left at AT for 48 hours with stirring. The mixture is concentrated under vacuum, the residue is extracted with DCM, the organic phase is washed with an NaHCO3 solution, with water and with a saturated NaCl solution, the product is dried over MgSO4, and the solvent is evaporated off under vacuum. The residue is chromatographed on silica gel, elution being carried out with EtOAc. The product obtained is triturated in an MeOH/DCM/EtOAc mixture and the precipitate formed is filter-dried, Mp=241-242° C.

EXAMPLE 39

Compound No. 40

3-(2,4-Dichlorophenyl)-1,9-dimethyl-6-(1H-pyrazol-5-yl)-1,9-dihydro-2H-pyrido[2,3-b]indol-2-one A mixture of 0.114 g of the compound from preparation 1.10, 0.021 ml of acetic acid and 0.018 ml of hydrazine monohydrate in 1 ml of MeOH is left at AT for 48 hours with stirring. The mixture is concentrated under vacuum, the residue is extracted with DCM, the organic phase is washed with a saturated NaHCO3 solution, with water and with a saturated NaCl solution, the product is dried over MgSO4, and the solvent is evaporated off under vacuum. The residue is chromatographed onto silica gel, elution being carried out with EtOAc. The product obtained is triturated in MeOH and the precipitate formed is filter-dried. 0.027 g of the expected compound is obtained, Mp=281-282° C.

EXAMPLE 40

Compound No. 41

3-(2,4-Dichlorophenyl)-1,9-dimethyl-6-(1-methyl-1H-pyrazol-3-yl)-1,9-dihydro-2H-pyrido[2,3-b]indol-2-one 0.033 g of NaH at 60% in oil is added to a solution of 0.23 g of compound No. 40 in 8 ml of DMF, and the mixture is left at AT for 5 minutes with stirring. 0.051 ml of iodomethane is subsequently added and the mixture is left at AT overnight with stirring. A saturated NaHCO3 solution is added, the mixture is extracted with EtOAc, the organic phase is dried over MgSO4, and the solvent is evaporated off under vacuum. The residue is chromatographed on silica gel, elution being carried out with EtOAc. The product obtained is taken up in MeOH and the precipitate formed is filter-dried and washed with MeOH and then with ether. 0.103 g of the expected compound is obtained.

1H NMR: DMSO-d6 (300 MHz): δ (ppm): 3.88: s: 3H, 4.01: s: 3H, 4.19: s: 3H, 6.68: d: 1H; 7.46: m: 2H, 7.61: m: 1H; 7.71: m: 3H, 8.28: s: 2H.

EXAMPLE 41

Compound No. 42

3-(2,4-Dichlorophenyl)-6-(1-ethyl-1H-pyrazol-3-yl)-1,9-dimethyl-1,9-dihydro-2H-pyrido[2,3-b]indol-2-one 0.033 g of NaH at 60% in oil is added to a solution of 0.23 g of compound No. 40 in 8 ml of DMF, and the mixture is left at AT for 5 minutes with stirring. 0.065 ml of iodoethane is subsequently added and the mixture is left at AT overnight with stirring. A saturated NaHCO3 solution is added, the mixture is extracted with EtOAc, the organic phase is dried over MgSO4, and the solvent is evaporated off under vacuum. The residue is chromatographed on silica gel, elution being carried out with EtOAc. The product obtained is taken up in MeOH and the precipitate formed is filter-dried and washed with MeOH and then with ether.

1H NMR: DMSO-d6 (300 MHz): δ (ppm): 1.41: t: 3H, 4.02: s: 3H, 4.16: m: 5H, 6.68: d: 1H; 7.46: m: 2H, 7.61: d: 1H; 7.68: d: 1H; 7.76: m: 2H, 8.29: d: 2H.

EXAMPLE 42

Compound No. 43

3-(2,4-Dichlorophenyl)-1,9-dimethyl-6-(1,3-oxazol-2-yl)-1,9-dihydro-2H-pyrido[2,3-b]indol-2-one A mixture of 0.2 g of the compound from preparation 1.11, 0.047 g of 1,3-dioxol-2-one and 1 g of $H_3PO_4$ is heated at 170° C. overnight. After cooling to AT, water and EtOAc are added and the mixture is left to stir for 10 minutes. After separation by settling out, the organic phase is dried over MgSO4, and the solvent is evaporated off under vacuum. The residue is chromatographed on silica gel, elution being carried out with EtOAc. 0.062 g of the expected compound is obtained, Mp=232-233° C.

EXAMPLE 43

Compound No. 44

Methyl 5-[3-(2,4-dichlorophenyl)-1,9-dimethyl-2-oxo-2,9-dihydro-1H-pyrido[2,3-b]indol-6-yl]-1H-pyrazole-3-carboxylate A) 5-[3-(2,4-Dichlorophenyl)-1,9-dimethyl-2-oxo-2,9-dihydro-1H-pyrido[2,3-b]indol-6-yl]-1H-pyrazole-3-carboxylic acid 0.04 ml of hydrazine monohydrate is added to a solution of 0.364 g of the compound from preparation 1.12 in 10 ml of EtOH and the mixture is then refluxed for 5 hours. The reaction mixture is concentrated under vacuum and the residue is chromatographed on silica gel, elution being carried out with EtOAc and then with the gradient of the mixture EtOAc/MeOH/triethylamine (45/45/10; v/v/v). 0.27 g of the expected compound is obtained, which compound is used as it is.

B) Methyl 5-[3-(2,4-dichlorophenyl)-1,9-dimethyl-2-oxo-2,9-dihydro-1H-pyrido[2,3-b]indol-6-yl]-1H-pyrazole-3-carboxylate 0.1 ml of H2SO4 is added to a solution of 0.27 g of the compound from the preceding stage in 5 ml of MeOH and the mixture is refluxed for 12 hours. The reaction mixture is concentrated under vacuum, the residue is taken up in a pyridine/MeOH mixture, the product is triturated, and the insoluble material is filter-dried and washed with MeOH. The filtrate is chromatographed on silica gel, elution being carried out with EtOAc. 0.068 g of the expected compound is obtained, Mp=290-292° C.

EXAMPLE 44

Compound No. 45

Methyl 5-[3-(2,4-dichlorophenyl)-1,9-dimethyl-2-oxo-2,9-dihydro-1H-pyrido[2,3-b]indol-6-yl]isoxazole-3-carboxylate 0.156 g of hydroxylamine hydrochloride is added to a solution of 0.364 g of the compound from preparation 1.12 in 5 ml of MeOH, and the mixture is then refluxed for 4 hours. The reaction mixture is concentrated under vacuum and the residue is chromatographed on silica gel, elution being carried out with EtOAc. The residue is taken up with MeOH, and the precipitate formed is filter-dried and washed with MeOH and then with ether. 0.037 g of the expected compound is obtained, Mp=280-281° C.

EXAMPLE 45

Compound No. 46

3-(2,4-Dichlorophenyl)-1,9-dimethyl-6-(4-methyl-isoxazol-5-yl)-1,9-dihydro-2H-pyrido[2,3-b]indol-2-one 0.09 g of hydroxylamine hydrochloride is added to a suspension of 0.3 g of the compound from preparation 1.13 in 7 ml of MeOH and the mixture is left at AT for 48 hours with stirring. The precipitate formed is filter-dried and washed with a cyclohexane/EtOAc (75/25; v/v) mixture. 0.25 g of the expected compound is obtained, Mp=233-234° C.

EXAMPLE 46

Compound No. 47

3-(2,4-Dichlorophenyl)-1,9-dimethyl-6-(3-methyl-1H-pyrazol-5-yl)-1,9-dihydro-2H-pyrido[2,3-b]indol-2-one A solution of 0.12 g of the compound from preparation 1.14 and 0.109 g of hydrazine monohydrate in 3 ml of MeOH is left at AT overnight with stirring. The reaction mixture is dissolved by adding DCM and MeOH and the product is chromatographed on silica gel, elution being carried out with EtOAc and then with the EtOAc/MeOH (95/5; v/v) mixture. 0.09 g of the expected compound is obtained, Mp=309-310° C.

EXAMPLE 47

Compound No. 48

3-(2,4-Dichlorophenyl)-1,9-dimethyl-6-(1H-1,2,3-triazol-4-yl)-1,9-dihydro-2H-pyrido[2,3-b]indol-2-one A mixture of 0.178 g of the compound from preparation 1.15, 0.410 g of NaN3 and 0.337 g of NH4Cl in 5 ml of DMF is heated in a microwave at 190° C. for 30 minutes. A saturated NaHCO3 solution is added, the mixture is extracted with EtOAc, the organic phase is dried over MgSO4, and the solvent is evaporated off under vacuum. The residue is chromatographed on silica gel, elution being carried out with the EtOAc/cyclohexane (70/30; v/v) mixture. The product obtained is taken up in a DCM/MeOH mixture and the precipitate formed is filter-dried. 0.031 g of the expected compound is obtained, Mp=274-275° C.

EXAMPLE 48

Compound No. 49

6-(5-Amino-1,3,4-thiadiazol-2yl)-3-(2,4-dichlorophenyl)-1,9-dimethyl-1,9-dihydro-2H-pyrido[2,3-b]indol-2-one 0.15 g of hydrazine carbothioamide is added to a solution of 0.6 g of the compound from preparation 1.16 in 6 ml of POCl3 and the mixture is refluxed for 3 hours. The reaction mixture is cooled, water is added dropwise until a precipitate forms, and then this is refluxed for 2 hours. After cooling to AT, the mixture is basified by adding 1 N NaOH, the precipitate formed is filter-dried and taken up in a DCM/MeOH mixture, and the product is chromatographed on silica gel, elution being carried out with the EtOAc/MeOH/NH4OH (95/5/0.5; v/v/v) mixture. 0.065 g of the expected compound is obtained, Mp=321-323° C.

EXAMPLE 49

Compound No. 50

3-(2,4-Dichlorophenyl)-1,9-dimethyl-6-(5-methyl-1, 3-oxazol-2-yl)-1,9-dihydro-2H-pyrido[2,3-b]indol-2-one A mixture of 0.21 g of the compound from preparation 1.17, 0.017 g of mercury acetate and 5.5 ml of acetic acid is heated at 120° C. for 4 hours. The mixture is concentrated under vacuum, the residue is taken up with a saturated K2CO3 solution, the product is extracted with DCM, the organic phase is dried over MgSO4 and the solvent is evaporated off under vacuum. The residue is chromatographed on silica gel, elution being carried out with EtOAc and then with the EtOAc/MeOH (99/1; v/v) mixture. The product obtained is triturated in MeOH and the precipitate formed is filter-dried. 0.076 g of the expected compound is obtained, Mp=289-292° C.

EXAMPLE 50

Compose No. 30: Compound 30 of the table is prepared as indicated for Example 29

EXAMPLE 51

3-(2,4-Dichlorophenyl)-6-[1-(2-hydroxyethyl)-1H-pyrazol-3-yl]-1,9-dimethyl-1,9-dihydropyrido[2,3-b]indol-2-one A) compound A: 3-(2,4-Dichlorophenyl)-1,9-dimethyl-6-{1-[2-(tetrahydropyran-2-yloxy)ethyl]-1H-pyrazol-3-yl}-1,9-dihydropyrido[2,3-b]indol-2-one The process is carried out as indicated in Example 36 above, using 3-(2,4-dichlorophenyl)-1,9-dimethyl-6-(5-methyl-2H-pyrazol-3-yl)-1,9-dihydropyrido[2,3-b]indol-2-one described in Example 39 and 2-(2-bromoethoxy)tetrahydropyran (Collect. Czech. Chem. Commun.; EN; 69; 10; 2004; 1843-1876).

1H NMR DMSO d6 (300 MHz): 1.30-1.51 (m, 4H); 1.51-1.75 (m, 2H); 3.60 (m, 1H); 3.78 (m, 1H); 3.95-4.10 (m, 4H); 4.15 (s, 3H); 4.20 (s, 1H); 4.32 (m, 2H); 4.56 (m, 1H); 7.40-7.50 (m, 3H); 7.57-7.65 (d, J=8.63, 1H); 7.70 (d, J=1.69, 1H); 7.75-7.85 (m, 2H); 8.29 (m, 2H).

B) 3-(2,4-Dichlorophenyl)-6-[1-(2-hydroxyethyl)-1H-pyrazol-3-yl]-1,9-dimethyl-1,9-dihydropyrido[2, 3-b]indol-2-one A solution containing 311 mg (0.56 mmol) of compound A 3-(2,4-dichlorophenyl)-1,9-dimethyl-6-{1-[2-(tetrahydropyran-2-yloxy)ethyl]-1H-pyrazol-3-yl}-1,9-dihydropyrido[2, 3-b]indol-2-one, 2.7 ml of acetic acid, 1.3 ml of THF and 0.7 ml of H2O is heated at 45° C. for 16 h. The reaction medium is allowed to cool, adsorbed onto silica and purified by flash chromatography, elution being carried out with EtOAc/20% cyclohexane, then 100% EtOAc, and, finally, EtOAc/5% MeOH. The residue is taken up in MeOH and the product is filtered and then washed with MeOH.

147 mg of white powder are obtained.
Mp: 239-240° C.
1H NMR DMSO d6 (300 MHz): 3.80 (d, J=5.08, 2H); 4.02 (s, 3H); 4.19 (m, 5H); 4.95 (m, 1H); 6.70 (d, J=2.16, 1H); 7.46 (m, 2H); 7.62 (d, J=8.64, 1H); 7.70 (d, J=1.62, 1H); 7.71-7.81 (m, 2H); 8.30 (s, 2H).

EXAMPLE 52

3-(2,4-Dichlorophenyl)-6-(2-ethyl-4-methyl-2H-pyrazol-3-yl)-1,9-dimethyl-1,9-dihydropyrido[2,3-b]indol-2-one The process is carried out as indicated in Example 37 above, using 3-(2,4-dichlorophenyl)-6-(3-dimethylamino-2-methylacryloyl)-1,9-dimethyl-1,9-dihydropyrido[2,3-b]indol-2-one from preparation 1.13 above and ethylhydrazine oxalate.

1H NMR DMSO d6 (300 MHz): 1.20 (t, J=7.1, 3H); 1.94 (s, 3H); 3.97-7.04 (m, 5H); 4.20 (s, 3H); 7.25 (d, J=8.4, 1H); 7.35 (s, 1H); 7.42-7.49 (m, 2H); 7.69 (s, 1H); 7.74 (d, J=8.4, 1H); 7.91 (s, 1H); 8.32 (s, 1H).

EXAMPLE 53

3-(2,4-Dichlorophenyl)-1,9-dimethyl-6-(4-methyl-2H-pyrazol-3-yl)-1,9-dihydropyrido[2,3-b]indol-2-one The process is carried out as indicated in Example 40 above, using 3-(2,4-dichlorophenyl)-6-(3-dimethylamino-2-methylacryloyl)-1,9-dimethyl-1,9-dihydropyrido[2,3-b]indol-2-one from preparation 1.13 above and hydrazine hydrate.

1H NMR DMSO d6 (300 MHz): 2.23 (s, 3H); 4.03 (s, 3H); 4.18 (s, 3H); 7.43-7.57 (m, 4H); 7.67-7.70 (m, 2H); 8.09 (s, 1H); 8.31 (s, 1H); 12 67 (s, 1H).

EXAMPLE 54

3-(2,4-Dichlorophenyl)-1,9-dimethyl-6-(3-methyl-isoxazol-5-yl)-1,9-dihydropyrido[2,3-b]indol-2-one The process is carried out as indicated in Example 44 above, using 1-[3-(2,4-dichlorophenyl)-1,9-dimethyl-2-oxo-2,9-dihydro-1H-pyrido[2,3-b]indol-6-yl]butane-1,3-dione from preparation 1.14 and hydroxylamine hydrochloride.
Mp: 288-289° C.
1H NMR DMSO d6 (300 MHz): 2.29 (s, 3H); 4.02 (s, 3H); 4.20 (s, 3H); 6.80 (s, 1H); 7.40-7.51 (m, 2H); 7.70 (d, J=1.93, 1H); 7.75 (d, J=1.69, 2H); 8.34 (s, 1H); 8.42 (s, 1H).

EXAMPLE 55

6-(5-Aminoisoxazol-3-yl)-3-(2,4-dichlorophenyl)-1, 9-dimethyl-1,9-dihydropyrido[2,3-b]indol-2-one A solution containing 300 mg (0.707 mmol) of compound 3-[3-(2,4-dichlorophenyl)-1,9-dimethyl-2-oxo-2,9-dihydro-1H-pyrido[2,3-b]indol-6-yl]-3-oxopropionitrile from Example 20A, 238 mg (2.9 mmol) of sodium acetate and 152 mg (2.2 mmol) of hydroxylamide hydrochloride in 4 ml of $CH_2Cl_2$ and 4 ml of MeOH is stirred at 50° C. for 24 h and then at ambient temperature for 18 h. The reaction medium is concentrated by adsorbing it onto silica, and purification is carried out on a silica column, elution being carried out with EtOAc/20% cyclohexane and then 100% EtOAc.

67 mg of beige powder are obtained.

Mp: 234-235° C.

1H NMR DMSO d6 (300 MHz): 4.01 (s, 3H); 4.18 (s, 3H); 5.44 (s, 1H); 6.74 (s, 2H); 7.40-7.50 (m, 2H); 7.68 (m, 3H); 8.27 (s, 1H); 8.31 (s, 1H).

EXAMPLE 56

3-(2,4-Dichlorophenyl)-6-(2-ethoxymethyloxazol-5-yl)-1-methyl-1,9-dihydropyrido[2,3-b]indol-2-one A) Compound A: N-{2-[3-(2,4-Dichlorophenyl)-1-methyl-2-oxo-2,9-dihydro-1H-pyrido[2,3-b]indol-6-yl]-2-oxoethyl}-2-ethoxyacetamide 756 mg (1.73 mmol) of compound 6-(aminoacetyl)-3-(2,4-dichlorophenyl)-1-methyl-1,9-dihydro-2H-pyrido[2,3-b]indol-2-one hydrochloride from Example 5A above, 180 µl (1.90 mmol) of ethoxyacetic acid, 991 mg (1.90 mmol) of PyBOP and 905 µl (5.2 mmol) of diisopropylethylamine are dissolved in 9 ml of CH2Cl2. The mixture is stirred at ambient temperature for 16 h. A saturated solution of NH4Cl is added and the mixture is extracted with CH2Cl2, dried over MgSO4, filtered and concentrated under vacuum. The product is purified by chromatography on a silica column, elution being carried out with EtOAc and then EtOAc/3% MeOH.

841 mg of a brown oil are obtained.

1H NMR DMSO d6 (300 MHz): 1.17-1.35 (m, 3H); 3.58 (m, 2H); 3.70 (s, 3H); 3.94 (s, 2H); 4.74 (d, J=5.34, 2H); 7.40-7.52 (m, 2H); 7.59 (d, J=8.54, 1H); 7.70 (s, 1H); 7.90 (d, J=8.51, 1H); 7.95 (m, 1H); 8.37 (s, 1H); 8.71 (s, 1H).

B) 3-(2,4-Dichlorophenyl)-6-(2-ethoxymethyloxazol-5-yl)-1-methyl-1,9-dihydropyrido[2,3-b]indol-2-one A solution of compound A N-{2-[3-(2,4-dichlorophenyl)-1-methyl-2-oxo-2,9-dihydro-1H-pyrido[2,3-b]indol-6-yl]-2-oxoethyl}-2-ethoxyacetamide (841 mg, 1.73 mmol) in 2 ml of H2SO4 is stirred at ambient temperature for 20 h. H2O is added, the mixture ie extracted with EtOAc and CH2Cl2, and the product is concentrated without drying. The product is adsorbed onto silica and purification is carried out by chromatography on a silica column, elution being carried out with EtOAc. The residue is taken up in Et$_2$O, and the product is filtered and washed with a minimum amount of Et$_2$O.

372 mg of beige powder are obtained.

Mp: decomp. 320° C.

1H NMR DMSO d6 (300 MHz): 1.16 (t, J=6.99, 3H); 3.52-3.62 (q, J=3.72, 2H); 3.70 (s, 3H); 4.58 (s, 2H); 7.40-7.50 (m, 2H); 7.55 (m, 1H); 7.58 (m, 2H); 7.70 (d, J=1.62, 1H); 8.26 (s, 1H); 8.30 (s, 1H); 12.35 (s, 1H).

EXAMPLE 57

3-(2,4-Dichlorophenyl)-6-(1,5-dimethyl-1H-pyrazol-3-yl)-1,9-dimethyl-1,9-dihydropyrido[2,3-b]indol-2-one The process is carried out as in Example 36 above, using 3-(2,4-dichlorophenyl)-1,9-dimethyl-6-(3-methyl-1H-pyrazol-5-yl)-1,9-dihydro-2H-pyrido[2,3-b]indol-2-one described in Example 46 above and iodomethane.

Mp: 286-287° C.

1H NMR DMSO d6 (300 MHz): 2.28 (s, 3H); 3.75 (s, 3H); 4.00 (s, 3H); 4.15 (s, 3H); 6.47 (s, 1H); 7.40-7.50 (m, 2H); 7.58 (d, J=8.61, 1H); 7.69 (m, 2H); 8.23 (d, J=1.24, 1H); 8.27 (s, 1H).

EXAMPLE 58

3-(2,4-Dichlorophenyl)-6-(1-ethyl-5-methyl-1H-pyrazol-3-yl)-1,9-dimethyl-1,9-dihydropyrido[2,3-b]indol-2-one The process is carried out as indicated in Example 36 above, using 3-(2,4-dichlorophenyl)-1,9-dimethyl-6-(3-methyl-1H-pyrazol-5-yl)-1,9-dihydro-2H-pyrido[2,3-b]indol-2-one described in Example 46 above and iodoethane.

Mp: 270-272° C.

1H NMR DMSO d6 (300 MHz): 1.21-1.40 (2t, J=7.18, 3H); 2.20-2.32 (2s, 3H); 4.00 (s, 3H); 4.10 (q, J=7.20, 2H); 4.15 (s, 3H); 6.11-6.46 (2s, 1H); 7.42 (m, 2H); 7.60 (d, J=8.62, 1H); 7.70 (2d, J=1.65, 2H); 8.20-8.40 (m, 2H).

EXAMPLE 59

5-[3-(2,4-Dichlorophenyl)-1,9-dimethyl-2-oxo-2,9-dihydro-1H-pyrido[2,3-b]indol-6-yl]-1-ethyl-1H-pyrazole-3-carboxylic acid ethyl ester A) Compound A: 4-[3-(2,4-Dichlorophenyl)-1,9-dimethyl-2-oxo-2,9-dihydro-1H-pyrido[2,3-b]indol-6-yl]-2,4-dioxobutyric acid ethyl ester 940 mg (6.4 mmol) of diethyl oxalate are dissolved in 5 ml of anhydrous THF. 273 mg (6.8 mmol) of 60% NaH are added and the mixture is stirred at ambient temperature for 10 minutes. A solution of 1.3 g (3.2 mmol) of compound 6-(bromoacetyl)-3-(2,4-dichlorophenyl)-1,9-dimethyl-1,9-dihydro-2H-pyrido[2,3-b]indol-2-one from preparation 1.2 above and 18 mg (0.052 mmol) of dibenzo-18-crown-6 dissolved in 20 ml of anhydrous THF is added, as are a few drops of anhydrous EtOH. The mixture is heated at 70° C. under argon for 3 hours. The mixture is allowed to return to ambient temperature. EtOAc is added to the reaction medium and the organic phase is washed with a 1N HCl solution. The organic phase is evaporated to dryness and the product obtained is triturated in water and filtered. The product is taken up in EtOH and evaporated to dryness.

1.85 g of orange powder are obtained.

1H NMR DMSO d6 (300 MHz): 1.32 (t, J=7.08, 3H); 4.03 (s, 3H), 4.21 (s, 3H); 4.29-4.36 (q, J=7.07, 2H); 7.30 (s, 1H), 7.43-7.52 (m, 2H); 7.71 (s, 1H); 7.80 (d, J=8.85, 1H); 8.00-8.04 (sd, J=1.74, J=8.77, 1H); 8.48 (s, 1H); 8.83 (s, 1H).

B) 5-[3-(2,4-Dichlorophenyl)-1,9-dimethyl-2-oxo-2,9-dihydro-1H-pyrido[2,3-b]indol-6-yl]-1-ethyl-1H-pyrazole-3-carboxylic acid ethyl ester 930 mg (1.85 mmol) of compound A 4-[3-(2,4-dichlorophenyl)-1,9-dimethyl-2-oxo-2,9-dihydro-1H-pyrido[2,3-b]indol-6-yl]-2,4-dioxobutyric acid ethyl ester are dissolved in 20 ml of absolute ethanol. 583 mg (5.56 mmol) of ethylhydrazine oxalate are added and the mixture is refluxed overnight. The reaction medium is evaporated to dryness and the residue is triturated in a saturated K2CO3 solution. The product is filtered and washed with water. Purification is carried out on a silica column, elution being carried out with EtOAc.

510 mg of white foam are obtained.

1H NMR DMSO d6 (300 MHz): 1.28-1.33 (m, 6H); 4.03 (s, 3H); 4.18-4.32 (m, 7H), 6.83 (s, 1H); 7.39-7.50 (m, 3H); 7.69 (d, J=1.93, 1H); 7.76 (d, J=8.57, 1H); 8.07 (d, J=1.33, 1H); 8.32 (s, 1H).

EXAMPLE 60

3-(4-Bromophenyl)-1,9-dimethyl-6-(2H-pyrazol-3-yl)-1,9-dihydropyrido[2,3-b]indol-2-one A) Compound A: 3-(4-Bromophenyl)-1,9-dimethyl-1,9-dihydro-1H-pyrido[2,3-b]indol-2-one The process is carried out as indicated in preparation 1.2B above, with methyl-(1-methyl-1H-indol-2-yl)amine hydrochloride (prepared according to the procedures described in WO 2004/041817) and 3-dimethylamino-2-(4-bromophenyl)acrylic acid methyl ester from preparation 2.10 WO 2005/108398.

1H NMR DMSO d6 (300 MHz): 4.01 (s, 3H); 4.12 (s, 3H); 7.24 (m, 2H); 7.58 (m, 3H); 7.75 (sd, J=1.91, J=6.69, 2H); 7.93 (d, J=7.24, 1H); 8.45 (s, 1H).

B) Compound B: 6-Acetyl-3-(4-bromophenyl)-1,9-dimethyl-1,9-dihydropyrido[2,3-b]indol-2-one The process is carried out as indicated in preparation 1.9A above, with the compound A 3-(4-bromophenyl)-1,9-dimethyl-1,9-dihydro-1H-pyrido[2,3-b]indol-2-one and acetyl chloride 1H NMR DMSO d6 (300 MHz): 2.65 (s, 3H); 4.03 (s, 3H); 4.18 (s, 3H); 7.59 (d, J=8.61, 2H); 7.69-7.72 (d, J=8.71, 1H); 7.79 (d, J=8.62, 2H); 7.90 (sd, J=1.70, J=8.67, 1H); 8.65 (s, 1H); 8.69 (d, J=1.51, 1H).

C) Compound C: 3-(4-bromophenyl)-6-(3-dimethylaminoacryloyl)-1,9-dimethyl-1,9-dihydropyrido[2,3-b]indol-2-one The process is carried out as indicated in preparation 1.9C above with compound B 6-acetyl-3-(4-bromophenyl)-1,9-dimethyl-1,9-dihydropyrido[2,3-b]indol-2-one and Bredereck's reagent.

1H NMR DMSO d6 (300 MHz): 2.96 (bs, 3H); 3.14 (bs, 3H); 4.02 (s, 3H); 4.17 (s, 3H); 6.00 (d, J=12.27, 1H); 7.60 (t, J=9.11, 3H); 7.72 (d, J=12.25, 1H); 7.79 (d, J=6.71, 2H); 7.89 (sd, J=1.61, J=8.64, 1H); 8.57 (d, J=1.34, 1H); 8.59 (s, 1H).

D) 3-(4-Bromophenyl)-1,9-dimethyl-6-(2H-pyrazol-3-yl)-1,9-dihydropyrido[2,3-b]indol-2-one The process is carried out as indicated in Example 36 above, with compound 3-(4-bromophenyl)-6-(3-dimethylaminoacryloyl)-1,9-dimethyl-1,9-dihydropyrido[2,3-b]indol-2-one and hydrazine monohydrate.

Mp: 347° C.

1H NMR DMSO d6 (300 MHz): 4.01 (s, 3H); 4.12 (s, 3H); 6.74 (m, 1H); 7.54-7.80 (m, 7H); 8.39-8.54 (m, 2H); 12.80 (s, 1H).

EXAMPLE 61

3-(2,4-Dichlorophenyl)-6-(2-ethyl-5-hydroxymethyl-2H-pyrazol-3-yl) 1,9-dimethyl-1,9-dihydropyrido[2,3-b]indol-2-one 450 mg (0.86 mmol) of compound from Example 59, 5-[3-(2,4-dichlorophenyl)-1,9-dimethyl-2-oxo-2,9-dihydro-1H-pyrido[2,3-b]indol-6-yl]-1-ethyl-1H-pyrazole-3-carboxylic acid ethyl ester, are dissolved in 10 ml of absolute ethanol and 42 mg (1.12 mmol) of NaBH4 are added. The mixture is refluxed overnight. The reaction medium is allowed to return to ambient temperature, CH2Cl2 and MeOH are added, and the product is adsorbed onto silica. Purification is carried out on a silica column, elution being carried our with EtOAc, and then with a 95/05 EtOAc/MeOH mixture. The oil obtained is triturated in ether.

50 mg of white powder are obtained.

Mp: 235° C.

1H NMR DMSO d6 (300 MHz): 1.27 (t, J=7.13, 3H); 4.03 (s, 3H); 4.05-4.13 (q, J=7.18, 2H); 4.20 (s, 3H); 4.42 (d, J=5.43, 2H); 5.03 (t, J=5.68, 1H); 6.27 (s, 1H); 7.33 (sd, J=1.63, J=8.46, 1H); 7.42-7.50 (m, 2H); 7.69 (d, J=1.95, 1H); 7.73 (d, J=8.55, 1H); 7.98 (d, J=1.40, 1H); 8.32 (s, 1H);

EXAMPLE 62

3-(2,4-Dichlorophenyl)-6-(thiazol-4-yl)-1,9-dimethyl-1,9-dihydropyrido[2,3-b]indol-2-one 150 mg (0.3 mmol) of compound 3-(2,4-dichlorophenyl)-6-[2-(hydroxymethyl)-1,3-thiazol-4-yl]-1,9-dimethyl-1,9-dihydro-2H-pyrido[2,3-b]indol-2-one from Example 9 above are dissolved in 10 ml of DMF. 50 mg of 60% NaH (0.96 mmol) are added and the mixture is stirred at ambient temperature for 30 min. 0.05 ml (0.6 mmol) of cyclopropyl bromide are added and the mixture is then stirred at ambient temperature for 3 hours. Water is added and the mixture is extracted with EtOAc. The product is washed with a saturated NaCl solution followed by adsorption onto silica. Purification is carried out by chromatography on a silica column, elution being carried out with EtOAc.

60 mg of white powder are obtained.

Mp: 289° C.

MS: 440.08

1H NMR DMSO d6 (300 MHz): 4.02 (s, 3H); 4.18 (s, 3H); 7.46 (m, 2H); 7.69 (m, 2H); 7.96 (d, J=8.6, 1H); 8.06 (s, 1H); 8.28 (s, 1H); 8.53 (s, 1H); 9.20 (s, 1H).

EXAMPLE 63

3-(4-Fluorophenyl)-6-(2-hydroxymethylthiazol-4-yl)-1,9-dimethyl-1,9-dihydropyrido[2,3-b]indol-2-one A) Compound A: 3-(4-Fluorophenyl)-1,9-dimethyl-1,9-dihydropyrido[2,3-b]indol-2-one The process is carried out as indicated in preparation 1.2B above, with methyl-(1-methyl-1H-indol-2-yl)amine hydrochloride (prepared according to the procedures described in WO 2004/041817) and 2-(4-fluorophenyl)-3-dimethylaminoacrylic acid methyl ester, preparation 2.12 WO5108398

B) Compound B: 6-(2-Bromoacetyl)-3-(4-fluorophenyl)-1,9-dimethyl-1,9-dihydropyrido[2,3-b]indol-2-one The process is carried out as indicated in preparation 1.1E above, with compound A 3-(4-fluorophenyl)-1,9-dimethyl-1,9-dihydropyrido[2,3-b]indol-2-one and bromo-acetyl chloride.

C) Compound C: 2,2-Dimethylpropionic acid 4-[3-(4-fluorophenyl)-1,9-dimethyl-2-oxo-2,9-dihydro-1H-pyrido[2,3-b]indol-6-yl]-thiazol-2-ylmethyl ester The process is carried out as indicated in Example 3 above, with compound B 6-(2-bromoacetyl)-3-(4-fluorophenyl)-1,9-dimethyl-1,9-dihydropyrido[2,3-b]indol-2-one and 2-amino-2-thioxoethyl pivalate
1H NMR DMSO-d6 (300 MHz): 1.16 (s, 3H); 1.22 (s, 6H); 4.01 (s, 3H); 4.15 (s, 3H); 5.46 (s, 2H); 7.16-7.26 (t, J=8.96, 2H); 7.63 (d, J=8.67, 1H); 7.78-7.90 (m, 3H); 8.05 (s, 1H); 8.48 (s, 1H); 8.53 (d, J=1.48, 1H).

D) 3-(4-Fluorophenyl)-6-(2-hydroxymethylthiazol-4-yl)-1,9-dimethyl-1,9-dihydropyrido[2,3-b]indol-2-one The process is carried out as indicated in Example 3 above, with compound C 2,2-dimethylpropionic acid 4-[3-(4-fluorophenyl)-1,9-dimethyl-2-oxo-2,9-dihydro-1H-pyrido[2,3-b]indol-6-yl]-thiazol-2-ylmethyl ester
Mp: 162-166° C.
1H NMR DMSO-d6 (300 MHz): 4.01 (s, 3H); 4.15 (s, 3H); 4.82 (s, 2H); 7.16-7.28 (t, J=8.96, 2H); 7.63 (d, J=8.64, 1H); 7.80-7.90 (m, 3H); 7.94 (s, 1H); 8.48 (s, 1H); 8.52 (d, J=1.45).

EXAMPLE 64

3-(2,4-Dichlorophenyl)-6-(2-hydroxymethyloxazol-5-yl)-1,9-dimethyl-1,9-dihydropyrido[2,3-b]indol-2-one A) Compound A: 2-Benzyloxy-N-{2-[3-(2,4-dichlorophenyl)-1,9-dimethyl-2-oxo-2,9-dihydro-1H-pyrido[2,3-b]indol-6-yl]-2-oxoethyl}acetamide 500 mg (1.11 mmol) of 6-(aminoacetyl)-3-(2,4-dichlorophenyl)-1,9-dimethyl-1,9-dihydro-2H-pyrido[2,3-b]indol-2-one, hydrochloride described in Example 18A above, 175 μL (1.22 mmol) of benzyloxyacetic acid, 635 mg (1.22 mmol) of PyBop and 580 μL (3.33 mmol) of diisopropylethylamine are dissolved in 6 ml of CH$_2$Cl$_2$. The mixture is stirred at ambient temperature for 16 h. A saturated NH$_4$CL solution is added, the mixture is then extracted with CH$_2$CL$_2$ and the organic phase is dried over MgSO$_4$, filtered and concentrated under vacuum. Purification is carried out on a silica column, elution being carried out with EtOAc and then with EtOAc/5% MeOH. 454 mg of yellow crystals are obtained.

B) 3-(2,4-Dichlorophenyl)-6-(2-hydroxymethyloxazol-5-yl)-1,9-dimethyl-1,9-dihydropyrido[2,3-b]indol-2-one A solution of compound A 2-benzyloxy-N-{2-[3-(2,4-dichlorophenyl)-1,9-dimethyl-2-oxo-2,9-dihydro-1H-pyrido[2,3-b]indol-6-yl]-2-oxoethyl}acetamide (454 mg, 0.81 mmol) in 2 ml of H2SO4 is stirred at ambient temperature for 20 h. A mixture of H2O and EtOAc is added, the green solid obtained is filtered off, the filtrate is taken up and extracted with EtOAc, and these combined organic phases are concentrated with the precipitate without drying. The product is adsorbed onto silica with a minimum amount of pyridine and purification is carried out by chromatography on a silica column, elution being carried out with EtOAc and then EtOAc/5% MeOH. The residue is taken up in MeOH and the product is filtered and washed with a minimum amount of MeOH and then of Et2O.

221 mg of beige powder are obtained.
Mp: 296-297° C.
1H NMR DMSO-d6 (300 MHz): 4.01 (s, 3H); 4.18 (s, 3H); 4.54 (bs, 2H); 5.70 (bs, 1H); 7.40-7.48 (m, 2H); 7.52 (m, 1H); 7.60-7.76 (m, 3H); 8.25 (s, 1H); 8.31 (s, 1H).

EXAMPLE 65

3-(2-Chloro-4-hydroxyphenyl)-1,9-dimethyl-6-(2H-pyrazol-3-yl)-1,9-dihydropyrido[2,3-b]indol-2-one A) Compound A: 3-(2-Chloro-4-fluorophenyl)-1,9-dimethyl-1,9-dihydropyrido[2,3-b]indol-2-one The process is carried out as indicated in Example 60 above, using 3-dimethylamino-2-(2-chloro-4-fluorophenyl) acrylic acid methyl ester.
1H NMR DMSO-d6 (300 MHz): 3.99 (s, 3H); 4.13 (s, 3H); 7.15-7.35 (m, 3H); 7.40-7.55 (m, 2H); 7.55-7.64 (d, J=8.10, 1H); 7.82-7.90 (d, J=7.4, 1H); 8.19 (s, 1H).

B) Compound B: 3-(2-Chloro-4-methoxy-phenyl)-1,9-dimethyl-1,9-dihydropyrido[2,3-b]indol-2-one 3.25 g (81.1 mmol) of 60% NaH are added to 300 ml of DMF and 9.6 ml of MeOH. The mixture is left to stir for 5 minutes, and then 9.22 g (27.0 mmol) of compound A 3-(2-chloro-4-fluorophenyl)-1,9-dimethyl-1,9-dihydropyrido[2,3-b]indol-2-one are added. The mixture is stirred at ambient temperature and then, as soon as no more gas is being given off, is heated at 80° C. for 16 h. The reaction medium is left to cool and poured into H2O, the yellow precipitate is filtered off and washed with H2O, the residue is taken up in MeOH and the product is concentrated to dryness.
10.6 g of yellow powder are obtained.
1H NMR DMSO-d6 (300 MHz): 3.81 (s, 3H); 4.00 (s, 3H); 4.15 (s, 3H); 6.95 (sd, J=8.53; j=2.1, 1H); 7.10 (d, J=2.57, 1H); 7.17-7.26 (m, 1H); 7.27-7.32 (m, 2H); 7.60 (d, J=8.06, 1H); 7.87 (d, J=6.97, 1H); 8.14 (s, 1H).

C) Compound C: 6-Acetyl-3-(2-chloro-4-methoxyphenyl)-1,9-dimethyl-1,9-dihydropyrido[2,3-b]indol-2-one The process is carried out as indicated in Example 60 above, using compound B: 3-(2-chloro-4-methoxyphenyl)-1,9-dimethyl-1,9-dihydropyrido[2,3-b]indol-2-one and acetyl chloride.

D) Compound D: 3-(2-Chloro-4-methoxyphenyl)-6-(3-dimethylaminoacryloyl)-1,9-dimethyl-1,9-dihydropyrido[2,3-b]indol-2-one The process is carried out as indicated in Example 60 above, using compound C$_3$-(2-chloro-4-methoxyphenyl)-6-(3-dimethylaminoacryloyl)-1,9-dimethyl-1,9-dihydropyrido[2,3-b]indol-2-one and Bredereck's reagent.

E) Compound E: 3-(2-Chloro-4-methoxyphenyl)-1,9-dimethyl-6-(2H-pyrazol-3-yl)-1,9-dihydropyrido[2,3-b]indol-2-one The process is carried out as indicated in Example 60 above, using compound D 3-(2-chloro-4-methoxyphenyl)-6-(3-dimethylaminoacryloyl)-1,9-dimethyl-1,9-dihydropyrido[2,3-b]indol-2-one and hydrazine hydrate.

F) 3-(2-Chloro-4-hydroxyphenyl)-1,9-dimethyl-6-(2H-pyrazol-3-yl)-1,9-dihydro-pyrido[2,3-b]indol-2-one At −78° C., a 1M solution of BBr3 in CH2Cl2 (2.19 ml, 2.19 mmol) is added to a solution of compound E 3-(2-chloro-4-methoxyphenyl)-1,9-dimethyl-6-(2H-pyrazol-3-yl)-1,9-dihydropyrido[2,3-b]indol-2-one (306 mg, 0.73 mmol) in 3 ml of CH2Cl2. The mixture is stirred at AT for 16 h. H2O is added and the precipitate is filtered off. The solid is taken up in MeOH/CH2Cl2 and the product is adsorbed onto silica. Purification is carried out by column chromatography, elution being carried out with CH2Cl2/5% MeOH. The residue is taken up with MeOH, and the product is washed and filtered with MeOH.

199 mg of white powder are obtained.
Mp: 319-320° C.
1H NMR DMSO-d6 (300 MHz): 4.00 (s, 3H); 4.16 (s, 3H); 6.70 (bs, 1H); 6.75-6.82 (sd, J=8.35, j=2.42, 1H); 6.90 (d, J=2.39, 1H); 7.20 (d, J=8.36, 1H); 7.45-7.82 (m, 3H); 8.05-8.20 (m, 1H); 8.30 (bs, 1H); 9.88 (bs, 1H).

EXAMPLE 66

3-(2,4-Dichlorophenyl)-6-(1-methoxymethyl-1H-pyrazol-3-yl)-1,9-dimethyl-1,9-dihydropyrido[2,3-b]indol-2-one The process is carried out as indicated in Example 36 above, using 3-(2,4-dichlorophenyl)-1,9-dimethyl-6-(1H-pyrazol-5-yl)-1,9-dihydro-2H-pyrido[2,3-b]indol-2-one from Example 39 above and bromomethyl methyl ether.

Mp: 232-234° C.
1H NMR DMSO-d6 (300 MHz): 3.28 (s, 3H); 4.01 (s, 3H); 4.16 (s, 3H); 5.40 (s, 2H); 6.81 (d, J=2.34, 1H); 7.41-7.51 (m, 2H); 7.60-7.71 (m, 2H); 7.80 (sd, 1H); 7.94 (d, J=2.34, 1H); 8.28 (s, 1H); 8.34 (d, 1H).

EXAMPLE 67

3-(2,4-Dichlorophenyl)-6-[1-(2-methoxyethyl)-1H-pyrazol-3-yl]-1,9-dimethyl-1,9-dihydropyrido[2,3-b]indol-2-one The process is carried out as in Example 10 above, using 3-(2,4-dichlorophenyl)-6-[1-(2-hydroxyethyl)-1H-pyrazol-3-yl]-1,9-dimethyl-1,9-dihydropyrido[2,3-b]indol-2-one from Example 51 and iodomethane.

Mp: 206-208° C.
1H NMR DMSO-d6 (300 MHz): 3.25 (s, 3H); 3.70-3.79 (t, J=5.31, 2H); 4.01 (s, 3H); 4.16 (s, 3H); 4.24-4.32 (t, J=5.26, 2H); 6.68 (d, J=2.25, 1H); 7.40-7.50 (m, 2H); 7.59-7.64 (d, J=8.62, 1H); 7.69 (d, J=1.65, 1H); 7.73-7.81 (m, 1H); 8.29 (d, J=2.56, 2H).

EXAMPLE 68

3-(4-Bromophenyl)-6-(2-ethyl-2H-pyrazol-3-yl)-1,9-dimethyl-1,9-dihydropyrido[2,3-b]indol-2-one The process is carried out as in Example 37 above, with the compound from Example 60C3-(4-bromophenyl)-6-(3-dimethylaminoacryloyl)-1,9-dimethyl-1,9-dihydropyrido[2,3-b]indole-2-one and ethylhydrazine oxalate.

1H NMR DMSO d6 (300 MHz): 1.29 (t, J=7.20, 3H); 4.03 (s, 3H); 4.18 (m, 5H); 6.36 (s, 1H); 7.35 (sd, J=1.71, J=8.47, 1H); 7.50 (d, J=1.86, 1H); 7.59 (m, 2H); 7.78 (m, 3H); 8.07 (d, J=1.53, 1H); 8.57 (s, 1H).
Mp: 200-203° C.

EXAMPLE 69

6-(2-Ethoxymethylthiazol-4-yl)-3-(4-fluorophenyl)-1,9-dimethyl-1,9-dihydropyrido[2,3-b]indol-2-one The process is carried out as in Example 10 above, using 3-(4-fluorophenyl)-6-(2-hydroxymethylthiazol-4-yl)-1,9-dimethyl-1,9-dihydropyrido[2,3-b]indol-2-one, compound from Example 63 and iodoethane.

Mp: 86° C.-90° C.
MS: 448.15
1H NMR DMSO-d6 (300 MHz): 1.21 (t, J=6.98, 3H); 3.60-3.70 (q, J=7.0, 2H); 4.02 (s, 3H); 4.15 (s, 3H); 4.82 (s, 2H); 7.18-7.28 (t, J=8.96, 2H); 7.64 (d, J=8.62, 1H); 7.80-7.92 (m, 3H); 8.00 (s, 1H); 8.48 (s, 1H); 8.52 (d, J=1.33, 1H).

EXAMPLE 70

2,2-Dimethylpropionic acid 4-[3-(4-fluorophenyl)-1,9-dimethyl-2-oxo-2,9-dihydro-1H-pyrido[2,3-b]indol-6-yl]thiazol-2-ylmethyl ester 200 mg (0.48 mmol) of compound 3-(4-fluorophenyl)-6-(2-hydroxymethylthiazol-4-yl)-1,9-dimethyl-1,9-dihydropyrido[2,3-b]indol-2-one from Example 63 are dissolved in 3 ml of pyridine. 294 µl (2.38 mmol) of pivaloyl chloride are added and the mixture is then stirred at ambient temperature for 2 hours. H2O is added, the mixture is extracted with EtOAc, the organic phase is washed with a saturated NH4Cl solution and then dried over MgSO4, and the product is filtered and concentrated. Purification is carried out by chromatography on a silica gel column, elution being carried out with EtOAc.

209 mg of yellow powder are obtained.
Mp: 90° C.-92° C.
MS: 504.19
1H NMR DMSO-d6 (300 MHz): 1.23 (s, 9H); 4.02 (s, 3H); 4.15 (s, 3H); 5.47 (s, 2H); 7.18-7.29 (t, J=8.95, 2H); 7.65 (d, J=8.67, 1H); 7.80-7.92 (m, 3H); 8.05 (s, 1H); 8.48 (s, 1H); 8.53 (d, J=1.41, 1H).

EXAMPLE 71

3-(4-Fluorophenyl)-1,9-dimethyl-6-thiazol-4-yl-1,9-dihydropyrido[2,3-b]indol-2-one The process is carried out as in Example 62 above, with the compound from Example 63, 3-(4-fluorophenyl)-6-(2-hydroxymethylthiazol-4-yl)-1,9-dimethyl-1,9-dihydropyrido[2,3-b]indol-2-one.

Mp: 280° C.-282° C.
MS: 390.13
1H NMR DMSO-d6 (300 MHz): 4.02 (s, 3H); 4.16 (s, 3H); 7.15-7.30 (t, J=8.72, 2H); 7.66 (d, J=8.53, 1H); 7.76-7.89 (q, J=5.95, 2H); 7.94 (d, J=8.33, 1H); 8.08 (s, 1H); 8.49 (s, 1H); 8.59 (s, 1H); 9.21 (s, 1H).

EXAMPLE 72

3-(4-Fluorophenyl)-1,9-dimethyl-6-(2H-pyrazol-3-yl)-1,9-dihydropyrido[2,3-b]indol-2-one A) Compound A: 6-Acetyl-3-(4-fluorophenyl)-1,9-dimethyl-1,9-dihydropyrido[2,3-b]indol-2-one The process is carried out as in preparation 1.9B above, using 3-(4-fluorophenyl)-1,9-dimethyl-1,9-dihydropyrido[2,3-b]indol-2-one from Example 63A above and acetyl chloride.

1H NMR DMSO d6 (300 MHz): 2.64 (s, 3H); 4.01 (s, 3H); 4.16 (s, 3H); 7.24 (t, J=8.9, 2H); 7.67 (d; J=8.7, 1H); 7.80-7.89 (m, 3H); 8.57 (s, 1H); 8.66 (s, 1H).

B) Compound B: 6-(3-Dimethylaminoacryloyl)-3-(4-fluorophenyl)-1,9-dimethyl-1,9-dihydropyrido[2,3-b]indol-2-one The process is carried out as in preparation 1.9C above, using compound A, 6-acetyl-3-(4-fluorophenyl)-1,9-dimethyl-1,9-dihydropyrido[2,3-b]indol-2-one.
1H NMR DMSO d6 (300 MHz): 2.95 (s, 3H); 3.14 (s, 3H); 4.01 (s, 3H); 4.15 (s, 3H); 6.00 (d, J=12.3, 1H); 7.23 (t, J=8.9, 2H); 7.59 (d, J=8.7, 1H); 7.72 (d, J=12.3, 1H); 7.80-7.95 (m, 3H); 8.55 (s, 1H); 8.56 (s, 1H).

C) 3-(4-Fluorophenyl)-1,9-dimethyl-6-(2H-pyrazol-3-yl)-1,9-dihydropyrido[2,3-b]indol-2-one The process is carried out as in Example 40 above, using compound B 6-(3-dimethylaminoacryloyl)-3-(4-fluorophenyl)-1,9-dimethyl-1,9-dihydropyrido[2,3-b]indol-2-one and hydrazine hydrate.
Mp: 318°
1H NMR DMSO d6 (300 MHz): 4.02 (s, 3H); 4.14 (s, 3H); 6.75 (s, 1H); 7.23 (m, 2H); 7.61-7.83 (m, 5H); 8.40 (s, 1H); 8.49 (s, 1H); 8.80 (s, 1H).

EXAMPLE 73

3-(2,4-Dichlorophenyl)-1,9-dimethyl-6-[1-(2-morpholin-4-ylethyl)-1H-pyrazol-3-yl]-1,9-dihydropyrido[2,3-b]indol-2-one The process is carried out as in Example 36, using compound 3-(2,4-dichlorophenyl)-1,9-dimethyl-6-(1H-pyrazol-5-yl)-1,9-dihydro-2H-pyrido[2,3-b]indol-2-one from Example 39 above and chloroethylmorpholine
1H NMR CHCl3-d (300 MHz): 2.49-2.52 (m, 4H); 2.87 (t, J=6.4, 2H); 3.69-3.72 (m, 4H); 4.06 (s, 3H); 4.11 (s, 3H); 4.30 (t, J=6.6, 2H); 6.57 (s, 1H); 7.30 (d, J=2.0, 1H); 7.36 (t, J=8.2, 2H); 7.49-7.52 (m, 2H); 7.76 (sd, J=1.6, J=8.5, 1H); 8.04 (s, 1H); 8.16 (d, J=1.3, 1H).

EXAMPLE 74

3-(2,4-Dichlorophenyl)-1,9-dimethyl-6-[1-(2-pyrrolidin-1-ylethyl)-1H-pyrazol-3-yl]-1,9-dihydropyrido[2,3-b]indol-2-one The process is carried out as in Example 73 above, using chloroethylpyrrolidine.
1H NMR CHCl3-d (300 MHz): 1.76-1.80 (m, 4H); 2.54-2.58 (m, 4H); 3.00 (t, J=7.0, 2H); 4.06 (s, 3H); 4.10 (s, 3H); 4.32 (t, J=7.0, 2H); 6.57 (s, 1H); 7.30 (d, J=2.1, 1H); 7.36 (t, J=8.2, 2H); 7.50 (s, 2H); 7.76 (sd, J=1.6, J=8.5, 1H); 8.04 (s, 1H); 8.16 (d, J=1.3, 1H).

EXAMPLE 75

6-(4-Aminomethylthiazol-2-yl)-3-(4-bromophenyl)-1,9-dimethyl-1,9-dihydropyrido[2,3-b]indol-2-one A) Compound A: 3-(4-Bromophenyl)-6-(4-chloromethylthiazol-2-yl)-1,9-dimethyl-1,9-dihydropyrido[2,3-b]indol-2-one 3.3 g (7.7 mmol) of 3-(4-bromophenyl)-1,9-dimethyl-2-oxo-2,9-dihydro-1H-pyrido[2,3-b]indole-6-carbothioic acid amide [prepared according to preparation 1.6 above (1H NMR DMSO-d6 (300 MHz): 4.03 (s, 3H); 4.20 (s, 3H); 7.60 (m, 3H); 7.77 (m, 2H); 7.90 (d, J=1.8, 1H); 8.48 (s, 1H); 8.58 (s, 1H); 9.42 (s, 1H), 9.75 (s, 1H))], are dissolved in 40 ml of dioxane.
1.2 g (9.3 mmol) of dichloroacetone are added. The mixture is refluxed overnight. The mixture is allowed to return to ambient temperature. Methanol and EtOAc are added to the reaction medium and the mixture is adsorbed onto silica. Purification is carried out on a silica column, elution being carried out with a 99/01 CH2Cl2/MeOH mixture.
2.5 g of yellow powder are obtained.
1H NMR DMSO-d6 (300 MHz): 4.03 (s, 3H); 4.18 (s, 3H); 4.89 (s, 2H); 7.58 (d, J=8.4, 2H); 7.80 (m, 5H), 8.58 (d, J=1.5, 1H); 8.71 (s, 1H).

B) Compound B: 6-(4-Azidomethylthiazol-2-yl)-3-(4-bromophenyl)-1,9-dimethyl-1,9-dihydropyrido[2,3-b]indol-2-one 400 mg (0.8 mmol) of compound A, 3-(4-bromophenyl)-6-(4-chloromethylthiazol-2-yl)-1,9-dimethyl-1,9-dihydropyrido[2,3-b]indol-2-one, are dissolved in 10 ml of DMSO. 160 mg (2.4 mmol) of NaN3 are added. The mixture is heated at 45° C. overnight. The mixture is allowed to return to ambient temperature. The reaction medium is poured into water, and the precipitate is filtered off and washed with water. The product is taken up in ethanol and evaporated to dryness.
370 mg of yellow powder are obtained.
MS: 504.96

C): 6-(4-Aminomethylthiazol-2-yl)-3-(4-bromophenyl)-1,9-dimethyl-1,9-dihydropyrido[2,3-b]indol-2-one 370 mg (0.73 mmol) of compound B 6-(4-azidomethylthiazol-2-yl)-3-(4-bromophenyl)-1,9-dimethyl-1,9-dihydropyrido[2,3-b]indol-2-one are dissolved in 40 ml of methanol and 40 ml of glacial acetic acid. 40 mg of Pd/C are added. The mixture is hydrogenated under 60 psi at 25° C. for 48 hours. The reaction medium is filtered over celite. Washing is carried out with ethanol. The filtrate is evaporated to dryness. The residue is dissolved in a CH2Cl2/MeOH mixture and the product is adsorbed onto silica. Purification is carried out on a silica column, elution being carried out with 97/02/01 CH2Cl2/MeOH/NH4OH and then with 93/05/02 CH2Cl2/MeOH/NH4OH.
110 mg of pale yellow powder are obtained.
1H NMR DMSO-d6 (300 MHz): 1.94 (bs, 2H); 3.86 (s, 2H); 4.03 (s, 3H); 4.17 (s, 3H); 7.78 (s, 1H); 7.58 (d, J=8.7, 2H); 7.70 (d, J=8.7, 1H); 7.85 (m, 3H); 8.56 (s, 1H); 8.70 (s, 1H).

EXAMPLE 76

3-(4-Bromophenyl)-6-(1-ethyl-1H-pyrazol-3-yl)-1,9-dimethyl-1,9-dihydropyrido[2,3-b]indol-2-one The process is carried out as indicated in Example 36 above, using 3-(4-bromophenyl)-1,9-dimethyl-6-(2H-pyrazol-3-yl)-1,9-dihydropyrido[2,3-b]indol-2-one from Example 60 above and iodoethane.
1H NMR DMSO-d6 (300 MHz): 1.29/1.43 (t, m/M, J=7.2, 3H); 4.03 (s, 3H); 4.18 (m, 5H); 6.34/6.71 (d, m/M, J=2.1, 1H); 7.60 (m, 3H); 7.80 (m, 4H); 8.07/8.37 (s, m/M, 1H); 8.57 (s, 1H).

EXAMPLE 77

6-(2-Aminothiazol-5-yl)-3-(2-chloro-4-fluorophenyl)-1,9-dimethyl-1,9-dihydropyrido[2,3-b]indol-2-one The process is carried out as indicated in Example 21 above, using 6-(2-bromoacetyl)-3-(2-chloro-4-fluorophenyl)-1,9-dimethyl-1,9-dihydropyrido[2,3-b]indol-2-one [prepared according to preparation 1.1 above using the compound from Example 65A above, 3-(2-chloro-4-fluorophenyl)-1,9-dimethyl-1,9-dihydropyrido[2,3-b]indol-2-one] and thiourea.

Mp: 294° C.-295° C.
MS: 438.8
1H NMR DMSO-d6 (300 MHz): 4.00 (s, 3H); 4.14 (s, 3H); 6.89 (s, 1H); 6.99 (s, 2H); 7.22-7.29 (st, J=8.4, J=2.7, 1H); 7.43-7.59 (m, 2H); 7.57 (d, J=8.7, 1H); 7.73-7.77 (sd, J=8.4, J=1.5, 1H); 8.17 (s, 1H); 8.27 (d, J=1.5, 1H).

EXAMPLE 78

6-(2-Aminomethylthiazol-4-yl)-3-(4-bromophenyl)-1,9-dimethyl-1,9-dihydropyrido[2,3-b]indol-2-one

A) Compound A: {4-[3-(4-Bromophenyl)-1,9-dimethyl-2-oxo-2,9-dihydro-1H-pyrido[2,3-b]indol-6-yl]thiazol-2-ylmethyl}carbamic acid benzyl ester The process is carried out as indicated in Example 3 above, using 6-(2-bromoacetyl)-3-(4-bromophenyl)-1,9-dimethyl-1,9-dihydropyrido[2,3-b]indol-2-one [prepared according to preparation 1.1 above using 3-(4-bromophenyl)-1,9-dimethyl-1,9-dihydropyrido[2,3-b]indol-2-one, 1H NMR DMSO-d6 (300 MHz): 3.97 (s, 3H); 4.17 (s, 3H); 4.93 (s, 2H); 7.56 (sd, J=6.9, J=2.1, 2H); 7.70-7.81 (m, 3H); 7.90-7.98 (m, 1H); 8.58 (s, 1H); 8.71 (d, J=1.5, 1H)] and N-benzyloxycarbonyl glycine thioamide Mp: 238-240° C.
MS: 613.18
1H NMR DMSO-d6 (300 MHz): 4.01 (s, 3H); 4.15 (s, 3H); 4.57 (d, J=6.3, 2H); 5.11 (s, 2H); 7.20-7.41 (m, 5H); 7.52-7.68 (m, 3H); 7.75-7.82 (m, 2H); 7.87 (d, J=8.7, 1H); 7.93 (s, 1H); 8.28 (t, J=6.0, 1H); 8.52 (s, 2H).

B): 6-(2-Aminomethylthiazol-4-yl)-3-(4-bromophenyl)-1,9-dimethyl-1,9-dihydro-pyrido[2,3-b]indol-2-one A solution of compound A {4-[3-(4-bromophenyl)-1,9-dimethyl-2-oxo-2,9-dihydro-1H-pyrido[2,3-b]indol-6-yl]thiazol-2-ylmethyl}carbamic acid benzyl ester (200 mg, 0.32 mmol) and thioanisole (308 μl, 2.60 mmol) in 2 ml of TFA is left to stir overnight at ambient temperature. H2O is added, the mixture is extracted with EtOAc, the organic phases are washed with H2O and the product is dried over MgSO$_4$, filtered and concentrated. Purification is carried out by chromatography on a silica column, elution being carried out with 100% EtOAc and then with an EtOAc/5% MeOH mixture then with an EtOAc/5% MeOH/1% TEA mixture. The residue is taken up in a 1/1 EtOAc/Et2O mixture and the product is filtered and washed with a minimum amount of Et2O.

82 mg of a yellowish-ochre powder are obtained.
Mp: 195° C.-201° C.
MS: 480.8
1H NMR DMSO-d6 (300 MHz): 4.00 (s, 3H); 4.14 (s, 3H); 4.41 (s, 2H); 7.57 (d, J=8.1, 2H); 7.66 (d, J=8.7, 1H); 7.74 (d, J=8.1, 2H); 7.80-7.98 (m, 3H); 8.04 (s, 1H); 8.42 (s, 1H); 8.54 (s, 1H).

EXAMPLE 79

3-(2,4-Dichlorophenyl)-6-(2-ethyl-2H-pyrazol-3-yl)-1,9-dimethyl-1,9-dihydropyrido[2,3-b]indol-2-one The process is carried out as in Example 37 above, with the compound from preparation 1.13B, 3-(2,4-dichlorophenyl)-6-[3-(dimethylamino)prop-2-enoyl]-1,9-dimethyl-1,9-dihydro-2H-pyrido[2,3-b]indol-2-one Mp: 232° C.-235° C.
1H NMR DMSO-d6 (300 MHz): 1.25 (t, J=6.9, 2H); 4.00 (s, 3H); 4.02-4.30 (m, 6H); 5.72 (s, 1H); 6.31 (s, 1H); 7.25-7.35 (d, J=8.1, 1H); 7.36-7.50 (m, 2H); 7.60-7.75 (m, 2H); 7.96 (s, 1H); 8.28 (s, 1H).

EXAMPLE 80

3-(2,4-dichlorophenyl)-6-(5-ethoxymethyl-2H-pyrazol-3-yl)-1,9-dimethyl-1,9-dihydropyrido[2,3-b]indol-2-one

A) Compound A: 1-[3-(2,4-Dichlorophenyl)-1,9-dimethyl-2-oxo-2,9-dihydro-1H-pyrido[2,3-b]indol-6-yl]-4-ethoxybutane-1,3-dione 200 mg (0.5 mmol) of 6-acetyl-3-(2,4-dichlorophenyl)-1,9-dimethyl-1,9-dihydro-2H-pyrido[2,3-b]indol-2-one, preparation 1.10E, are dissolved in 5 ml of anhydrous THF. A spatula tip of dibenzo-18-crown-6 and a few drops of anhydrous EtOH are added. A solution of 132 mg (1 mmol) of ethylethoxy acetate and 42 mg (1.05 mmol) of 60% NaH in 5 ml of anhydrous THF is added. The mixture is refluxed for 3 hours. The reaction medium is allowed to return to ambient temperature and EtOAc is added. The organic phase is washed with a 1N HCl solution. The organic phase is dried over Na2SO4, filtered and evaporated to dryness.

280 mg of orange powder are obtained.
Yield: quantitative
MS: 485.13

B) 3-(2,4-Dichlorophenyl)-6-(5-ethoxymethyl-2H-pyrazol-3-yl)-1,9-dimethyl-1,9-dihydropyrido[2,3-b]indol-2-one The process is carried out as in Example 43 above, with compound A 1-[3-(2,4-dichlorophenyl)-1,9-dimethyl-2-oxo-2,9-dihydro-1H-pyrido[2,3-b]indol-6-yl]-4-ethoxybutane-1,3-dione and hydrazine hydrate Mp: 246° C.
1H NMR DMSO-d6 (300 MHz): 1.14 (t, J=1.9, 3H); 3.49 (q, J=6.9, 2H); 4.02 (s, 3H); 4.17 (s, 3H); 4.45 (d, J=21, 2H); 6.66 (s, 1H); 7.47 (m, 2H); 7.69 (m, 3H); 8.23 (m, 2H); 13.0 (m, 1H).

EXAMPLE 81

3-(4-Bromophenyl)-6-(5-hydroxymethyl-1-methyl-1H-pyrazol-3-yl)-1,9-dimethyl-1,9-dihydropyrido[2,3-b]indol-2-one

A) Compound A: 4-[3-(4-Bromophenyl)-1,9-dimethyl-2-oxo-2,9-dihydro-1H-pyrido[2,3-b]indol-6-yl]-2,4-dioxobutyric acid ethyl ester The process is carried out as in Example 80 above, with the compound from Example 60B, 6-acetyl-3-(4-bromophenyl)-1,9-dimethyl-1,9-dihydropyrido[2,3-b]indol-2-one and diethyl oxalate.

1H NMR DMSO-d6 (300 MHz): 1.31 (t, J=7.1, 3H); 4.03 (s, 3H); 4.18 (s, 3H); 4.35 (q, J=7.1, 2H); 7.30 (s, 1H); 7.60 (d, J=8.6, 2H); 7.80 (d, J=8.7, 3H); 8.00 (sd, J=1.7, J=8.8, 1H); 8.72 (s, 1H); 8.86 (s, 1H).

B) Compound B: 5-[3-(4-Bromophenyl)-1,9-dimethyl-2-oxo-2,9-dihydro-1H-pyrido[2,3-b]indol-6-yl]-1H-pyrazole-3-carboxylic acid ethyl ester The process is carried out as in Example 43 above, with compound A, 4-[3-(4-bromophenyl)-1,9-dimethyl-2-oxo-2,9-dihydro-1H-pyrido[2,3-b]indol-6-yl]-2,4-dioxobutyric acid ethyl ester and hydrazine monohydrate.

1H NMR DMSO-d6 (300 MHz): 1.30 (t, J=7.20, 3H); 3.98 (s, 3H); 4.12 (s, 3H); 4.30 (q, J=7.20, 2H); 7.20 (s, 1H); 7.66 (m, 6H); 8.44 (s, 2H); 13.86 (s, 1H).

C) Compound C: 5-[3-(4-Bromophenyl)-1,9-dimethyl-2-oxo-2,9-dihydro-1H-pyrido-[2,3-b]indol-6-yl]-2-methyl-2H-pyrazole-3-carboxylic acid ethyl ester The process is carried out as in Example 36 above, with compound B 5-[3-(4-bromophenyl)-1,9-dimethyl-2-oxo-2,9-dihydro-1H-pyrido[2,3-b]indol-6-yl]-1H-pyrazole-3-carboxylic acid ethyl ester and iodomethane 1H NMR DMSO-d6 (300 MHz): 1.32 (t, J=6.90, 3H); 3.99 (s, 3H); 4.12 (s, 6H); 4.32 (q, J=6.90, 2H); 7.34 (s, 1H); 7.59 (m, 3H); 7.76 (d, J=8.4, 3H); 8.46 (s, 1H); 8.57 (s, 1H).

D) 3-(4-Bromophenyl)-6-(5-hydroxymethyl-1-methyl-1H-pyrazol-3-yl)-1,9-dimethyl-1,9-dihydropyrido[2,3-b]indol-2-one 100 mg (0.2 mmol) of compound C: 5-[3-(4-bromophenyl)-1,9-dimethyl-2-oxo-2,9-dihydro-1H-pyrido[2,3-b]indol-6-yl]-2-methyl-2H-pyrazole-3-carboxylic acid ethyl ester are dissolved in 5 ml of anhydrous CH2Cl2 anhydrous. The mixture is refluxed and then 0.2 ml of 1M LiBH4 in THF is added. The mixture is refluxed for 20 hours, while further adding 3 times 0.2 ml of LiBH$_4$. The mixture is allowed to return to ambient temperature and 1 ml of 2N NaOH is added. The reaction medium is evaporated to dryness. Water is added, and the medium is acidified with 1N HCl and extracted with EtOAc. The organic phase is evaporated to dryness. The product is triturated in water, filtered, and washed with water. The product is taken up in methanol and evaporated to dryness.

65 mg of white powder are obtained.

1H NMR DMSO-d6 (300 MHz): 3.84 (s, 3H); 4.02 (s, 3H); 4.14 (s, 3H); 4.55 (d, J=5.1, 2H); 5.33 (t, J=5.4, 1H); 6.64 (s, 1H); 7.59 (m, 3H); 7.71 (sd, J=1.5, J=9.2, 1H); 7.81 (d, J=8.4, 2H); 8.38 (s, 1H); 8.58 (s, 1H).

EXAMPLE 82

3-(2,4-Dichlorophenyl)-6-(5-hydroxymethyl-1-methyl-1H-pyrazol-3-yl)-1,9-dimethyl-1,9-dihydropyrido[2,3-b]indol-2-one

A) Compound A: 5-[3-(2,4-Dichlorophenyl)-1,9-dimethyl-2-oxo-2,9-dihydro-1H-pyrido[2,3-b]indol-6-yl]-2-methyl-2H-pyrazole-3-carboxylic acid ethyl ester The process is carried out as in Example 36 above, with 5-[3-(2,4-dichlorophenyl)-1,9-dimethyl-2-oxo-2,9-dihydro-1H-pyrido[2,3-b]indol-6-yl]-2H-pyrazole-3-carboxylic acid ethyl ester from Example 43 above and iodomethane.

B) 3-(2,4-Dichlorophenyl)-6-(5-hydroxymethyl-1-methyl-1H-pyrazol-3-yl)-1,9-dimethyl-1,9-dihydropyrido[2,3-b]indol-2-one The process is carried out as in Example 81D above, with compound A 5-[3-(2,4-dichlorophenyl)-1,9-dimethyl-2-oxo-2,9-dihydro-1H-pyrido[2,3-b]indol-6-yl]-2-methyl-2H-pyrazole-3-carboxylic acid ethyl ester.

1H NMR DMSO-d6 (300 MHz): 3.82 (s, 3H); 4.01 (s, 3H); 4.16 (s, 3H); 4.52 (s, 2H); 5.34 (bs, 1H); 6.62 (s, 1H); 7.47 (m, 2H); 7.62 (m, 1H); 7.71 (m, 2H); 8.28 (m, 2H).

EXAMPLE 83

3-(2,4-Dichlorophenyl)-6-(1-methoxymethyl-4-methyl-1H-pyrazol-3-yl)-1,9-dimethyl-1,9-dihydropyrido[2,3-b]indol-2-one The process is carried out as in Example 36 above, with the compound from Example 53 above, 3-(2,4-dichlorophenyl)-1,9-dimethyl-6-(4-methyl-2H-pyrazol-3-yl)-1,9-dihydropyrido[2,3-b]indol-2-one.

1H NMR DMSO-d6 (300 MHz): 2.24 (s, 3H); 3.27 (s, 3H); 4.02 (s, 3H); 4.18 (s, 3H); 5.34 (s, 2H); 7.46-7.49 (m, 2H); 7.62-7.74 (m, 4H); 8.12 (d, J=0.9, 1H); 8.35 (s, 1H).

Mp=208-212° C.

EXAMPLE 84

3-(4-Bromophenyl)-6-(5-ethoxymethyl-2H-pyrazol-3-yl)-1,9-dimethyl-1,9-dihydropyrido[2,3-b]indol-2-one hydrochloride

A) Compound A: 1-[3-(4-Bromophenyl)-1,9-dimethyl-2-oxo-2,9-dihydro-1H-pyrido[2,3-b]indol-6-yl]-4-ethoxy-butane-1,3-dione The process is carried out as in Example 80 above, with the compound from Example 60B above, 6-acetyl-3-(4-bromophenyl)-1,9-dimethyl-1,9-dihydropyrido[2,3-b]indol,2-one and ethylethoxy acetate.

MS: 495.10

B) 3-(4-Bromophenyl)-6-(5-ethoxymethyl-2H-pyrazol-3-yl)-1,9-dimethyl-1,9-dihydropyrido[2,3-b]indol-2-one hydrochloride The process is carried out as in Example 43 above, with compound A 1-[3-(4-bromophenyl)-1,9-dimethyl-2-oxo-2, 9-dihydro-1H-pyrido[2,3-b]indol-6-yl]-4-ethoxy-butane-1,3-dione and hydrazine monohydrate Mp: >340° C. (decomp.)

1H NMR DMSO-d6 (300 MHz): 1.16 (t, J=6.9, 3H); 3.50 (q, J=6.9, 2H); 4.02 (s, 3H); 4.15 (s, 3H); 4.49 (s, 2H); 6.73 (s, 1H); 7.60 (m, 3H); 7.76 (m, 3H); 8.40 (s, 1H); 8.50 (s, 1H).

EXAMPLE 85

N-{2-[3-(4-Bromophenyl)-1,9-dimethyl-2-oxo-2,9-dihydro-1H-pyrido[2,3-b]indol-6-yl]thiazol-4-ylmethyl}-2,2-dimethylpropionamide 70 mg (0.15 mmol) of compound from Example 75 above 6-(4-aminomethylthiazol-2-yl)-3,4-bromophenyl)-1,9-dimethyl-1,9-dihydropyrido[2,3-b]indol-2-one are dissolved in 4 ml of anhydrous pyridine. 90 µl (0.73 mmol) of pivaloyl chloride are added. The mixture is stirred at ambient temperature under argon overnight. The reaction medium is evaporated to dryness, and the product is triturated in a saturated NH4Cl solution, filtered and washed with water. The product is triturated in an EtOAc/MeOH mixture and filtered.

30 mg of pale yellow powder are obtained.

Mp: 250-255° C.

1H NMR DMSO-d6 (300 MHz): 1.17 (s, 9H); 4.03 (s, 3H); 4.18 (s, 3H); 4.42 (d, J=6.0, 2H); 7.18 (s, 1H); 7.60 (d, J=8.4, 2H); 7.72 (d, J=8.1, 1H); 7.86 (m, 3H); 8.16 (m, 1H); 8.57 (s, 1H); 8.71 (s, 1H).

EXAMPLE 86

3-(4-Bromophenyl)-1,9-dimethyl-6-[5-(tetrahydropyran-2-yloxymethyl)-2H-pyrazol-3-yl]-1,9-dihydropyrido[2,3-b]indol-2-one A) Compound A: 1-[3-(4-Bromophenyl)-1,9-dimethyl-2-oxo-2,9-dihydro-1H-pyrido[2,3-b]indol-6-yl]-4-(tetrahydropyran-2-yloxy)butane-1,3-dione The process is carried out as in Example 80 above, with the compound from Example 60B above, 6-acetyl-3-(4-bromophenyl)-1,9-dimethyl-1,9-dihydropyrido[2,3-b]indol-2-one and (tetrahydropyran-2-yloxy)acetic acid ethyl ester.

MS: 551.16

B): 3-(4-Bromophenyl)-1,9-dimethyl-6-[5-(tetrahydropyran-2-yloxymethyl)-2H-pyrazol-3-yl]-1,9-dihydropyrido[2,3-b]indol-2-one The process is carried out as in Example 43 above, with compound A, 1-[3-(4-bromo-phenyl)-1,9-dimethyl-2-oxo-2,9-dihydro-1H-pyrido[2,3-b]indol-6-yl]-4-(tetrahydropyran-2-yloxy)butane-1,3-dione and hydrazine monohydrate.

Mp: 240-245° C.

1H NMR DMSO-d6 (300 MHz): 1.49 (m, 6H); 3.48 (m, 1H); 4.03 (s, 3H); 4.15 (s, 3H); 4.46 (m, 1H); 4.67 (m, 2H); 6.68 (d, J=6.50, 1H); 7.69 (m, 6H); 8.40 (m, 2H); 12.90 (m, 1H).

EXAMPLE 87

3-(4-Bromophenyl)-6-(5-hydroxymethyl-2H-pyrazol-3-yl)-1,9-dimethyl-1,9-dihydropyrido[2,3-b]indol-2-one 110 mg (0.2 mmol) of compound from Example 86 above, 3-(4-bromophenyl)-1,9-dimethyl-6-[5-(tetrahydropyran-2-yloxymethyl)-2H-pyrazol-3-yl]-1,9-dihydropyrido[2,3-b]indol-2-one are dissolved in 6 ml of MeOH. A spatula tip of p-toluenesulphonic acid is added and the mixture is refluxed overnight. The reaction medium is evaporated to dryness. A saturated NaHCO3 solution is added and the mixture is extracted with EtOAc. The organic phase is evaporated to dryness. The product obtained is triturated in water, filtered and washed with water. The product is taken up in methanol and evaporated to dryness.

80 mg of beige powder are obtained.

Mp: 287-290° C.

1H NMR DMSO-d6 (300 MHz): 4.03 (s, 3H); 4.15 (s, 3H); 4.47/4.53 (s/S, 2H); 5.0/5.29 (bs/BS, 1H); 6.61 (s, 1H); 7.67 (m, 6H); 8.46 (m, 2H); 12.67/12.91 (S/s, 1H).

EXAMPLE 88

3-(2,4-Dichlorophenyl)-1,9-dimethyl-6-[5-(tetrahydropyran-2-yloxymethyl)-2H-pyrazol-3-yl]-1,9-dihydropyrido[2,3-b]indol-2-one A) Compound A: 1-[3-(2,4-Dichlorophenyl)-1,9-dimethyl-2-oxo-2,9-dihydro-1H-pyrido[2,3-b]indol-6-yl]-4-(tetrahydropyran-2-yloxy)butane-1,3-dione The process is carried out as in Example 80 above, with the compound from preparation 1.10E, 6-acetyl-3-(2,4-dichlorophenyl)-1,9-dimethyl-1,9-dihydro-2H-pyrido[2,3-b]indol-2-one and (tetrahydropyran-2-yloxy)acetic acid ethyl ester.

MS: 541.19

B) 3-(2,4-Dichlorophenyl)-1,9-dimethyl-6-[5-(tetrahydropyran-2-yloxymethyl)-2H-pyrazol-3-yl]-1,9-dihydropyrido[2,3-b]indol-2-one The process is carried out as in Example 80 above, with compound A, 1-[3-(2,4-dichlorophenyl)-1,9-dimethyl-2-oxo-2,9-dihydro-1H-pyrido[2,3-b]indol-6-yl]-4-(tetrahydropyran-2-yloxy)butane-1,3-dione and hydrazine monohydrate.

Mp: 185-190° C.

1H NMR DMSO-d6 (300 MHz): 1.39 (m, 6H); 3.32 (m, 1H); 3.82 (m, 1H); 4.02 (s, 3H); 4.17 (s, 3H); 4.47 (bs, 1H); 4.63 (m, 2H); 6.67 (s, 1H); 7.47 (m, 2H); 7.69 (m, 3H); 8.26 (m, 2H); 12.90 (m, 1H).

EXAMPLE 89

3-(2,4-Dichlorophenyl)-6-(5-hydroxymethyl-2H-pyrazol-3-yl)-1,9-dimethyl-1,9-dihydropyrido[2,3-b]indol-2-one The process is carried out as in Example 87 above with the compound from Example 88B, 3-(2,4-dichlorophenyl)-1,9-dimethyl-6-[5-(tetrahydropyran-2-yloxymethyl)-2H-pyrazol-3-yl]-1,9-dihydropyrido[2,3-b]indol-2-one.

Mp: 283-289° C.

1H NMR DMSO-d6 (300 MHz) 4.02 (s, 3H); 4.17 (s, 3H); 4.50 (m, 2H); 4.99/5.28 (s/S, 1H); 6.59 (s, 1H); 7.48 (m, 2H); 7.69 (m, 3H); 8.28 (m, 2H); 12.65/12.90 (S/s, 1H).

EXAMPLE 90

3-(2,4-Dichlorophenyl)-1-methyl-6-(1-methyl-1H-pyrazol-3-yl)-2-oxo-1,2-dihydropyrido[2,3-b]indole-9-carbonitrile 460 mg (1.09 mmol) of compound from Example 37 above, 3-(2,4-dichlorophenyl)-1-methyl-6-(1-methyl-1H- pyrazol-3-yl)-1,9-dihydro-2H-pyrido[2,3-b]indol-2-one are dissolved in 50 ml of CH2Cl2. 576 mg (5.43 mmol) of CNBr, 44 mg (0.36 mmol) of DMAP and then 308 μl (2.17 mmol) of triethylamine are added. The mixture is stirred at ambient temperature for 18 h. H2O is added, the mixture is extracted with CH2Cl2, and the organic phase is dried over MgSO4, filtered and concentrated, and purification is carried out on a silica column, elution being carried out with EtOAc/50% cyclohexane.

128 mg of white powder are obtained.
Mp: 263° C.-266° C.
MS: 448.1
1H NMR DMSO-d6 (300 MHz): 3.89 (s, 3H); 3.99/4.00 (s, M/m, 3H); 6.46/6.72 (s, m/M, 1H); 7.40-7.56 (m, 2H); 7.57-7.70 (m, 1H); 7.70-7.87 (m, 2H); 7.88-8.98 (d, J=8.07, 1H); 8.19/8.42 (s, m/M, 2H).

EXAMPLE 91

3-(2,4-Dichlorophenyl)-6-(5-ethoxymethyl-2-ethyl-2H-pyrazol-3-yl)-1,9-dimethyl-1,9-dihydropyrido[2,3-b]indol-2-one The process is carried out as in Example 37 above, with the compound from Example 80A, 1-[3-(2,4-dichlorophenyl)-1,9-dimethyl-2-oxo-2,9-dihydro-1H-pyrido[2,3-b]indol-6-yl]-4-ethoxybutane-1,3-dione and ethylhydrazine oxalate.

1H NMR DMSO-d6 (300 MHz): 1.14 (t, J=6.99, 3H); 1.28 (t, J=7.2, 3H); 3.50 (q, J=6.99, 2H); 4.03 (s, 3H); 4.11 (q, J=7.2, 2H); 4.2 (s, 3H); 4.40 (s, 2H); 6.30 (s, 1H); 7.35 (sd, J=1.5, J=7.5, 1H); 7.45 (m, 2H); 7.70 (m, 2H); 8.00 (s, 1H); 8.32 (s, 1H).
Mp=163° C.-167° C.

EXAMPLE 92

3-(4-Fluorophenyl)-6-(5-ethoxymethyl-2-ethyl-2H-pyrazol-3-yl)-1,9-dimethyl-1,9-dihydropyrido[2,3-b]indol-2-one A) Compound A: 1-[3-(4-Fluorophenyl)-1,9-dimethyl-2-oxo-2,9-dihydro-1H-pyrido[2,3-b]indol-6-yl]-4-ethoxybutane-1,3-dione The process is carried out as in Example 80 above, with the compound from Example 72B above, 6-acetyl-3-(4-fluorophenyl)-1,9-dimethyl-1,9-dihydropyrido[2,3-b]indol-2-one and ethylethoxy acetate B) 3-(4-Fluorophenyl)-6-(5-ethoxymethyl-2-ethyl-2H-pyrazol-3-yl)-1,9-dimethyl-1,9-dihydropyrido[2,3-b]indol-2-one The process is carried out as in Example 37 above, with compound A, 1-[3-(4-fluorophenyl)-1,9-dimethyl-2-oxo-2,9-dihydro-1H-pyrido[2,3-b]indol-6-yl]-4-ethoxy-butane-1,3-dione and ethylhydrazine oxalate.

1H NMR DMSO-d6 (300 MHz): 1.15 (t, J=7.02, 3H); 1.29 (t, J=7.2, 3H); 3.50 (q, J=6.99, 2H); 4.04 (s, 3H); 4.13 (m, 5H); 4.41 (s, 2H); 6.32 (s, 1H); 7.23 (t, J=8.9, 2H); 7.33 (sd, J=1.5, J=8.4, 1H); 7.70 (d, J=8.7, 1H); 7.80 (m, 2H); 8.07 (s, 1H); 8.52 (s, 1H).
Mp=77° C.-83° C.

EXAMPLE 93

3-(4-Bromophenyl)-6-(5-ethoxymethyl-1-methyl-1H-pyrazol-3-yl)-1,9-dimethyl-1,9-dihydropyrido[2,3-b]indol-2-one The process is carried out as in Example 36 above, with the compound from Example 84, 3-(4-bromophenyl)-6-(5-ethoxymethyl-1H-pyrazol-3-yl)-1,9-dimethyl-1,9-dihydropyrido[2,3-b]indol-2-one and iodomethane.

1H NMR DMSO-d6 (300 MHz): 1.16 (t, J=6.99, 3H); 3.53 (q, J=6.99, 2H); 3.84/3.86 (S/s, 3H); 4.02/4.04 (S/s, 3H); 4.14/4.17 (S/s, 3H); 4.39/4.54 (s/S, 2H); 6.38/6.72 (s/S, 1H); 7.59 (m, 3H); 7.74 (m, 3H); 8.18/8.36 (s/S, 1H); 8.57 (s, 1H).
Mp=220° C.-225° C.

EXAMPLE 94

3-(2,4-Dichlorophenyl)-6-(5-dimethylaminomethyl-2H-pyrazol-3-yl)-1,9-dimethyl-1,9-dihydropyrido[2,3-b]indol-2-one A) Compound A: 1-[3-(2,4-Dichlorophenyl)-1,9-dimethyl-2-oxo-2,9-dihydro-1H-pyrido[2,3-b]indol-6-yl]-4-dimethylaminobutane-1,3-dione The process is carried out as in Example 80 above, with the compound from preparation 1.10E, 6-acetyl-3-(2,4-dichlorophenyl)-1,9-dimethyl-1,9-dihydro-2H-pyrido[2,3-b]indol-2-one and dimethylglycine methyl ester.
MS: 484.17.

B) 3-(2,4-Dichlorophenyl)-6-(5-dimethylaminomethyl-2H-pyrazol-3-yl)-1,9-dimethyl-1,9-dihydropyrido[2,3-b]indol-2-one The process is carried out as in Example 43 above, with compound A 1-[3-(2,4-dichlorophenyl)-1,9-dimethyl-2-oxo-2,9-dihydro-1H-pyrido[2,3-b]indol-6-yl]-4-dimethylaminobutane-1,3-dione and hydrazine monohydrate.

1H NMR DMSO-d6 (300 MHz): 2.18 (s, 6H); 3.47 (s, 2H); 4.02 (s, 3H); 4.17 (s, 3H); 6.58 (s, 1H); 7.46 (m, 2H); 7.69 (m, 3H); 8.29 (m, 2H); 12.66/12.90 (S/s, 1H).
Mp=238° C.-243° C.

EXAMPLE 95

3-(2,4-Dichlorophenyl)-6-(4-hydroxymethylthiazol-2-yl)-1,9-dimethyl-1,9-dihydropyrido[2,3-b]indol-2-one A) Compound A: 3-[3-(2,4-Dichlorophenyl)-1,9-dimethyl-2-oxo-2,9-dihydro-1H-pyrido[2,3-b]indole-6-carboximidoylsulphanyl]-2-oxopropionic acid ethyl ester A solution containing 200 mg (0.48 mmol) of compound 3-(2,4-dichlorophenyl)-1,9-dimethyl-2-oxo-2,9-dihydro-1H-pyrido[2,3-b]indole-6-carbothioic acid amide from preparation 1.6 above and 91 μl (0.72 mmol) of ethylbromopyruvate in 3 ml of DMF is stirred at ambient temperature for 2 h 30 min. 5 ml of H2O are added, and the precipitate formed is filtered off and washed with H2O and then with a minimum amount of Et2O (hygroscopic powder which has become pasty). The pasty residue is taken up in CH2Cl2 and MeOH and the product is concentrated to dryness. It is used as it is for stage B.
MS: 529.98

B) Compound B: 2-[3-(2,4-Dichlorophenyl)-1,9-dimethyl-2-oxo-2,9-dihydro-1H-pyrido[2,3-b]indol-6-yl]thiazole-4-carboxylic acid ethyl ester 3 ml of H2SO4 are added to compound A, 3-[3-(2,4-dichlorophenyl)-1,9-dimethyl-2-oxo-2,9-dihydro-1H-pyrido[2,3-b]indole-6-carboximidoylsulphanyl]-2-oxopropionic acid ethyl ester obtained above and the mixture is stirred at ambient temperature for 16 h. 15 ml of H2O and 5 ml of 1M NaOH are added. The mixture is extracted with EtOAC and concentrated without drying over MgSO4.

218 mg of yellow powder are obtained.
MS: 512.03
1H NMR DMSO-d6 (300 MHz): 1.31 (t, J=7.11, 3H); 4.00 (s, 3H); 4.18 (s, 3H); 4.32 (q, J=7.05, 2H); 7.45 (m, 2H); 7.67 (d, J=1.8, 1H); 7.73 (d, J=8.67, 1H); 7.90 (sd, J=8.61, J=1.74, 1H); 8.42 (s, 1H); 8.49 (s, 1H); 8.51 (d, J=1.53, 1H).

C) 3-(2,4-Dichlorophenyl)-6-(4-hydroxymethylthiazol-2-yl)-1,9-dimethyl-1,9-dihydropyrido[2,3-b]indol-2-one A solution containing 218 mg (0.43 mmol) of compound B, 2-[3-(2,4-dichlorophenyl)-1,9-dimethyl-2-oxo-2,9-dihydro-1H-pyrido[2,3-b]indol-6-yl]thiazole-4-carboxylic acid ethyl ester in 8 ml of CH2Cl2 is refluxed. 430 µl (0.85 mmol) of 2M LiBH4 in THF are added. The mixture is refluxed for 16 h. The reaction medium is left to cool, 10 ml of 1M NaOH are added and the reaction medium is concentrated to dryness. The residue is taken up in H2O, filtered and then washed with H2O and then with MeOH.

177 mg of white powder are obtained.
Mp: 240-243° C.
MS: 470.3
1H NMR DMSO-d6 (300 MHz): 3.99 (s, 3H); 4.16 (s, 3H); 4.59 (s, 2H); 5.36 (bs, 1H); 7.36 (s, 1H); 7.39-7.47 (m, 2H); 7.65 (d, J=1.8, 1H); 7.68 (d, J=8.88, 1H); 7.85 (sd, J=8.61, J=1.59, 1H); 8.38 (s, 1H); 8.44 (d, J=1.41, 1H).

EXAMPLE 96

2,2-Dimethyl-propionic acid 4-[3-(2,4-dichlorophenyl)-1-methyl-2-oxo-2,9-dihydro-1H-pyrido[2,3-b]indol-6-yl]thiazol-2-ylmethyl ester Described in Example 3A
1H NMR DMSO-d6 (300 MHz): 1.22 (s, 9H); 3.70 (s, 3H); 5.45 (s, 2H); 7.46 (s, 2H); 7.52 (d, J=8.43, 1H); 7.68 (m, 1H); 7.85 (sd, J=8.46, J=1.53, 1H); 7.99 (s, 1H); 8.25 (s, 1H); 8.46 (s, 1H); 12.24 (s, 1H).

EXAMPLE 97

2,2-Dimethylpropionic acid 4-[9-cyano-3-(2,4-dichlorophenyl)-1-methyl-2-oxo-2,9-dihydro-1H-pyrido[2,3-b]indol-6-yl]thiazol-2-ylmethyl ester The process is carried out as in Example 90 above, with the compound from Example 96, 2,2-dimethylpropionic acid 4-[3-(2,4-dichlorophenyl)-1-methyl-2-oxo-2,9-dihydro-1H-pyrido[2,3-b]indol-6-yl]thiazol-2-ylmethyl ester
Mp: 141-143° C.
MS: 565.1
1H NMR DMSO-d6 (300 MHz): 1.19 (s, 9H); 3.97 (s, 3H); 5.44 (s, 2H); 7.35-7.55 (m, 2H); 7.70 (m, 1H); 8.00 (m, 1H); 8.12 (d, J=4.50, 1H); 8.39 (d, J=4.50, 1H); 8.57 (s, 1H).

EXAMPLE 98

3-(2,4-Dichlorophenyl)-6-(2-methoxymethylthiazol-4-yl)-1,9-dimethyl-1,9-dihydropyrido[2,3-b]indol-2-one The process is carried out as in Example 10 above, with the compound from Example 9, 3-(2,4-dichlorophenyl)-6-(2-hydroxymethylthiazol-4-yl)-1,9-dimethyl-1,9-dihydropyrido[2,3-b]indol-2-one and iodomethane 1H NMR DMSO-d6 (300 MHz): 3.42 (s, 3H); 4.00 (s, 3H); 4.16 (s, 3H); 4.75 (s, 2H); 7.41-7.46 (m, 2H); 7.63-7.66 (m, 2H); 7.88 (sd, J=4.4, J=8.5, 1H); 7.97 (s, 1H); 8.25 (s, 1H); 8.45 (s, 1H).

Mp=180-183° C.

EXAMPLE 99

3-(2,4-Dichlorophenyl)-6-[1-(2,2-dimethylpropionyl)-4-methyl-1H-pyrazol-3-yl]-1,9-dimethyl-1,9-dihydropyrido[2,3-b]indol-2-one 0.14 g (0.32 mmol) of compound from Example 53, 3-(2,4-dichlorophenyl)-1,9-dimethyl-6-(4-methyl-2H-pyrazol-3-yl)-1,9-dihydropyrido[2,3-b]indol-2-one is dissolved in 5 ml of pyridine. 0.2 ml (1.6 mmol) of pivaloyl chloride is added. The mixture is stirred at ambient temperature for 2 hours. The reaction medium is poured into water, and extracted with EtOAc. Washing with a saturated NaCl solution, drying over Na2SO4 and then adsorbing onto silica are performed. Purification is carried out by chromatography on a silica column, elution being carried out with a 75/25 EtOAc/cyclohexane mixture and then with pure EtOAc.

100 mg of white powder are obtained.
1H NMR DMSO-d6 (300 MHz): 1.50 (s, 9H); 2.28 (s, 3H); 4.03 (s, 3H); 4.20 (s, 3H); 4.10 (s, 2H); 7.42-7.50 (m, 2H); 7.67-7.75 (m, 3H); 8.22 (s, 2H); 8.39 (s, 1H).
Mp=239-240° C.

EXAMPLE 100

3-(4-Fluorophenyl)-6-(4-hydroxymethylthiazol-2-yl)-1,9-dimethyl-1,9-dihydropyrido[2,3-b]indol-2-one A) Compound A: 3-(4-Fluorophenyl)-1,9-dimethyl-2-oxo-2,9-dihydro-1H-pyrido[2,3-b]indole-6-carbonitrile The process is carried out as indicated in preparation 1.2B above, with 1-methyl-2-(methylamino)-1H-indole-5-carbonitrile hydrochloride from preparation 1.5C above and 2-(4-fluorophenyl)-3-dimethylaminoacrylic acid methyl ester, preparation 2.12 WO5108398
1H NMR DMSO-d6 (300 MHz): 3.96 (s, 3H); 4.12 (s, 3H); 7.20 (t, J=8.94, 2H); 7.60 (sd, J=8.52, J=1.53, 1H); 7.75 (m, 3H); 8.39 (d, J=1.26, 1H); 8.44 (s, 1H).

B) Compound B: 3-(4-Fluorophenyl)-1,9-dimethyl-2-oxo-2,9-dihydro-1H-pyrido[2,3-b]indole-6-carbothioic acid amide The process is carried out as indicated in preparation 1.6 above, with compound A, 3-(4-fluorophenyl)-1,9-dimethyl-2-oxo-2,9-dihydro-1H-pyrido[2,3-b]indole-6-carbonitrile and O,O'-diethyldithiophosphate.
MS: 366.16
1H NMR DMSO-d6 (300 MHz): 4.02 (s, 3H); 4.16 (s, 3H); 7.22 (t, J=8.85, 2H); 7.61 (d, J=8.76, 1H); 7.82 (m, 2H); 7.91 (sd, J=8.79, J=1.32, 1H); 8.41 (s, 1H); 8.56 (s, 1H); 9.39 (s, 1H); 9.72 (s, 1H).

C) Compound C: 3-[3-(4-Fluorophenyl)-1,9-dimethyl-2-oxo-2,9-dihydro-1H-pyrido[2,3-b]indole-6-carboximidoylsulphanyl]-2-oxopropionic acid ethyl ester The process is carried out as indicated in Example 95 above, with compound B, 3-(4-fluorophenyl)-1,9-dimethyl-2-oxo-2,9-dihydro-1H-pyrido[2,3-b]indole-6-carbothioic acid amide and ethylbromopyruvate
MS: 480.4

D) Compound D: 2-[3-(4-Fluorophenyl)-1,9-dimethyl-2-oxo-2,9-dihydro-1H-pyrido[2,3-b]indol-6-yl]thiazole-4-carboxylic acid ethyl ester The process is carried out as indicated in Example 95 above, with compound C, 3-[3-(4-fluorophenyl)-1,9-dimethyl-2-oxo-2,9-dihydro-1H-pyrido[2,3-b]indole-6-carboximidoylsulphanyl]-2-oxopropionic acid ethyl ester obtained above.
MS: 462.4
1H NMR DMSO-d6 (300 MHz): 1.34 (t, J=7.11, 3H); 4.03 (s, 3H); 4.18 (s, 3H); 4.35 (q, J=7.05, 2H); 7.23 (t, J=8.76, 2H); 7.74 (d, J=8.67, 1H); 7.82-7.93 (m, 3H); 8.52 (s, 1H); 8.60 (s, 1H); 8.65 (s, 1H).

E) 3-(4-Fluorophenyl)-6-(4-hydroxymethylthiazol-2-yl)-1,9-dimethyl-1,9-dihydropyrido[2,3-b]indol-2-one The process is carried out as indicated in Example 95 above, with compound D, 2-[3-(4-fluorophenyl)-1,9-dimethyl-2-oxo-2,9-dihydro-1H-pyrido[2,3-b]indol-6-yl]-thiazole-4-carboxylic acid ethyl ester
Mp: 154-155° C.
MS: 420.19
1H NMR DMSO-d6 (300 MHz): 4.02 (s, 3H); 4.16 (s, 3H); 4.64 (d, J=5.4, 2H); 5.36 (t, J=5.64, 1H); 7.22 (t, J=8.91, 2H); 7.40 (s, 1H); 7.69 (d, J=8.64, 1H); 7.80-7.90 (m, 3H); 8.54 (d, J=1.32, 1H); 8.62 (s, 1H).

EXAMPLE 101

3-(4-Fluorophenyl)-6-(4-methoxymethylthiazol-2-yl)-1,9-dimethyl-1,9-dihydropyrido[2,3-b]indol-2-one 120 mg (0.286 mmol) of compound from Example 100 above, 3-(4-fluorophenyl)-6-(4-hydroxymethylthiazol-2-yl)-1,9-dimethyl-1,9-dihydropyrido[2,3-b]indol-2-one, are dissolved in 3 ml of DMF. 17 mg (0.429 mmol) of 60% NaH and a spatula of dibenzo-18-crown-6 are added. After stirring for 5 minutes, 27 μl (0.429 mmol) of iodomethane are added. The mixture is allowed to stir for 4 h at ambient temperature. A saturated NaHCO3 solution is added, the mixture is extracted with EtOAc and then with CH2Cl2 and the organic phase is concentrated to dryness without drying. The residue is taken up in MeOH, and the white precipitate is filtered off and washed with MeOH and then with a minimum amount of Et2O.
94 mg of white powder are obtained.
Mp: 222-223° C.
MS: 434.11
1H NMR DMSO-d6 (300 MHz): 3.37 (s, 3H); 4.01 (s, 3H); 4.16 (s, 3H); 4.54 (s, 2H); 7.22 (t, J=8.61, 2H); 7.55 (s, 1H); 7.69 (d, J=8.61, 1H); 7.82-7.90 (m, 3H); 8.55 (s, 1H); 8.63 (s, 1H).

EXAMPLE 102

3-(2,4-Dichlorophenyl)-6-(4-methoxymethylthiazol-2-yl)-1,9-dimethyl-1,9-dihydropyrido[2,3-b]indol-2-one The process is carried out as indicated in Example 101 above, with the compound from Example 95 above, 3-(2,4-dichlorophenyl)-6-(4-hydroxymethylthiazol-2-yl)-1,9-dimethyl-1,9-dihydropyrido[2,3-b]indol-2-one and iodomethane.
Mp: 318-322° C.
MS: 484.07
1H NMR DMSO-d6 (300 MHz): 3.35 (s, 3H); 4.00 (s, 3H); 4.18 (s, 3H); 4.52 (s, 2H); 7.40-7.50 (m, 2H); 7.52 (s, 1H); 6.67 (d, J=1.8, 1H); 7.71 (d, J=8.64, 1H); 7.86 (sd, J=8.61, J=1.74, 1H); 8.42 (s, 1H); 8.47 (d, J=1.56, 1H).

EXAMPLE 103

3-(2,4-Dichlorophenyl)-6-(4-ethoxymethylthiazol-2-yl)-1,9-dimethyl-1,9-dihydropyrido[2,3-b]indol-2-one The process is carried out as indicated in Example 101 above, with the compound from Example 95 above, 3-(2,4-dichlorophenyl)-6-(4-hydroxymethylthiazol-2-yl)-1,9-dimethyl-1,9-dihydropyrido[2,3-b]indol-2-one and iodoethane
Mp: 248-250° C.
MS: 498.2
1H NMR DMSO-d6 (300 MHz): 1.17 (t, J=6.96, 3H); 3.56 (q, J=6.96, 2H); 4.02 (s, 3H); 4.19 (s, 3H); 4.56 (s, 2H); 7.40-7.56 (m, 3H); 7.72 (d, J=10.5, 2H); 7.88 (d, J=7.71, 1H); 8.43 (s, 1H); 8.49 (s, 1H).

EXAMPLE 104

3-(4-Chlorophenyl)-1,9-dimethyl-6-(2H-pyrazol-3-yl)-1,9-dihydropyrido[2,3-b]indol-2-one A) Compound A: 3-(4-Chlorophenyl)-1,9-dimethyl-1,9-dihydropyrido[2,3-b]indol-2-one The process is carried out as indicated in preparation 1.2B above, with methyl-(1-methyl-1H-indol-2-yl)amine hydrochloride (prepared according to the procedures described in WO 2004/041817) and 3-dimethylamino-2-(4-chlorophenyl)acrylic acid methyl ester from preparation 2.8 WO2005/108398
1H NMR DMSO-d6 (300 MHz): 3.99 (s, 3H); 4.10 (s, 3H); 7.15-7.30 (m, 2H); 7.41 (m, 2H); 7.57 (d, J=7.86, 1H); 7.79 (m, 2H); 7.90 (sd, J=7.74, J=1.05, 1H); 8.42 (s, 1H).

B) Compound B: 6-Acetyl-3-(4-chlorophenyl)-1,9-dimethyl-1,9-dihydropyrido[2,3-b]indol-2-one The process is carried out as indicated in preparation 1.9B above, with compound A 3-(4-chlorophenyl)-1,9-dimethyl-1,9-dihydro-1H-pyrido[2,3-b]indol-2-one and acetyl chloride C) Compound C: 3-(4-Chlorophenyl)-6-(3-dimethylaminoacryloyl)-1,9-dimethyl-1,9-dihydropyrido[2,3-b]indol-2-one The process is carried out as indicated in preparation 1.9C above, with compound B 6-acetyl-3-(4-chlorophenyl)-1,9-dimethyl-1,9-dihydropyrido[2,3-b]indol-2-one and Bredereck's reagent.

D) 3-(4-Chlorophenyl)-1,9-dimethyl-6-(2H-pyrazol-3-yl)-1,9-dihydropyrido[2,3-b]indol-2-one The process is carried out as indicated in Example 36 above, with compound 3-(4-chlorophenyl)-6-(3-dimethylaminoacryloyl)-1,9-dimethyl-1,9-dihydropyrido[2,3-b]indol-2-one and hydrazine monohydrate.

Mp: 340-341° C.
MS: 389.17
1H NMR DMSO-d6 (300 MHz): 4.01 (s, 3H); 4.14 (s, 3H); 6.73 (s, 1H); 7.45 (d, J=8.52, 2H); 7.62 (m, 1H); 7.77 (m, 2H); 7.85 (d, J=8.31, 2H); 8.38 (s, 1H); 8.51 (m, 1H), 12.80/13.20 (bs, M/m, 1H).

EXAMPLE 105

3-(2,4-Dichlorophenyl)-1,9-dimethyl-6-(5-piperidin-1-ylmethyl-2H-pyrazol-3-yl)-1,9-dihydropyrido[2,3-b]indol-2-one A) Compound A: 3-(2,4-Dichlorophenyl)-1,9-dimethyl-2-oxo-2,9-dihydro-1H-pyrido[2,3-b]indol-6-yl]-4-piperidin-1-ylbutane-1,3-dione The process is carried out as in Example 37 above, with the compound from preparation 1.10E 6-acetyl-3-(2,4-dichlorophenyl)-1,9-dimethyl-1,9-dihydro-2H-pyrido[2,3-b]indol-2-one and piperidin-1-ylacetic acid methyl ester.

MS: 524.19

B) 3-(2,4-Dichlorophenyl)-1,9-dimethyl-6-(5-piperidin-1-ylmethyl-2H-pyrazol-3-yl)-1,9-dihydropyrido[2,3-b]indol-2-one The process is carried out as in Example 80 above, with compound A, 3-(2,4-dichlorophenyl)-1,9-dimethyl-2-oxo-2,9-dihydro-1H-pyrido[2,3-b]indol-6-yl]-4-piperidin-1-ylbutane-1,3-dione and hydrazine monohydrate 1H NMR DMSO-d6 (300 MHz): 1.50 (m, 6H); 2.37 (bs, 4H); 3.50 (bs, 2H); 4.02 (s, 3H); 4.17 (s, 3H); 6.58 (s, 1H); 7.47 (m, 2H); 7.69 (m, 3H); 8.30 (m, 2H); 12.62/12.89 (S/s, 1H).
Mp=228° C.-235° C.

EXAMPLE 106

3-(2,4-Dichlorophenyl)-1,9-dimethyl-6-(1-methyl-5-piperidin-1-ylmethyl-1H-pyrazol-3-yl)-1,9-dihydropyrido[2,3-b]indol-2-one hydrochloride The process is carried out as in Example 36 above, with the compound from Example 105, 3-(2,4-dichlorophenyl)-1,9-dimethyl-6-(5-piperidin-1-ylmethyl-2H-pyrazol-3-yl)-1,9-dihydropyrido[2,3-b]indol-2-one
1H NMR DMSO-d6 (300 MHz): 1.78 (m, 6H); 2.90 (m, 2H); 3.42 (m, 2H); 4.03 (s, 3H); 4.19 (s, 3H); 4.26 (m, 2H); 6.89 (s, 1H); 7.47 (m, 2H); 7.70 (m, 3H); 8.20 (m, 1H); 8.30 (s, 1H); 10.42 (s, 1H).
Mp=203° C.-208° C.

EXAMPLE 107

3-(2,4-Dichlorophenyl)-6-(5-ethoxymethyl-1-methyl-1H-pyrazol-3-yl)-1,9-dimethyl-1,9-dihydropyrido[2,3-b]indol-2-one The process is carried out as in Example 101 above, with the compound from Example 82, 3-(2,4-dichlorophenyl)-6-(5-hydroxymethyl-1-methyl-1H-pyrazol-3-yl)-1,9-dimethyl-1,9-dihydropyrido[2,3-b]indol-2-one and iodoethane.
1H NMR DMSO-d6 (300 MHz): 1.16 (t, J=6.99, 3H); 3.50 (q, J=6.99, 2H); 3.83 (s, 3H); 4.02 (s, 3H); 4.16 (s, 3H); 4.53 (s, 2H); 6.69 (s, 1H); 7.46 (m, 2H); 7.60 (d, J=8.64, 1H); 7.72 (m, 2H); 8.28 (s, 2H).
Mp=137° C.-142° C.

EXAMPLE 108

3-(2,4-Dichlorophenyl)-6-[2-ethyl-5-(2-pyrrolidin-1-yl-ethoxymethyl)-2H-pyrazol-3-yl]-1,9-dimethyl-1,9-dihydropyrido[2,3-b]indol-2-one hydrochloride The process is carried out as in Example 101 above, with the compound from Example 61, 3-(2,4-dichlorophenyl)-6-(2-ethyl-5-hydroxymethyl-2H-pyrazol-3-yl)-1,9-dimethyl-1,9-dihydropyrido[2,3-b]indol-2-one and chloroethylpyrrolidine.
1H NMR DMSO-d6 (300 MHz): 1.27 (t, J=4.17, 3H); 1.87 (m, 4H); 3.02 (m, 2H); 3.35 (m, 2H); 3.50 (m, 2H); 3.78 (m, 4H); 4.04 (s, 3H); 4.13 (q, J=7.23, 2H); 4.21 (s, 3H); 4.52 (s, 2H); 6.40 (s, 1H); 7.35 (sd, J=1.5, J=8.5, 1H); 7.45 (m, 2H); 7.73 (m, 2H); 7.99 (s, 1H); 8.32 (s, 1H).
Mp=125° C.-130° C.

EXAMPLE 109

6-(4-Aminomethylthiazol-2-yl)-3-(2,4-dichlorophenyl)-1-methyl-1,9-dihydropyrido[2,3-b]indol-2-one A) Compound A: 3-(2,4-Dichlorophenyl)-1-methyl-2-oxo-2,9-dihydro-1H-pyrido[2,3-b]indole-6-carbothioic acid amide The process is carried out as for preparation 1.6 above, with 3-(2,4-dichlorophenyl)-1-methyl-2-oxo-2,9-dihydro-1H-pyrido[2,3-b]indole-6-carbonitrile (1H NMR DMSO-d6 (300 MHz): 3.70 (s, 3H); 7.47 (m, 2H); 7.63 (m, 3H); 8.27 (s, 1H); 8.40 (s, 1H); 12.69 (s, 1H)) and O,O'-diethyldithiophosphate
1H NMR DMSO-d6 (300 MHz): 3.70 (s, 3H); 7.46 (m, 3H); 7.69 (s, 1H); 7.87 (d, J=8.52, 1H); 8.19 (s, 1H); 8.46 (s, 1H); 9.38/9.69 (2s, 2H); 12.39 (s, 1H).

B) Compound B: 6-(4-Chloromethylthiazol-2-yl)-3-(2,4-dichlorophenyl)-1-methyl-1,9-dihydropyrido[2,3-b]indol-2-one The process is carried out as in Example 75, with compound A: 3-(2,4-dichlorophenyl)-1-methyl-2-oxo-2,9-dihydro-1H-pyrido[2,3-b]indole-6-carbothioic acid amide and 1,3-dichloroacetone.
1H NMR DMSO-d6 (300 MHz): 3.71 (s, 3H); 4.87 (s, 2H); 7.47 (m, 2H); 7.57 (d, J=8.4, 1H); 7.70 (m, 2H); 7.85 (sd, J=1.8, J=8.4, 1H); 8.40 (s, 1H); 8.49 (s, 1H); 12.39 (s, 1H).

C) Compound C: 6-(4-Azidomethylthiazol-2-yl)-3-(2,4-dichlorophenyl)-1-methyl-1,9-dihydropyrido[2,3-b]indol-2-one The process is carried out as in Example 75, with compound B: 6-(4-chloromethyl-thiazol-2-yl)-3-(2,4-dichlorophenyl)-1-methyl-1,9-dihydropyrido[2,3-b]indol-2-one
MS: 481.2.

D) 6-(4-Aminomethylthiazol-2-yl)-3-(2,4-dichlorophenyl)-1-methyl-1,9-dihydropyrido[2,3-b]indol-2-one The process is carried out as in Example 75, with compound C: 6-(4-azidomethyl-thiazol-2-yl)-3-(2,4-dichlorophenyl)-1-methyl-1,9-dihydropyrido[2,3-b]indol-2-one
1H NMR DMSO-d6 (300 MHz): 3.70 (s, 3H); 3.89 (s, 2H); 7.37 (s, 1H); 7.53 (m, 3H); 7.68 (s, 1H); 7.82 (d, J=8.4, 1H); 8.34 (s, 1H); 8.45 (s, 1H).
Mp=205° C.-210° C.

EXAMPLE 110

3-(4-Fluorophenyl)-6-(1-methoxymethyl-1H-pyrazol-3-yl)-1,9-dimethyl-1,9-dihydropyrido[2,3-b]indol-2-one A) Compound A: 1-(Aminoacryloyl)-3-(4-fluorophenyl)-1,9-dimethyl-1,9-dihydro-pyrido[2,3-b]indol-2-one The process is carried out as in preparation 1.9C above, using compound from Example 72B, 6-acetyl-3-(4-fluorophenyl)-1,9-dimethyl-1,9-dihydropyrido[2,3-b]indol-2-one and Bredereck's reagent.

B) Compound B: 3-(4-Fluorophenyl)-1,9-dimethyl-6-(1H-pyrazol-3-yl)-1,9-dihydropyrido[2,3-b]indol-2-one The process is carried out as in Example 40 above, using compound A, 1-amino-acryloyl)-3-(4-fluorophenyl)-1,9-dimethyl-1,9-dihydropyrido[2,3-b]indol-2-one and hydrazine hydrate.

C) 3-(4-Fluorophenyl)-6-(1-methoxymethyl-1H-pyrazol-3-yl)-1,9-dimethyl-1,9-dihydropyrido[2,3-b]indol-2-one 303 mg (0.81 mmol) of compound B 3-(4-fluorophenyl)-1,9-dimethyl-6-(1H-pyrazol-3-yl)-1,9-dihydropyrido[2,3-b]indol-2-one are dissolved in 8 ml of DMF. 50 mg (1.22 mmol) of 60% NaH and a spatula of dibenzo-18-crown-6 are added. After stirring for 5 minutes, 73 µl (0.89 mmol) of bromomethyl methyl ether are added. The mixture is left to stir for 4 h at ambient temperature. A saturated NaHCO3 solution is added, the mixture extracted with EtOAc, and the organic phase is dried over MgSO4, filtered, and concentrated to dryness, adsorbing onto silica. The mixture is enriched in beta isomer by chromatography on a silica column, elution being carried out with 70/30 EtOAc/cyclohexane (ratio obtained: 62/38 beta/alpha) and then by means of a second purification by chromatography on a silica column, elution being carried out with 60/40 EtOAc/cyclohexane.
215 mg of yellow crystals (67/33 beta/alpha) are obtained.
MS: 417.2

1H NMR DMSO-d6 (300 MHz): 3.29/3.30 (s, m/M, 3H); 4.01/4.02 (s, M/m, 3H); 4.14/4.17 (s, M/m, 3H); 5.42/5.43 (s, M/m, 2H); 6.54/6.83 (d, m/M, J=1.71/J=2.34, 1H); 7.22 (m, 2H); 7.50 (m, ⅓H); 7.61 (m, 1H); 7.72 (d, J=8.55, ⅓H); 7.76-7.90 (m, ⅔H); 7.96 (d, M, J=2.31, ⅔H); 8.14/8.40 (m, m/M, 1H); 8.42/8.50 (s, m/M, 1H).

A second chromatography makes it possible to obtain the pure beta derivative.

EXAMPLE 111

3-(4-Chlorophenyl)-6-(1-methoxymethyl-1H-pyrazol-3-yl)-1,9-dimethyl-1,9-dihydropyrido[2,3-b]indol-2-one The process is carried out as in Example 110 above, using compound from Example 104, 3-(4-chlorophenyl)-1,9-dimethyl-6-(1H-pyrazol-3-yl)-1,9-dihydropyrido[2,3-b]indol-2-one and bromomethyl methyl ether.
Mp: 245-247° C.
MS: 433.25
1H NMR DMSO-d6 (300 MHz): 3.30 (s, 3H); 4.02 (s, 3H); 4.14 (s, 3H); 5.42 (s, 2H); 6.83 (d, J=1.83, 1H); 7.44 (d, J=8.4, 2H); 7.62 (d, J=8.52, 1H); 7.78 (d, J=8.79, 1H); 7.87 (d, J=8.43, 2H); 7.96 (d, J=1.89, 1H); 8.42 (s, 1H); 8.56 (s, 1H).

EXAMPLE 112

3-(4-Fluorophenyl)-1,9-dimethyl-6-(4-methyl-2H-pyrazol-3-yl)-1,9-dihydropyrido[2,3-b]indol-2-one A) Compound A: 3-(4-Fluorophenyl)-1,9-dimethyl-6-propionyl-1,9-dihydropyrido[2,3-b]indol-2-one The process is carried out as indicated in preparation 1.1E above, with compound from Example 63A, 3-(4-fluorophenyl)-1,9-dimethyl-1,9-dihydropyrido[2,3-b]indol-2-one and propionyl chloride
1H NMR DMSO-d6 (300 MHz): 1.13 (t, J=7.2, 3H); 3.10 (q, J=7.2, 2H); 4.00 (s, 3H); 4.15 (s, 3H); 7.23 (t, J=8.9, 2H); 7.66 (d, J=8.7, 1H); 7.80-7.90 (m, 3H); 8.56 (s, 1H); 8.66 (s, 1H).

B) Compound B: 6-(3-Dimethylamino-2-methylacryloyl)-3-(4-fluorophenyl)-1,9-dimethyl-1,9-dihydropyrido[2,3-b]indol-2-one The process is carried out as indicated in preparation 1.9C above, with compound A 3-(4-fluorophenyl)-1,9-dimethyl-6-propionyl-1,9-dihydropyrido[2,3-b]indol-2-one and Bredereck's reagent.
1H NMR DMSO-d6 (300 MHz): 2.05 (s, 3H); 2.98 (s, 6H); 4.01 (s, 3H); 4.14 (s, 3H); 6.91 (s, 1H); 7.17-1.28 (m, 3H); 7.55 (d, J=8.4, 1H); 7.78-7.83 (m, 2H); 7.96 (s, 1H); 8.50 (s, 1H).

C) 3-(4-Fluorophenyl)-1,9-dimethyl-6-(4-methyl-2H-pyrazol-3-yl)-1,9-dihydropyrido[2,3-b]indol-2-one The process is carried out as in Example 40 above using compound B, 6-(3-dimethylamino-2-methylacryloyl)-3-(4-fluorophenyl)-1,9-dimethyl-1,9-dihydropyrido[2,3-b]indol-2-one and hydrazine hydrate.
1H NMR DMSO-d6 (300 MHz): 2.24 (s, 3H); 4.02 (s, 3H); 4.15 (s, 3H); 7.21 (t, J=8.9, 2H); 7.48-7.55 (m, 2H); 7.65 (d, J=8.6, 1H); 7.78-7.83 (m, 2H); 8.14 (s, 1H); 8.47 (s, 1H).
Mp=311-312° C.

EXAMPLE 113

3-(4-Fluorophenyl)-6-(1-methoxymethyl-4-methyl-1H-pyrazol-3-yl)-1,9-dimethyl-1,9-dihydropyrido[2,3-b]indol-2-one The process is carried out as in Example 36 above, using compound from Example 112, 3-(4-fluorophenyl)-1,9-dimethyl-6-(4-methyl-2H-pyrazol-3-yl)-1,9-dihydropyrido[2,3-b]indol-2-one and bromomethyl methyl ether.

1H NMR DMSO-d6 (300 MHz): 4.00 (s, 3H); 4.14 (s, 3H); 4.49 (d, J=5.6, 2H); 5.35 (t, J=5.6, 1H); 7.41-7.49 (m, 3H); 7.56 (d, J=8.6, 1H); 7.68-7.71 (m, 2H); 8.19 (s, 1H); 8.23 (s, 1H).

Mp=166-168° C.

EXAMPLE 114

2,2-Dimethylpropionic acid 4-[3-(4-chlorophenyl)-1,9-dimethyl-2-oxo-2,9-dihydro-1H-pyrido[2,3-b]indol-6-yl]thiazol-2-yl methyl ester

A) Compound A: 6-(2-Bromoacetyl)-3-(4-chlorophenyl)-1,9-dimethyl-1,9-dihydropyrido[2,3-b]indol-2-one The process is carried out as in preparation 1.1 above, using compound from Example 104A, 3-(4-chlorophenyl)-1,9-dimethyl-1,9-dihydropyrido[2,3-b]indol-2-one and bromoacetyl chloride.

1H NMR DMSO-d6 (300 MHz): 4.03 (s, 3H); 4.20 (s, 3H); 4.96 (s, 2H); 7.47 (m, 2H); 7.74 (d, J=8.7, 1H); 7.84 (m, 2H); 7.94 (sd, J=1.7, J=8.7, 1H); 8.62 (s, 1H); 8.75 (s, 1H).

B) 2,2-Dimethylpropionic acid 4-[3-(4-chlorophenyl)-1,9-dimethyl-2-oxo-2,9-dihydro-1H-pyrido[2,3-b]indol-6-yl]thiazol-2-ylmethyl ester The process is carried out as for Example 8 above, using compound A, 6-(2-bromo-acetyl)-3-(4-chlorophenyl)-1,9-dimethyl-1,9-dihydropyrido[2,3-b]indol-2-one and 2-amino-2-thioxoethyl pivalate.

1H NMR DMSO-d6 (300 MHz): 1.23 (s, 9H); 4.02 (s, 3H); 4.15 (s, 3H); 5.47 (s, 2H); 7.45 (d, J=8.7, 2H); 7.65 (d, J=8.7, 1H); 7.87 (m, 3H); 8.05 (s, 1H); 8.54 (m, 2H).

Mp=225° C.-228° C.

EXAMPLE 115

3-(4-Chlorophenyl)-6-(2-hydroxymethylthiazol-4-yl)-1,9-dimethyl-1,9-dihydropyrido[2,3-b]indol-2-one The process is carried out as for Example 9 above, using compound from Example 114, 2,2-dimethylpropionic acid 4-[3-(4-chlorophenyl)-1,9-dimethyl-2-oxo-2,9-dihydro-1H-pyrido[2,3-b]indol-6-yl]thiazol-2-ylmethyl ester 1H NMR DMSO-d6 (300 MHz): 4.03 (s, 3H); 4.16 (s, 3H); 4.82 (d, J=4.53, 2H); 6.10 (bs, 1H); 7.44 (d, J=8.7, 2H); 7.65 (d, J=8.7, 1H); 7.88 (m, 3H); 7.94 (s, 1H); 8.53 (m, 2H).

Mp=256° C.-260° C.

EXAMPLE 116

6-(2-Aminothiazol-4-yl)-3-(4-chlorophenyl)-1,9-dimethyl-1,9-dihydropyrido[2,3-b]indol-2-one The process is carried out as for Example 21 above, using compound from Example 114A 6-(2-bromoacetyl)-3-(4-chlorophenyl)-1,9-dimethyl-1,9-dihydropyrido[2,3-b]indol-2-one and thiourea.

1H NMR DMSO-d6 (300 MHz): 4.02 (s, 3H); 4.14 (s, 3H); 6.93 (s, 1H); 6.99 (bs, 2H); 7.45 (d, J=8.4, 2H); 7.57 (d, J=8.7, 1H); 7.76 (d, J=8.4, 1H); 7.85 (d, J=8.7, 2H); 8.36 (s, 1H); 8.44 (s, 1H).

Mp=320° C.-323° C. (decomp.)

EXAMPLE 117

6-(5-Ethoxymethyl-2H-pyrazol-3-yl)-3-(4-fluorophenyl)-1,9-dimethyl-1,9-dihydropyrido[2,3-b]indol-2-one

A) Compound A: 3-(4-Fluorophenyl)-1,9-dimethyl-2-oxo-2,9-dihydro-1H-pyrido[2,3-b]indol-6-yl]butane-1,3-dione The process is carried out as for Example 59 above, using compound from Example 72A, 6-acetyl-3-(4-fluorophenyl)-1,9-dimethyl-1,9-dihydropyrido[2,3-b]indol-2-one and ethylethoxy acetate

MS: 435.24

B) 6-(5-Ethoxymethyl-2H-pyrazol-3-yl)-3-(4-fluorophenyl)-1,9-dimethyl-1,9-dihydropyrido[2,3-b]indol-2-one The process is carried out as in Example 43 above, with compound A, 3-(4-fluorophenyl)-1,9-dimethyl-2-oxo-2,9-dihydro-1H-pyrido[2,3-b]indol-6-yl]butane-1,3-dione and hydrazine monohydrate $^1$H NMR DMSO-d6 (300 MHz): 1.15 (t, J=7.0, 3H); 3.51 (q, J=7.0, 2H); 3.99 (s, 3H); 4.15 (s, 3H); 4.45 (d, J=19.4, 2H); 6.68 (s, 1H); 7.23 (t, J=8.85, 2H); 7.67 (m, 4H); 8.37 (m, 2H); 12.82/13.03 (2s, 1H).

EXAMPLE 118

6-(2-Aminothiazol-4-yl)-3-(4-fluorophenyl)-1,9-dimethyl-1,9-dihydropyrido[2,3-b]indol-2-one

A) Compound A: 6-(2-Bromoacetyl)-3-(4-fluorophenyl)-1,9-dimethyl-1,9-dihydropyrido[2,3-b]indol-2-one The process is carried out as in preparation 1.1 above, using compound from Example 72A, 3-(4-fluorophenyl)-1,9-dimethyl-1,9-dihydropyrido[2,3-b]indol-2-one and bromoacetyl chloride.

1H NMR DMSO-d6 (300 MHz): 4.04 (s, 3H); 4.20 (s, 3H); 4.96 (s, 2H); 7.25 (t, J=8.7, 2H); 7.75 (d, J=8.7, 1H); 7.82 (m, 2H); 7.94 (sd, J=1.8, J=8.7, 1H); 8.57 (s, 1H); 8.75 (s, 1H).

B) 6-(2-Aminothiazol-4-yl)-3-(4-fluorophenyl)-1,9-dimethyl-1,9-dihydropyrido[2,3-b]indol-2-one The process is carried out as for Example 21 above, using compound A, 6-(2-bromoacetyl)-3-(4-fluorophenyl)-1,9-dimethyl-1,9-dihydropyrido[2,3-b]indol-2-one and thiourea.

1H NMR DMSO-d6 (300 MHz): 4.01 (s, 3H); 4.13 (s, 3H); 6.92 (s, 1H); 6.99 (bs, 2H); 7.22 (t, J=9.0, 2H); 7.55 (d, J=8.4, 1H); 7.75 (d, J=8.4, 1H); 7.83 (m, 2H); 8.35 (s, 1H); 8.38 (s, 1H).

Mp=265° C.-268° C. (decomp.)

EXAMPLE 119

3-(2,4-Dichlorophenyl)-1,9-dimethyl-6-(2-methyl-2H-pyrazol-3-yl)-1,9-dihydropyrido[2,3-b]indol-2-one The process is carried out as in Example 37 above, with the compound from preparation 1.10F, 3-(2,4-dichlorophenyl)-6-(3-dimethylaminoacryloyl)-1,9-dimethyl-1,9-dihydropyrido[2,3-b]indol-2-one and methylhydrazine Mp: 134-136° C.
MS: 437.2

1H NMR DMSO-d6 (300 MHz): 3.87 (s, 3H); 4.03 (s, 3H); 4.19 (s, 3H); 6.39 (d, J=1.77, 1H); 7.48-7.52 (m, 4H); 7.68-7.80 (m, 2H); 8.06 (s, 1H); 8.31 (s, 1H).

EXAMPLE 120

6-(5-Ethoxymethyl-1-methyl-1H-pyrazol-3-yl)-3-(4-fluorophenyl)-1,9-dimethyl-1,9-dihydropyrido[2,3-b]indol-2-one The process is carried out as in Example 36 above, with the compound from Example 117, 6-(5-ethoxymethyl-1H-pyrazol-3-yl)-3-(4-fluorophenyl)-1,9-dimethyl-1,9-dihydropyrido[2,3-b]indol-2-one and methyl iodide.

1H NMR DMSO-d6 (300 MHz): 1.16 (t, J=7.0, 3H); 3.52 (q, J=7.0, 2H); 3.84 (s, 3H); 4.02 (s, 3H); 4.14 (s, 3H); 4.54 (s, 2H); 6.71 (s, 1H); 7.23 (t, J=9.0, 2H); 7.56 (d, J=8.7, 1H); 7.72 (d, J=8.7, 1H); 7.85 (m, 2H); 8.35 (s, 1H); 8.50 (s, 1H).

Mp=148° C.-15° C.

EXAMPLE 121

3-(4-Chlorophenyl)-6-(2-ethoxymethylthiazol-4-yl)-1,9-dimethyl-1,9-dihydropyrido[2,3-b]indol-2-one The process is carried out as in Example 10 above, with the compound from Example 115, 3-(4-chlorophenyl)-6-(2-hydroxymethylthiazol-4-yl)-1,9-dimethyl-1,9-dihydropyrido[2,3-b]indol-2-one and iodoethane.

1H NMR DMSO-d6 (300 MHz): 1.21 (t, J=6.9, 3H); 3.67 (q, J=6.9, 2H); 4.02 (s, 3H); 4.16 (s, 3H); 4.83 (s, 2H); 7.45 (d, J=8.7, 2H); 7.65 (d, J=8.7, 1H); 7.88 (m, 3H); 8.0 (s, 1H); 8.54 (s, 2H).

Mp=202° C.-206°

EXAMPLE 122

3-(2,4-Dichlorophenyl)-1,9-dimethyl-6-(1-methyl-5-morpholin-4-ylmethyl-1H-pyrazol-3-yl)-1,9-dihydropyrido[2,3-b]indol-2-one hydrochloride A) Compound A: 6-(5-Chloromethyl-1-methyl-1H-pyrazol-3-yl)-3-(2,4-dichlorophenyl)-1,9-dimethyl-1,9-dihydropyrido[2,3-b]indol-2-one 690 mg (1.48 mmol) of compound from Example 82, 3-(2,4-dichlorophenyl)-6-(5-hydroxymethyl-1-methyl-1H-pyrazol-3-yl)-1,9-dimethyl-1,9-dihydropyrido[2,3-b]indol-2-one are dissolved in 20 ml of anhydrous CH2Cl2. 0.62 ml (4.44 mmol) of Et3N and 0.32 ml of methanesulphonyl chloride are added. The mixture is stirred at ambient temperature for 3 days. The reaction medium is adsorbed onto silica and purification is carried out on a silica column, elution being carried out with a 75/25 EtOAc/cyclohexane mixture, and then with EtOAc.

400 mg of white powder are obtained.

1H NMR DMSO-d6 (300 MHz): 3.89 (s, 3H); 4.02 (s, 3H); 4.77 (s, 3H); 4.97 (s, 2H); 6.80 (s, 1H); 7.50 (m, 2H); 7.70 (m, 3H); 8.29 (s, 2H).

B) 3-(2,4-Dichlorophenyl)-1,9-dimethyl-6-(1-methyl-5-morpholin-4-ylmethyl-1H-pyrazol-3-yl)-1,9-dihydropyrido[2,3-b]indol-2-one hydrochloride 100 mg (0.2 mmol) of compound A, 6-(5-chloromethyl-1-methyl-1H-pyrazol-3-yl)-3-(2,4-dichlorophenyl)-1,9-dimethyl-1,9-dihydropyrido[2,3-b]indol-2-one are dissolved in 5 ml of anhydrous DMF. 55 mg (0.4 mmol) of K2CO3 and 22 µl (0.25 mmol) of morpholine are added. The mixture is heated at 80° C. overnight. It is allowed to return to ambient temperature and poured into water. The mixture is extracted with EtOAc. The organic phase is washed with a saturated NaCl solution. It is dried over Na2SO4, filtered and evaporated to dryness. Purification is carried out on a silica column, elution being carried out with a 95/05 EtOAc/MeOH mixture. The product obtained is dissolved in EtOAc and 0.5 ml of a saturated solution of HCl in Et2O/petroleum ether is added. The precipitate formed is filtered off and washed with ether. The product is taken up in MeOH and evaporated to dryness.

40 mg of white powder are obtained.

1H NMR pyridine-d6 (300 MHz): 2.28 (t, J=4.5, 4H); 3.35 (s, 2H); 3.55 (t, J=4.5, 4H); 3.73 (s, 3H); 3.77 (s, 3H); 3.85 (s, 3H); 6.73 (s, 1H); 7.30 (m, 1H); 7.50 (m, 2H); 7.98 (s, 1H); 8.09 (sd, J=1.6, J=8.5, 1H).

Mp: 225° C.-230° C. (decomp.)

EXAMPLE 123

3-(2,4-Dichlorophenyl)-1,9-dimethyl-6-[1-methyl-5-(4-methylpiperazin-1-ylmethyl)-1H-pyrazol-3-yl]-1,9-dihydropyrido[2,3-b]indol-2-one hydrochloride 100 mg (0.2 mmol) of compound from Example 122A: 6-(5-chloromethyl-1-methyl-1H-pyrazol-3-yl)-3-(2,4-dichlorophenyl)-1,9-dimethyl-1,9-dihydropyrido[2,3-b]indol-2-one are dissolved in 6 ml of anhydrous THF and 1 ml of NMP. 55 mg (0.4 mmol) of K2CO3 and 28 µl (0.25 mmol) of N-methylpiperazine are added. The mixture is refluxed overnight. It is allowed to return to ambient temperature and poured into water. The mixture is extracted with EtOAc. The organic phase is dried over Na2SO4, filtered and evaporated to dryness. The product obtained is dissolved in 5 ml of EtOAc and 0.5 ml of a saturated solution of HCl in Et2O/petroleum ether is added. The precipitate formed is filtered off and washed with ether. The product is taken up in MeOH and evaporated to dryness.

65 mg of beige powder are obtained.

1H NMR pyridine-d6 (300 MHz): 2.55 (s, 3H); 2.83 (bs, 4H); 3 (bs, 4H); 3.39 (s, 2H); 3.74 (s, 3H); 3.77 (s, 3H); 3.80 (s, 3H); 6.65 (s, 1H); 7.29 (m, 1H); 7.50 (m, 2H); 8 (s, 1H); 8.08 (sd, J=1.5, J=8.5, 1H).

Mp: 235° C.-241° C. (decomp.)

EXAMPLE 124

3-(2,4-Dichlorophenyl)-1,9-dimethyl-6-{1-methyl-5-[(2-morpholin-4-yl-ethylamino)methyl]-1H-pyrazol-3-yl}-1,9-dihydropyrido[2,3-b]indol-2-one hydrochloride The process is carried out as in Example 122 above, with the compound from Example 122A: 6-(5-chloromethyl-1-methyl-1H-pyrazol-3-yl)-3-(2,4-dichloro-phenyl)-1,9-dimethyl-1,9-dihydropyrido[2,3-b]indol-2-one and aminoethylmorpholine.

1H NMR pyridine-d6 (300 MHz): 2.38 (bs, 4H); 2.85 (t, J=5.9, 2H); 3.28 (t, J=5.9, 2H); 3.46 (t, J=4.5, 4H); 3.71 (s, 3H); 3.75 (s, 3H); 4.05 (s, 3H); 4.50 (s, 2H); 7.30 (m, 3H); 7.50 (m, 2H); 7.88 (s, 1H); 7.98 (m, 1H); 8.50 (s, 1H).
Mp: 233° C.-237° C. (decomp.)

EXAMPLE 125

6-[1-(2-Cyclopropylmethoxyethyl)-1H-pyrazol-3-yl]-3-(2,4-dichlorophenyl)-1,9-dimethyl-1,9-dihydropyrido[2,3-b]indol-2-one The process is carried out as in Example 101 above, with the compound from Example 51, 3-(2,4-dichlorophenyl)-6-[1-(2-hydroxyethyl)-1H-pyrazol-3-yl]-1,9-dimethyl-1,9-dihydropyrido[2,3-b]indol-2-one and (bromomethyl)cyclopropane.
Mp: 164-165° C.
MS: 521.11
1H NMR DMSO-d6 (300 MHz): 0.15 (m, 2H); 0.43 (m, 2H); 0.97 (m, 1H); 3.24 (d, J=6.78, 2H); 3.79 (t, J=5.43, 2H); 4.01 (s, 3H); 4.16 (s, 3H); 4.29 (t, J=5.4, 2H); 6.69 (d, J=2.25, 1H); 7.40-7.51 (m, 2H); 7.61 (d, J=8.61, 1H); 7.68 (d, J=1.62, 1H); 7.73 (m, 2H); 8.28 (m, 2H).

EXAMPLE 126

3-(2,4-Dichlorophenyl)-6-{1-[2-(2-ethoxyethoxy)ethyl]-1H-pyrazol-3-yl}-1,9-dimethyl-1,9-dihydropyrido[2,3-b]indol-2-one The process is carried out as in Example 101 above, with the compound from Example 51, 3-(2,4-dichlorophenyl)-6-[1-(2-hydroxyethyl)-1H-pyrazol-3-yl]-1,9-dimethyl-1,9-dihydropyrido[2,3-b]indol-2-one and 2-bromoethyl ethyl ether.
Mp: 165-170° C.
MS: 539.04
1H NMR DMSO-d6 (300 MHz): 1.06 (t, J=6.99, 3H); 3.34-3.42 (m, 2H); 3.43-3.50 (m, 2H); 3.50-3.55 (m, 2H); 3.81 (t, J=5.31, 2H); 4.00 (s, 3H); 4.13 (s, 3H); 4.29 (t, J=5.25, 2H); 6.69 (m, 1H); 7.40-7.51 (m, 2H); 7.60 (d, J=8.61, 1H); 7.68 (d, J=1.5, 1H); 7.70-7.80 (m, 2H); 8.27 (m, 2H).

EXAMPLE 127

3-(2,4-Dichlorophenyl)-6-[5-(2-ethoxyethoxymethyl)-1-methyl-1H-pyrazol-3-yl]-1,9-dimethyl-1,9-dihydropyrido[2,3-b]indol-2-one The process is carried out as in Example 101 above, with the compound from Example 82, 3-(2,4-dichlorophenyl)-6-(5-hydroxymethyl-1-methyl-1H-pyrazol-3-yl)-1,9-dimethyl-1,9-dihydropyrido[2,3-b]indol-2-one and 2-chloroethyl ethyl ether.

1H NMR DMSO-d6 (300 MHz): 1.10 (t, J=6.99, 3H); 3.45 (q, J=6.99, 2H); 3.53 (m, 4H); 4.83 (s, 3H); 4.02 (s, 3H); 4.16 (s, 3H); 4.56 (s, 2H); 6.70 (s, 1H); 7.47 (m, 2H); 7.61 (d, J=8.7, 1H); 7.72 (m, 2H); 8.28 (s, 2H).
Mp: 82° C.-86° C.

EXAMPLE 128

3-(2,4-Dichlorophenyl)-1,9-dimethyl-6-{2-[(2-morpholin-4-yl-ethylamino)methyl]thiazol-4-yl}-1,9-dihydropyrido[2,3-b]indol-2-one hydrochloride A) Compound A: 6-(2-Chloromethylthiazol-4-yl)-3-(2,4-dichlorophenyl)-1,9-dimethyl-1,9-dihydropyrido[2,3-b]indol-2-one The process is carried out as for Example 122A, with the compound from Example 9, 3-(2,4-dichlorophenyl)-6-(2-hydroxymethylthiazol-4-yl)-1,9-dimethyl-1,9-dihydropyrido[2,3-b]indol-2-one
1H NMR DMSO-d6 (300 MHz): 4.01 (s, 3H); 4.18 (s, 3H); 5.16 (s, 2H); 7.45 (m, 2H); 7.66-7.69 (m, 2H); 7.90 (sd, J=1.7, J=8.6, 1H); 8.07 (s, 1H); 8.28 (s, 1H); 8.47 (d, J=1.5, 1H).

B) 3-(2,4-Dichlorophenyl)-1,9-dimethyl-6-{2-[(2-morpholin-4-yl-ethylamino)-methyl]thiazol-4-yl}-1,9-dihydropyrido[2,3-b]indol-2-one hydrochloride The process is carried out as in Example 122 above, with the compound A: 6-(2-chloromethylthiazol-4-yl)-3-(2,4-dichlorophenyl)-1,9-dimethyl-1,9-dihydropyrido[2,3-b]indol-2-one and aminoethylmorpholine.
Mp=205-210° C. (decomp.)
1H NMR DMSO-d6 (300 MHz): 3.53-3.64 (m, 8H); 3.75-3.92 (m, 4H); 4.02 (s, 3H); 4.19 (s, 3H); 4.70 (s, 2H); 7.43-7.46 (m, 2H); 7.68-7.71 (m, 2H); 7.98 (d, J=8.9, 1H); 8.11 (s, 1H); 8.25 (s, 1H); 8.62 (s, 1H); 10.05 (m, 1H).

EXAMPLE 129

3-(2,4-Dichlorophenyl)-6-[1-(2-methoxyethoxymethyl)-1H-pyrazol-3-yl]-1,9-dimethyl-1,9-dihydropyrido[2,3-b]indol-2-one The process is carried out as in Example 10 above, with the compound from Example 39 3-(2,4-dichlorophenyl)-1,9-dimethyl-6-(1H-pyrazol-5-yl)-1,9-dihydro-2H-pyrido[2,3-b]indol-2-one and methoxyethoxymethyl chloride.
1H NMR DMSO-d6 (300 MHz): 3.18 (s, 3H); 3.37-3.40 (m, 2H); 3.57-3.61 (m, 2H); 3.98 (s, 3H); 4.14 (s, 3H); 5.44 (s, 2H); 6.77 (s, 1H); 7.40-7.43 (m, 2H); 7.59 (d, J=8.6, 1H); 7.65 (s, 1H); 7.75 (d, J=8.5, 1H); 7.90 (d, J=2.2, 1H); 8.26 (s, 1H); 8.30 (s, 1H).
Mp=162-163° C.

EXAMPLE 130

3-(2,4-Dichlorophenyl)-1,9-dimethyl-6-(2-morpholin-4-ylmethyl-thiazol-4-yl)-1,9-dihydropyrido[2,3-b]indol-2-one The process is carried out as in Example 122 above, with the compound from Example 128A 6-(2-chloromethylthiazol-4-yl)-3-(2,4-dichlorophenyl)-1,9-dimethyl-1,9-dihydropyrido[2,3-b]indol-2-one and morpholine.

1H NMR DMSO-d6 (300 MHz): 2.54 (m, 4H); 3.60-3.63 (m, 4H); 3.88 (s, 2H); 4.01 (s, 3H); 4.17 (s, 3H); 7.42-7.49 (m, 2H); 7.63-7.68 (m, 2H); 7.87 (d, J=8.6, 1H); 7.93 (s, 1H); 8.27 (s, 1H); 8.44 (s, 1H).
Mp=213-214° C.

EXAMPLE 131

3-(4-Chlorophenyl)-1,9-dimethyl-6-(4-methyl-2H-pyrazol-3-yl)-1,9-dihydropyrido[2,3-b]indol-2-one A) Compound A: 3-(4-Chlorophenyl)-1,9-dimethyl-6-propionyl-1,9-dihydropyrido[2,3-b]indol-2-one The process is carried out as indicated in preparation 1.9B above, with the compound from Example 104A 3-(4-chlorophenyl)-1,9-dimethyl-1,9-dihydro-1H-pyrido[2,3-b]indol-2-one and propionyl chloride.
1H NMR DMSO-d6 (300 MHz): 1.13 (t, J=7.2, 3H); 3.10 (q, J=7.2, 2H); 4.00 (s, 3H); 4.15 (s, 3H); 7.41 (d, J=8.5, 2H); 7.65 (d, J=8.7, 1H); 7.83-7.90 (m, 3H); 8.60 (s, 1H); 8.66 (s, 1H).

B) Compound B: 6-(-3-Dimethylamino-2-methylacryloyl)-3-(4-chlorophenyl)-1,9-dimethyl-1,9-dihydropyrido[2,3-b]indol-2-one The process is carried out as indicated in preparation 1.9C above, with compound A, 3-(4-chlorophenyl)-1,9-dimethyl-6-propionyl-1,9-dihydropyrido[2,3-b]indol-2-one and Bredereck's reagent.
1H NMR DMSO-d6 (300 MHz): 2.03 (s, 3H); 2.97 (s, 6H); 3.99 (s, 3H); 4.12 (s, 3H); 6.99 (s, 1H); 7.25 (sd, J=1.5, J=8.4, 1H); 7.40 (d, J=8.6, 2H); 7.54 (d, J=8.5, 1H); 7.80 (d, J=8.6, 2H); 7.95 (d, J=1.2, 1H); 8.54 (s, 1H).

C) 3-(4-Chlorophenyl)-1,9-dimethyl-6-(4-methyl-2H-pyrazol-3-yl)-1,9-dihydropyrido[2,3-b]indol-2-one The process is carried out as indicated in Example 36 above, with compound B, 6-(3-dimethylamino-2-methylacryloyl)-3-(4-chlorophenyl)-1,9-dimethyl-1,9-dihydropyrido[2,3-b]indol-2-one and hydrazine hydrate.
1H NMR DMSO-d6 (300 MHz): 2.25 (s, 3H); 4.02 (s, 3H); 4.15 (s, 3H); 7.21-7.56 (m, 4H); 7.65 (d, J=8.6, 1H); 7.83 (d, J=8.6, 2H); 8.15 (s, 1H); 8.53 (s, 1H).
Mp=271-273° C.

EXAMPLE 132

3-(4-Chlorophenyl)-6-(1-methoxymethyl-4-methyl-1H-pyrazol-3-yl)-1,9-dimethyl-1,9-dihydropyrido[2,3-b]indol-2-one The process is carried out as indicated in Example 36 above, with the compound from Example 131, 3-(4-chlorophenyl)-1,9-dimethyl-6-(4-methyl-2H-pyrazol-3-yl)-1,9-dihydropyrido[2,3-b]indol-2-one and bromomethyl methyl ether.
1H NMR DMSO-d6 (300 MHz): 2.27 (s, 3H); 3.29 (s, 3H); 4.03 (s, 3H); 4.16 (s, 3H); 5.35 (s, 2H); 7.43 (d, J=8.6, 2H); 7.58-7.66 (m, 2H); 7.76 (s, 1H); 7.85 (d, J=8.6, 2H); 8.21 (s, 1H); 8.58 (s, 1H).
Mp=205-207° C.

EXAMPLE 133

6-(1-Ethyl-1H-pyrazol-3-yl)-3-(4-fluorophenyl)-1,9-dimethyl-1,9-dihydropyrido[2,3-b]indol-2-one The process is carried out as indicated in Example 36 above, with the compound from Example 72, 3-(4-fluorophenyl)-1,9-dimethyl-6-(2H-pyrazol-3-yl)-1,9-dihydropyrido[2,3-b]indol-2-one and iodoethane.
1H NMR DMSO-d6 (300 MHz): 1.40 (t J=7.2, 3H); 3.99 (s, 3H); 4.11-4.18 (m, 5H); 6.67 (d, J=2.1, 1H); 7.16-7.22 (m, 2H); 7.55 (d, J=8.6, 1H); 7.70-7.84 (m, 4H); 8.33 (s, 1H); 8.47 (s, 1H).
Mp=178-182° C.

EXAMPLE 134

3-[3-(2,4-Dichlorophenyl)-1,9-dimethyl-2-oxo-2,9-dihydro-1H-pyrido[2,3-b]indol-6-yl]pyrazole-1-carboxylic acid 2-methoxyethyl ester The process is carried out as indicated in Example 99 above, with the compound from Example 39, 3-(2,4-dichlorophenyl)-1,9-dimethyl-6-(2H-pyrazol-3-yl)-1,9-dihydropyrido[2,3-b]indol-2-one and 2-methoxyethyl chloroformate.
Mp: 151-153° C.
MS: 524.95
1H NMR DMSO-d6 (300 MHz): 3.31 (s, 3H); 3.70 (t, J=4.5, 2H); 4.02 (s, 3H); 4.19 (s, 3H); 4.55 (t, J=4.2, 2H); 7.11 (d, J=2.79, 1H); 7.40-7.50 (m, 2H); 7.70 (m, 2H); 7.87 (d, J=8.7, 1H); 8.32 (s, 1H); 8.40 (d, J=2.76, 1H); 8.46 (s, 1H).

EXAMPLE 135

3-[3-(2,4-Dichlorophenyl)-1,9-dimethyl-2-oxo-2,9-dihydro-1H-pyrido[2,3-b]indol-6-yl]pyrazole-1-carboxylic acid isopropylamide 100 mg (0.24 mmol) of compound from Example 39, 3-(2,4-dichlorophenyl)-1,9-dimethyl-6-(2H-pyrazol-3-yl)-1,9-dihydropyrido[2,3-b]indol-2-one, are dissolved in 4 ml of chloroform. 232 μl (2.36 mmol) of isopropyl isocyanate are added and the mixture is then refluxed for 16 hours. The reaction medium is left to cool and then Et2O is added, and the mixture is filtered and washed with a minimum amount of Et2O.
96 mg of white powder are obtained.
Mp: 251-253° C.
MS: 508.044
1H NMR DMSO-d6 (300 MHz): 1.25 (d, J=6.51, 6H); 4.02 (s, 4H); 4.19 (s, 3H); 7.01 (d, J=2.49, 1H); 7.40-7.55 (m, 2H); 7.60-7.75 (m, 2H); 7.96 (d, J=7.83, 1H); 8.09 (d, J=8.25, 1H); 8.23 (s, 1H); 8.32 (d, J=2.49, 1H); 8.47 (s, 1H).

EXAMPLE 136

3-[3-(2,4-Dichlorophenyl)-1,9-dimethyl-2-oxo-2,9-dihydro-1H-pyrido[2,3-b]indol-6-yl]pyrazole-1-carboxylic acid 2,2-dimethylpropyl ester The process is carried out as indicated in Example 99 above, with the compound from Ex 39, 3-(2,4-dichlorophenyl)-1,9-dimethyl-6-(2H-pyrazol-3-yl)-1,9-dihydro-pyrido[2,3-b]indol-2-one and neopentyl chloroformate.
Mp: 170-172° C.
MS: 537.19

1H NMR DMSO-d6 (300 MHz): 1.02 (s, 9H); 4.02 (s, 3H); 4.13 (s, 2H); 4.19 (s, 3H); 7.12 (d, J=2.88, 1H); 7.40-7.51 (m, 2H); 7.65-7.75 (m, 2H); 7.89 (sd, J=8.58, J=1.59, 1H); 8.31 (s, 1H); 8.42 (d, J=2.85, 1H); 8.46 (d, J=1.35, 1H).

EXAMPLE 137

3-(2,4-Dichlorophenyl)-6-[1-(2,2-dimethylpropionyl)-1H-pyrazol-3-yl]-1,9-dimethyl-1,9-dihydropyrido[2,3-b]indol-2-one The process is carried out as indicated in Example 99 above, with the compound from Ex 39, 3-(2,4-dichlorophenyl)-1,9-dimethyl-6-(2H-pyrazol-3-yl)-1,9-dihydro-pyrido[2,3-b]indol-2-one and pivaloyl chloride.

1H NMR DMSO-d6 (300 MHz): 1.52 (s, 9H); 4.01 (s, 3H); 4.17 (s, 3H); 7.07 (s, 1H); 7.42-7.45 (m, 2H); 7.67-7.71 (m, 2H); 7.87 (d, J=8.5, 1H); 8.30 (s, 1H); 8.40-8.45 (m, 2H).
Mp=245-246° C.

EXAMPLE 138

3-(2,4-Dichlorophenyl)-6-(1-methanesulphonyl-1H-pyrazol-3-yl)-1,9-dimethyl-1,9-dihydropyrido[2,3-b]indol-2-one The process is carried out as indicated in Example 99 above with the compound from Example 39, 3-(2,4-dichlorophenyl)-1,9-dimethyl-6-(2H-pyrazol-3-yl)-1,9-dihydro-pyrido[2,3-b]indol-2-one, and methanesulphonyl chloride.

1H NMR DMSO-d6 (300 MHz): 3.56 (s, 3H); 3.99 (s, 3H); 4.16 (s, 3H); 7.09 (s, 1H); 7.40-7.47 (m, 2H); 7.65-7.70 (m, 2H); 7.85 (d, J=8.5, 1H); 8.28 (s, 1H); 8.30 (d, J=2.8, 1H); 8.45 (s, 1H).
Mp=267-268° C. (decomp.)

EXAMPLE 139

3-(2,4-Dichlorophenyl)-6-[2-(1-hydroxy-1-methylethyl)thiazol-4-yl]-1,9-dimethyl-1,9-dihydropyrido[2,3-b]indol-2-one The process is carried out as indicated in Example 21 above, using compound from preparation 1.2, 6-(bromoacetyl)-3-(2,4-dichlorophenyl)-1,9-dimethyl-1,9-dihydro-2H-pyrido[2,3-b]indol-2-one and ethylthiooxamate.

1H NMR DMSO-d6 (300 MHz): 1.36 (t, J=7.11, 3H); 4.02 (s, 3H); 4.20 (s, 3H); 4.42 (q, J=7.11, 2H); 7.48 (m, 2H); 7.65-7.75 (m, 2H); 7.94 (sd, J=8.61, 1H=1.65, 1H); 8.31 (s, 1H); 8.43 (s, 1H); 8.52 (d, J=1.44, 1H).

B): 3-(2,4-Dichlorophenyl)-6-[2-(1-hydroxy-1-methylethyl)thiazol-4-yl]-1,9-dimethyl-1,9-dihydropyrido[2,3-b]indol-2-one 131 mg (0.25 mmol) of compound A 4-[3-(2,4-dichlorophenyl)-1,9-dimethyl-2-oxo-2,9-dihydro-1H-pyrido[2,3-b]indol-6-yl]thiazole-2-carboxylic acid ethyl ester are dissolved in 5 ml of 1.4M methylmagnesium bromide in toluene. The solution is stirred at ambient temperature for 3 days. It is concentrated to dryness, adsorbing onto silica. Purification is carried out on a silica column, elution being carried out with 100% CH2Cl2 and then CH2Cl2/3% MeOH. The residue is taken up in MeOH, and the product is filtered and washed with MeOH.

54 mg of light beige powder are obtained.
Yield: 42%

Mp: 268-269° C.
MS: 497.95
1H NMR DMSO-d6 (300 MHz): 1.58 (s, 6H); 4.01 (s, 3H); 4.17 (s, 3H); 5.99 (s, 1H); 7.46 (m, 2H); 7.66 (m, 2H); 7.83 (s, 1H); 7.88 (d, J=8.61, 1H); 8.28 (s, 1H); 8.44 (s, 1H).

EXAMPLE 140

6-(2-Cyclohexyl-2H-pyrazol-3-yl)-3-(2,4-dichlorophenyl)-1,9-dimethyl-1,9-dihydropyrido[2,3-b]indol-2-one The process is carried out as in Example 37 above, with the compound from preparation 1.10, 3-(2,4-dichlorophenyl)-6-[3-(dimethylamino)prop-2-enoyl]-1,9-dimethyl-1,9-dihydro-2H-pyrido[2,3-b]indol-2-one and cyclohexylhydrazine hydrochloride.

Mp: 238-240° C.
MS: 505.17
1H NMR DMSO-d6 (300 MHz): 1.17 (bs, 3H); 1.58 (bs, 1H); 1.73 (bs, 2H); 1.85 (bs, 4H); 4.03 (s, 3H); 4.10 (m, 1H); 4.20 (s, 3H); 6.28 (d, J=1.56, 1H); 7.28 (d, J=8.43, 1H); 7.40-7.55 (m, 3H); 7.68 (d, J=1.83, 1H); 7.74 (d, J=8.52, 1H); 7.93 (s, 1H); 8.31 (s, 1H).

EXAMPLE 141

3-(4-Chloro-2-fluorophenyl)-1,9-dimethyl-6-(2H-pyrazol-3-yl)-1,9-dihydropyrido[2,3-b]indol-2-one A) Compound A: 3-(4-Chloro-2-fluorophenyl)-1,9-dimethyl-1,9-dihydropyrido[2,3-b]indol-2-one The process is carried out as indicated in preparation 1.2B above, with methyl-(1-methyl-1H-indol-2-yl)amine hydrochloride (prepared according to the procedures described in WO 2004/041817) and 2-(4-chloro-2-fluorophenyl)-3-dimethylamino-acrylic acid methyl ester B) Compound B: 6-Acetyl-3-(4-chloro-2-fluorophenyl)-1,9-dimethyl-1,9-dihydropyrido[2,3-b]indol-2-one The process is carried out as indicated in preparation 1.9B above, with compound A 3-(4-chloro-2-fluorophenyl)-1,9-dimethyl-1,9-dihydropyrido[2,3-b]indol-2-one and acetyl chloride.

1H NMR DMSO-d6 (300 MHz): 2.63 (s, 3H); 4.02 (s, 3H); 4.19 (s, 3H); 7.34 (sd, J=8.28, J=2.19, 1H); 7.47 (dd, J=10.05, J=2.07, 1H); 7.55 (t, J=8.20, 1H); 7.72 (d, J=8.73, 1H); 7.90 (sd, J=8.67, J=1.68, 1H); 8.46 (s, 1H); 8.63 (d, J=1.5, 1H).

C) Compound C: 3-(4-Chloro-2-fluorophenyl)-6-(3-dimethylaminoacryloyl)-1,9-dimethyl-1,9-dihydropyrido[2,3-b]indol-2-one The process is carried out as indicated in preparation 1.9C above, with compound B 6-acetyl-3-(4-chloro-2-fluorophenyl)-1,9-dimethyl-1,9-dihydropyrido[2,3-b]indol-2-one and Bredereck's reagent.
MS: 437.99

D) 3-(4-Chloro-2-fluorophenyl)-1,9-dimethyl-6-(2H-pyrazol-3-yl)-1,9-dihydro-pyrido[2,3-b]indol-2-one The process is carried out as indicated in Example 36 above, with compound $C_3$-(4-chloro-2-fluorophenyl)-6-(3- dimethylaminoacryloyl)-1,9-dimethyl-1,9-dihydropyrido-[2,3-b]indol-2-one and hydrazine monohydrate.

Mp: 325-326° C.

MS: 406.78

1H NMR DMSO-d6 (300 MHz): 4.01 (s, 3H); 4.15 (s, 3H); 6.72 (s, 1H); 7.34 (sd, J=8.4, J=1.8, 1H); 7.47 (sd, J=9.9, J=1.8, 1H); 7.55 (t, J=8.4, 1H); 7.62 (m, 1H); 7.77 (bs, 2H); 8.32 (s, 2H); 12.80-13.20 (bs, 1H).

EXAMPLE 142

3-(4-Chloro-2-fluorophenyl)-6-(1-ethyl-1H-pyrazol-3-yl)-1,9-dimethyl-1,9-dihydropyrido[2,3-b]indol-2-one The process is carried out as in Example 110 above, using compound from Example 141, 3-(4-chloro-2-fluorophenyl)-1,9-dimethyl-6-(2H-pyrazol-3-yl)-1,9-dihydro-pyrido[2,3-b]indol-2-one and iodoethane.

Mp: 215-217° C.

MS: 435.20

1H NMR DMSO-d6 (300 MHz): 1.42 (t, J=7.23, 3H); 4.00 (s, 3H); 4.15 (s, 3H); 4.18 (m, 2H); 6.69 (d, J=2.19, 1H); 7.33 (sd, J=8.28, J=1.83, 1H); 7.46 (sd, J=10.02, J=1.92, 1H); 7.51-7.65 (m, 2H); 7.76 (m, 2H); 8.30 (s, 1H); 8.36 (s, 1H).

EXAMPLE 143

3-(2,4-Dichlorophenyl)-6-[2-(2-methoxyethyl)-2H-pyrazol-3-yl]-1,9-dimethyl-1,9-dihydropyrido[2,3-b]indol-2-one A) Compound A: 3-(2,4-Dichlorophenyl)-6-[2-(2-hydroxyethyl)-2H-pyrazol-3-yl]-1,9-dimethyl-1,9-dihydropyrido[2,3-b]indol-2-one The process is carried out as in Example 37 above, with the compound from preparation 1.10, 3-(2,4-dichlorophenyl)-6-[3-(dimethylamino)prop-2-enoyl]-1,9-dimethyl-1,9-dihydro-2H-pyrido[2,3-b]indol-2-one and 2-hydroxyethylhydrazine

MS: 466.85

B) 3-(2,4-Dichlorophenyl)-6-[2-(2-methoxyethyl)-2H-pyrazol-3-yl]-1,9-dimethyl-1,9-dihydropyrido[2,3-b]indol-2-one The process is carried out as in Example 101 above, with compound A, 3-(2,4-dichlorophenyl)-6-[2-(2-hydroxyethyl)-2H-pyrazol-3-yl]-1,9-dimethyl-1,9-dihydropyrido[2,3-b]indol-2-one and iodomethane.

Mp: 150-154° C.

MS: 481.00

1H NMR DMSO-d6 (300 MHz): 3.11 (s, 3H); 3.68 (t, J=5.52, 2H); 4.03 (s, 3H); 4.20 (s, 3H); 4.27 (t, J=5.61, 2H); 6.35 (d, J=1.8, 1H); 7.38-7.50 (m, 3H); 7.52 (d, J=1.77, 1H); 7.68 (d, J=1.83, 1H); 7.74 (d, J=8.52, 1H); 8.02 (d, J=1.38, 1H); 8.26 (s, 1H).

EXAMPLE 144

3-(2,4-dichlorophenyl)-6-(1-ethoxymethyl-1H-pyrazol-3-yl)-1,9-dimethyl-1,9-dihydropyrido[2,3-b]indol-2-one The process is carried out as in Example 36 above with the compound from Example 39, 3-(2,4-dichlorophenyl)-1,9-dimethyl-6-(1H-pyrazol-3-yl)-1,9-dihydropyrido[2,3-b]indol-2-one and chloromethyl ethyl ether.

1H NMR DMSO-d6 (300 MHz): 1.09 (t, J=7.0, 3H); 3.52 (q, J=7.0, 2H); 4.02/4.03 (S/s, 3H); 4.17/4.20 (S/s, 3H); 5.45 (s, 2H); 6.51/6.80 (s/S, 1H); 7.45-7.78 (m, 5H); 7.94/8.10 (S/s, 1H), 8.22-8.34 (m, 2H).

Mp=183° C.-189° C.

EXAMPLE 145

6-(1-Acetyl-1H-pyrazol-3-yl)-3-(2,4-dichlorophenyl)-1,9-dimethyl-1,9-dihydropyrido[2,3-b]indol-2-one The process is carried out as in Example 99 above, with the compound from Example 39, 3-(2,4-dichlorophenyl)-1,9-dimethyl-6-(1H-pyrazol-3-yl)-1,9-dihydropyrido[2,3-b]indol-2-one and acetyl chloride.

1H NMR DMSO-d6 (300 MHz): 2.72 (s, 3H); 4.02 (s, 3H); 4.19 (s, 3H); 7.15 (d, J=2.85, 1H); 7.47 (m, 2H); 7.71 (m, 2H); 7.91 (d, J=8.55, 1H); 8.31 (s, 1H); 8.47 (m, 2H).

Mp=256° C.-260° C. (decomp.)

EXAMPLE 146

6-(2-Aminomethylthiazol-4-yl)-3-(2,4-dichlorophenyl)-1,9-dimethyl-1,9-dihydropyrido[2,3-b]indol-2-one A) Compound A: {4-[3-(2,4-Dichlorophenyl)-1,9-dimethyl-2-oxo-2,9-dihydro-1H-pyrido[2,3-b]indol-6-yl]thiazol-2-ylmethyl}carbamic acid benzyl ester The process is carried out as for Example 8 above, using the compound from preparation 1.2, 6-(bromoacetyl)-3-(2,4-dichlorophenyl)-1,9-dimethyl-1,9-dihydro-2H-pyrido[2,3-b]indol-2-one and N-benzyloxycarbonylglycine thioamide.

1H NMR DMSO-d6 (300 MHz): 4.01 (s, 3H); 4.17 (s, 3H); 4.55 (d, J=6.15, 2H); 5.10 (s, 2H); 7.32-7.46 (m, 7H); 7.67 (m, 2H); 7.88 (m, 2H); 8.25 (s, 2H); 8.44 (s, 1H).

B) 6-(2-Aminomethylthiazol-4-yl)-3-(2,4-dichlorophenyl)-1,9-dimethyl-1,9-dihydropyrido[2,3-b]indol-2-one 780 mg (1.3 mmol) of compound A {4-[3-(2,4-dichlorophenyl)-1,9-dimethyl-2-oxo-2,9-dihydro-1H-pyrido[2,3-b]indol-6-yl]thiazol-2-ylmethyl}carbamic acid benzyl ester are dissolved in 12 ml of trifluoroacetic acid. 8 ml (10.3 mmol) of thioanisole are added and the mixture is stirred at ambient temperature for 16 hours. It is poured into a saturated K2CO3 solution and the mixture is extracted with EtOAc. The organic phase is adsorbed onto silica and purification is carried out on a silica column, elution being carried out with EtOAc and then with 90/10/1 EtOAc/MeOH/NH3.

100 mg of pale yellow powder are obtained.

1H NMR DMSO-d6 (300 MHz): 4.01 (s, 3H); 4.07 (s, 2H); 4.17 (s, 3H); 7.47 (m, 2H); 7.67 (m, 2H); 7.87 (m, 2H); 8.27 (s, 1H); 8.44 (s, 1H).

Mp=176° C.-180° C.

EXAMPLE 147

N-{4-[3-(2,4-Dichlorophenyl)-1,9-dimethyl-2-oxo-2,9-dihydro-1H-pyrido[2,3-b]indol-6-yl]thiazol-2-ylmethyl}methanesulphonamide The process is carried out as indicated in Example 99 above, with the compound from Example 147, 6-(2-aminomethylthiazol-4-yl)-3-(2,4-dichlorophenyl)-1,9-dimethyl-1,9-dihydropyrido[2,3-b]indol-2-one, and methanesulphonyl chloride.

1H NMR DMSO-d6 (300 MHz): 3.03 (s, 3H); 4.02 (s, 3H); 4.19 (s, 3H); 4.54 (s, 2H); 7.47 (m, 2H); 7.69 (m, 2H); 7.90 (sd, J=1.8, J=8.7, 1H); 7.96 (s, 1H); 8.10 (bs, 1H); 8.28 (s, 1H); 8.46 (s, 1H).
Mp=164° C.-169° C.

EXAMPLE 148

3-(2,4-Dichlorophenyl)-6-(2-methoxymethoxymethylthiazol-4-yl)-1,9-dimethyl-1,9-dihydropyrido[2,3-b]indol-2-one The process is carried out as indicated in Example 10 above, with the compound from Example 9, 3-(2,4-dichlorophenyl)-6-(2-hydroxymethylthiazol-4-yl)-1,9-dimethyl-1,9-dihydropyrido[2,3-b]indol-2-one, and bromomethyl methyl ether.
Mp=160-164° C.
1H NMR DMSO-d6 (300 MHz): 3.28 (s, 3H); 3.35 (s, 2H); 4.01 (s, 3H); 4.17 (s, 3H); 4.83 (m, 2H); 7.43-7.46 (m, 2H); 7.65-7.68 (m, 2H); 7.88-7.91 (sd, J=1.5, 8.6, 1H); 7.99 (s, 1H); 8.28 (s, 1H); 8.46 (d, J=1.2, 1H).

EXAMPLE 149

6-(2-Cyclopropylmethoxymethylthiazol-4-yl)-3-(2,4-dichlorophenyl)-1,9-dimethyl-1,9-dihydropyrido[2,3-b]indol-2-one The process is carried out as indicated in Example 10 above, with the compound from Example 9, 3-(2,4-dichlorophenyl)-6-(2-hydroxymethylthiazol-4-yl)-1,9-dimethyl-1,9-dihydropyrido[2,3-b]indol-2-one, and bromomethylcyclopropane.
1H NMR DMSO-d6 (300 MHz): 0.20-0.25 (m, 2H); 0.49-0.52 (m, 2H); 1.03-1.11 (m, 1H); 3.43 (d, J=6.8, 2H); 4.01 (s, 3H); 4.17 (s, 3H); 4.83 (s, 2H); 7.43-7.46 (m, 2H); 7.65-7.68 (m, 2H); 7.89 (sd, J=1.6, J=8.6, 1H); 7.97 (s, 1H); 8.27 (s, 1H); 8.46 (d, J=1.4, 1H).

EXAMPLE 150

3-(2,4-Dichlorophenyl)-6-[2-(2-methoxyethylamino)thiazol-4-yl]-1,9-dimethyl-1,9-dihydropyrido[2,3-b]indol-2-one The process is carried out as for Example 21 above, using the compound from preparation 1.2, 6-(bromoacetyl)-3-(2,4-dichlorophenyl)-1,9-dimethyl-1,9-dihydro-2H-pyrido[2,3-b]indol-2-one and 1-(2-methoxyethyl)-2-thiourea.

1H NMR DMSO-d6 (300 MHz): 3.30 (s, 3H); 3.53 (m, 4H); 4.01 (s, 3H); 4.16 (s, 3H); 6.94 (s, 1H); 7.46 (m, 2H); 7.56-7.80 (m, 4H); 8.23 (s, 1H); 8.32 (s, 1H).

EXAMPLE 151

3-(2,4-Dichlorophenyl)-9-difluoromethyl-6-(2-ethyl-2H-pyrazol-3-yl)-1-methyl-1,9-dihydropyrido[2,3-b]indol-2-one A) Compound A: 6-Acetyl-3-(2,4-dichlorophenyl)-9-difluoromethyl-1-methyl-1,9-dihydropyrido[2,3-b]indol-2-one 460 mg (1.19 mmol) of compound from preparation 1.9A, 6-acetyl-3-(2,4-dichlorophenyl)-1-methyl-1,9-dihydro-2H-pyrido[2,3-b]indol-2-one, are dissolved in 7 ml of DMF and 2 ml of water. 543 mg (1.67 mmol) of caesium carbonate and 419 mg (2.75 mmol) of sodium chlorodifluoroacetate are added. The mixture is heated at 100° C. for 48 hours. It is allowed to return to ambient temperature. The reaction medium is poured into water, and the precipitate formed is filtered off and washed with water. The product is taken up in an EtOAc/MeOH mixture and adsorbed onto silica. Purification is carried out on a silica column, elution being carried out with a 50/50 EtOAc/cyclohexane mixture and then with EtOAc.
170 mg of beige powder are obtained.
1H NMR DMSO-d6 (300 MHz): 2.65 (s, 3H); 3.87 (s, 3H); 7.50 (m, 2H); 7.73 (d, J=2.1, 1H); 7.89 (m, 2H); 8.40 (t, J=59, 1H); 8.51 (s, 1H); 8.69 (s, 1H).

B) Compound B: 3-(2,4-Dichlorophenyl)-9-difluoromethyl-6-((E)-3-dimethylamino-acryloyl)-1-methyl-1,9-dihydropyrido[2,3-b]indol-2-one The process is carried out as for preparation 1.10 above, using compound A: 6-acetyl-3-(2,4-dichlorophenyl)-9-difluoromethyl-1-methyl-1,9-dihydropyrido[2,3-b]indol-2-one and Bredereck's reagent.

C) 3-(2,4-Dichlorophenyl)-9-difluoromethyl-6-(2-ethyl-2H-pyrazol-3-yl)-1-methyl-1,9-dihydropyrido[2,3-b]indol-2-one The process is carried out as indicated in Example 37 above, with compound B, 3-(2,4-dichlorophenyl)-9-difluoromethyl-6-((E)-3-dimethylaminoacryloyl)-1-methyl-1,9-dihydropyrido[2,3-b]indol-2-one, and ethylhydrazine oxalate.
1H NMR DMSO-d6 (300 MHz): 1.29 (t, J=7.2, 3H); 3.88 (s, 3H); 4.17 (d, J=7.2, 2H); 6.38 (s, 1H); 7.44 (m, 4H); 7.72 (d, J=2.1, 1H); 7.86 (d, J=8.1, 1H); 8.09 (d, J=1.5, 1H); 8.40 (t, J=60, 1H); 8.44 (s, 1H).

EXAMPLE 152

3-(2,4-Dichlorophenyl)-6-[2-(1-hydroxyethyl)thiazol-4-yl]-1,9-dimethyl-1,9-dihydropyrido[2,3-b]indol-2-one A) Compound A: 4-[3-(2,4-Dichlorophenyl)-1,9-dimethyl-2-oxo-2,9-dihydro-1H-pyrido[2,3-b]indol-6-yl]thiazole-2-carbaldehyde 258 mg (0.548 mmol) of compound from Example 9, 3-(2,4-dichlorophenyl)-6-(2-hydroxymethylthiazol-4-yl)-1,9-dimethyl-1,9-dihydropyrido[2,3-b]indol-2-one are suspended in 10 ml of CHCl3. 177 mg (0.82 mmol) of pyridinium chlorochromate (PCC) are added. The mixture is stirred at ambient temperature for 3 hours. The reaction medium is loaded directly onto a silica column and the mixture is purified, elution being carried out with 100% EtOAc.
163 mg of yellow powder are obtained.
MS: 468.01
1H NMR DMSO-d6 (300 MHz): 4.02 (s, 3H); 4.20 (s, 3H); 7.47 (m, 2H); 7.69 (s, 1H); 7.74 (d, J=8.64, 1H); 8.00 (d, J=8.55, 1H); 8.30 (s, 1H); 8.59 (s, 2H); 10.03 (s, 1H).

B) 3-(2,4-Dichlorophenyl)-6-[2-(1-hydroxyethyl)thiazol-4-yl]-1,9-dimethyl-1,9-dihydropyrido[2,3-b]indol-2-one The process is carried out as indicated in Example 139 above, with compound A, 4-[3-(2,4-dichlorophenyl)-1,9- dimethyl-2-oxo-2,9-dihydro-1H-pyrido[2,3-b]indol-6-yl]-thiazole-2-carbaldehyde, and methylmagnesium bromide.

Mp: 280-285° C.
MS: 484.3
1H NMR DMSO-d6 (300 MHz): 1.51 (d, J=6.45, 3H); 4.00 (s, 3H); 4.16 (s, 3H); 4.99 (m, 1H); 6.15 (d, J=4.89, 1H); 7.45 (m, 2H); 7.67 (m, 2H); 7.87 (m, 2H); 8.26 (s, 1H); 8.44 (d, J=1.29, 1H).

EXAMPLE 153

3-(2,4-Dichlorophenyl)-6-(2-fluoromethylthiazol-4-yl)-1,9-dimethyl-1,9-dihydropyrido[2,3-b]indol-2-one 150 mg (0.319 mmol) of compound from Example 9, 3-(2,4-dichlorophenyl)-6-(2-hydroxymethylthiazol-4-yl)-1,9-dimethyl-1,9-dihydropyrido[2,3-b]indol-2-one, are dissolved in 3 ml of CH2Cl2. 51 μl of (diethylamino)sulphur trifluoride (DAST) are added at 0° C. The mixture is stirred at 0° C. for 2 hours. A further 100 μl of DAST are added (presence of starting product) and the mixture is left to stir at ambient temperature for a further 16 hours. H2O is added, the mixture is extracted with CH2Cl2, and the organic phase is dried over MgSO4, filtered and concentrated to dryness, adsorbing onto silica. Purification is carried out on a silica column, elution being carried out with EtOAc/40% cyclohexane and then with EtOAc/30% cyclohexane. The residue is taken up in MeOH and the precipitate is filtered off, and washed with MeOH and then with a minimum amount of Et2O.

50 mg of pale yellow powder are obtained.
Mp: 259-260° C.
MS: 471.95
1H NMR DMSO-d6 (300 MHz): 3.99 (s, 3H); 4.15 (s, 3H); 5.66-5.81 (m, 2H); 7.43 (m, 2H); 7.66 (m, 2H); 7.89 (d, J=8.58, 1H); 8.11 (s, 1H); 8.26 (s, 1H); 8.47 (s, 1H).

EXAMPLE 154

3-(2,4-Dichlorophenyl)-6-(1-methoxymethyl-1H-[1,2,3]triazol-4-yl)-1,9-dimethyl-1,9-dihydropyrido[2,3-b]indol-2-one 209 mg (0.49 mmol) of compound from Example 47, 3-(2,4-dichlorophenyl)-1,9-dimethyl-6-(1H-[1,2,3]triazol-4-yl)-1,9-dihydropyrido[2,3-b]indol-2-one, are dissolved in 3 ml of DMF. 30 mg (0.74 mmol) of 60% NaH and a spatula tip of dibenzo-18-crown-6 are added. 80 μl of bromomethyl methyl ether are then added. The mixture is stirred at ambient temperature for 16 hours. The reaction medium is poured into water and then extracted with EtOAc and the organic phase is dried over MgSO4, filtered and evaporated to dryness, adsorbing onto silica. Purification is carried out on a silica column, elution being carried out with a gradient of EtOAc/50% cyclohexane, then with EtOAc/40% cyclohexane and, finally, 100% EtOAc. The residue is triturated in MeOH so as to obtain a beige solid.

28 mg of beige powder are obtained.
Mp: 173-176° C.
MS: 467.84
1H NMR DMSO-d6 (300 MHz): 3.28 (s, 3H); 3.99 (s, 3H); 4.16 (s, 3H); 5.64 (s, 2H); 7.44 (m, 2H); 7.66 (m, 1H); 7.70 (s, 1H); 7.78 (m, 1H); 8.26 (s, 1H); 8.31 (s, 1H); 8.40 (s, 1H).

EXAMPLE 155

3-[3-(2,4-Dichlorophenyl)-1,9-dimethyl-2-oxo-2,9-dihydro-1H-pyrido[2,3-b]indol-6-yl]pyrazole-1-sulphonic acid dimethylamide The process is carried out as indicated in Example 99 above, with the compound from Example 39, 3-(2,4-dichlorophenyl)-1,9-dimethyl-6-(2H-pyrazol-3-yl)-1,9-dihydropyrido[2,3-b]indol-2-one, and dimethyl sulphamoyl chloride.

1H NMR DMSO: 2.92 (s, 6H); 4.03 (s, 3H); 4.20 (s, 3H); 7.09 (d, J=3, 1H); 7.47 (m, 2H); 7.70 (m, 2H); 7.85 (sd, J=1.5, J=8.6, 1H); 8.31 (m, 1H); 8.45 (s, 1H).

EXAMPLE 156

3-(2,4-Dichlorophenyl)-6-[2-(1-fluoro-1-methylethyl)thiazol-4-yl]-1,9-dimethyl-1,9-dihydropyrido[2,3-b]indol-2-one The process is carried out as indicated in Example 153 above, with the compound from Example 139.

EXAMPLE 157

3-(2,4-Dichlorophenyl)-6-[2-(2-hydroxyethyl)-2H-pyrazol-3-yl]-1,9-dimethyl-1,9-dihydropyrido[2,3-b]indol-2-one The process is carried out as indicated in Example 37 above, with the compound from preparation 1.10 and 2-hydroxyethylhydrazine.

Mp: 204-206° C.
MS: 467.3
1H NMR DMSO-d6 (300 MHz): 3.75 (q, J=5.7, 2H); 4.03 (s, 3H); 4.16 (m, 2H); 4.20 (s, 3H); 4.91 (t, J=5.31, 1H); 6.35 (d, J=1.74, 1H); 7.40-7.50 (m, 3H); 7.51 (d, J=1.77, 1H); 7.69 (d, J=1.89, 1H); 7.72 (m, 1H); 8.05 (d, J=1.26, 1H); 8.26 (s, 1H).

EXAMPLE 158

3-(2,4-Dichlorophenyl)-1,9-dimethyl-6-{1-[2-(2-pyrrolidin-1-ylethoxy)ethyl]-1H-pyrazol-3-yl}-1,9-dihydropyrido[2,3-b]indol-2-one The process is carried out as indicated in Example 101 above, with the compound from Example 51 above, 3-(2,4-dichlorophenyl)-6-[1-(2-hydroxyethyl)-1H-pyrazol-3-yl]-1,9-dimethyl-1,9-dihydropyrido[2,3-b]indol-2-one, and 1-(2-chloroethyl)-pyrrolidine.

EXAMPLE 159

3-(2,4-Dichlorophenyl)-6-[1-(2-methoxyacetyl)-4-methyl-1H-pyrazol-3-yl]-1,9-dimethyl-1,9-dihydropyrido[2,3-b]indol-2-one The process is carried out as indicated in Example 70 above, with the compound from Example 53 3-(2,4-dichlorophenyl)-1,9-dimethyl-6-(4-methyl-2H-pyrazol-3-yl)-1,9-dihydropyrido[2,3-b]indol-2-one and methoxyacetyl chloride.

1H NMR DMSO-d6 (300 MHz): 2.3 (s, 3H); 3.42 (s, 3H); 4.03 (s, 3H); 4.20 (s, 3H); 4.92 (s, 2H); 7.43-7.50 (m, 2H); 7.68-7.75 (m, 3H); 8.25 (s, 1H); 8.30 (s, 1H); 8.38 (s, 1H).

EXAMPLE 160

3-(2,4-Dichlorophenyl)-6-[1-(2-methoxyacetyl)-1H-pyrazol-3-yl]-1,9-dimethyl-1,9-dihydropyrido[2,3-b]indol-2-one The process is carried out as indicated in Example 70 above, with the compound from Example 39 3-(2,4-dichlorophenyl)-1,9-dimethyl-6-(1H-pyrazol-3-yl)-1,9-dihydropyrido[2,3-b]indol-2-one and methoxyacetyl chloride.

1H NMR DMSO-d6 (300 MHz): 3.44 (s, 3H); 4.03 (s, 3H); 4.20 (s, 3H); 4.98 (s, 2H); 7.18 (d, J=2.7, 1H); 7.48 (m, 2H); 7.70 (m, 2H); 7.90 (sd, J=1.5, J=8.6, 1H); 8.31 (s, 1H); 8.50 (m, 2H).
Mp=243° C.-247° C.

EXAMPLE 161

3-(2,4-Dichlorophenyl)-9-difluoromethyl-6-(1-ethyl-1H-pyrazol-3-yl)-1-methyl-1,9-dihydropyrido[2,3-b]indol-2-one

A) Compound A: 3-(2,4-Dichlorophenyl)-9-difluoromethyl-1-methyl-6-(1H-pyrazol-3-yl)-1,9-dihydropyrido[2,3-b]indol-2-one The process is carried out as indicated in Example 40 above, with the compound from Example 151B, 3-(2,4-dichlorophenyl)-9-difluoromethyl-6-((E)-3-dimethylaminoacryloyl)-1-methyl-1,9-dihydropyrido[2,3-b]indol-2-one, and hydrazine monohydrate.

1H NMR DMSO-d6 (300 MHz): 3.86 (s, 3H); 6.75 (s, 1H); 7.51 (m, 2H); 7.74 (m, 4H); 8.35 (t, J=57, 1H); 8.41 (s, 2H); 12.89 (s, 1H).

B) 3-(2,4-Dichlorophenyl)-9-difluoromethyl-6-(1-ethyl-1H-pyrazol-3-yl)-1-methyl-1,9-dihydropyrido[2,3-b]indol-2-one The process is carried out as indicated in Example 110 above, with compound A, 3-(2,4-dichlorophenyl)-9-difluoromethyl-1-methyl-6-(1H-pyrazol-3-yl)-1,9-dihydropyrido[2,3-b]indol-2-one, and iodoethane.

EXAMPLE 162

2,2-Dimethylpropionic acid 5-[3-(2,4-dichlorophenyl)-1,9-dimethyl-2-oxo-2,9-dihydro-1H-pyrido[2,3-b]indol-6-yl]-2-methyl-2H-pyrazol-3-ylmethyl ester The process is carried out as indicated in Example 70 above, with the compound from Example 82, 3-(2,4-dichlorophenyl)-6-(5-hydroxymethyl-1-methyl-1H-pyrazol-3-yl)-1,9-dimethyl-1,9-dihydropyrido[2,3-b]indol-2-one, and pivaloyl chloride.

1H NMR DMSO-d6 (300 MHz): 1.17 (s, 9H); 3.86 (s, 3H); 4.01 (s, 3H); 4.16 (s, 3H); 5.18 (s, 2H); 6.76 (s, 1H); 7.47 (m, 2H); 7.62 (d, J=8.4, 1H); 7.72 (m, 2H); 8.29 (m, 2H).
Mp=145° C.-150° C.

EXAMPLE 163

6-[1-(2,2-Dimethylpropionyl)-4-methyl-1H-pyrazol-3-yl]-3-(4-fluorophenyl)-1,9-dimethyl-1,9-dihydropyrido[2,3-b]indol-2-one The process is carried out as indicated in Example 70 above, with the compound from Example 53, 3-(4-fluorophenyl)-1,9-dimethyl-6-(4-methyl-2H-pyrazol-3-yl)-1,9-dihydropyrido[2,3-b]indol-2-one, and pivaloyl chloride.

1H NMR DMSO-d6 (300 MHz): 1.48 (s, 9H); 2.28 (s, 3H); 4.00 (s, 3H); 4.13 (s, 3H); 7.16-7.22 (m, 2H); 7.66-7.79 (m, 4H); 8.22 (d, J=4.02, 2H); 8.50 (s, 1H).

EXAMPLE 164

3-(2,4-Dichlorophenyl)-1,9-dimethyl-6-[1-(3,3,3-trifluoropropionyl)-1H-pyrazol-3-yl]-1,9-dihydropyrido[2,3-b]indol-2-one The process is carried out as indicated in Example 70 above, with the compound from Example 39 3-(2,4-dichlorophenyl)-1,9-dimethyl-6-(1H-pyrazol-3-yl)-1,9-dihydropyrido[2,3-b]indol-2-one and 3,3,3-trifluoropropionyl chloride.

1H NMR DMSO-d6 (300 MHz): 4.03 (s, 3H); 4.20 (s, 3H); 4.57 (q, J=12.3, 2H); 7.26 (d, J=2.9, 1H); 7.48 (m, 2H); 7.71 (m, 2H); 7.94 (d, J=8.6, 1H); 8.30 (s, 1H); 8.56 (m, 2H).
Mp=262° C.-268° C. (decomp.)

The table which follows illustrates the chemical structures and the physical properties of some examples of compounds according to the invention.

TABLE I (I)

[Structure of compound I showing pyrido[2,3-b]indol-2-one core with 2,4-dichlorophenyl substituent, R4 and R1 groups, and N-CH3]

| Compounds No. | R₁ | R₄ | Mp ° C. NMR |
|---|---|---|---|
| 1 | H | [thiazole with CH₃] | >350 (decomp.) |
| 2 | H | [thiazole with NH₂] | >350 (decomp.) |
| 3 | H | [thiazole with CH₂—OH] | NMR |
| 4 | H | [oxazole with CH₃] | NMR |

TABLE I-continued (I)

Structure: R4-substituted pyrrolopyridinone with 2,4-dichlorophenyl at position 3, N-CH3, and N-R1.

| Compounds No. | R1 | R4 | Mp °C. NMR |
|---|---|---|---|
| 5 | H | 2-methyl-5-oxazolyl (5-methyl-oxazol-2-yl) | 338-340 |
| 6 | —CH3 | 2-methyl-4-methyl-thiazol-5-yl (2-methylthiazol-4-yl with methyl) | 253-254 |
| 7 | —CH3 | 2-(methylamino)-4-methylthiazol-5-yl | NMR |
| 8 | —CH3 | 4-methylthiazol-2-yl-CH2—O—COC(CH3)3 | 193-195 |
| 9 | —CH3 | 4-methylthiazol-2-yl-CH2—OH | 261-262 |
| 10 | —CH3 | 4-methylthiazol-2-yl-CH2—O—CH2CH3 | NMR |
| 11 | —CH3 | 4-methylthiazol-2-yl-CH2—O—CO-cyclopropyl | NMR |
| 12 | —CH3 | 4-methyloxazol-5-yl | 221-222 |
| 13 | —CH3 | 2-methyl-4-methyloxazol-5-yl | 222-223 |
| 14 | —CH3 | 2-amino-4-methyloxazol-5-yl | 295-297 |
| 15 | —CH3 | 4-methyloxazol-2-yl-CH2—OH | NMR |
| 16 | —CH3 | 4-methyloxazol-2-yl-CH2—O—CH2CH3 | NMR |
| 17 | —CH3 | 4-methyloxazol-2-yl-CH2—O—CO—C(CH3)3 | NMR |
| 18 | —CH3 | 2-methyl-5-methyloxazol-4-yl | 239-240 |

TABLE I-continued (I)
Structure: R4-substituted pyrrolo-pyridinone with 3-(2,4-dichlorophenyl), N-CH3, and N-R1

| Compounds No. | R1 | R4 | Mp °C. NMR |
|---|---|---|---|
| 19 | —CH3 | 2-(ethoxymethyl)-5-methyl-oxazol-yl (CH2—O—CH2CH3 on 5-methyl oxazole) | 179-180 |
| 20 | —CH3 | 3-amino-5-methyl-pyrazol-yl (H2N-pyrazole-NH, methyl) | 284-286 |
| 21 | —CH3 | 2-amino-4-methyl-thiazol-yl (NH2 on thiazole, methyl) | 272-273 |
| 22 | H | 2-methyl-thiazol-yl | NMR |
| 23 | —CH3 | 2-methyl-thiazol-yl | NMR |
| 24 | —CH3 | 2,4-dimethyl-oxazol-yl (H3C on oxazole, methyl) | 258-261 |
| 25 | —CH3 | 2,4-dimethyl-thiazol-yl (CH3 on thiazole, methyl) | 255-257 |
| 26 | —CH3 | 4-amino-2-methyl-thiazol-yl (NH2 on thiazole, methyl) | NMR |

TABLE I-continued (I)
Structure: R4-substituted pyrrolo-pyridinone with 3-(2,4-dichlorophenyl), N-CH3, and N-R1

| Compounds No. | R1 | R4 | Mp °C. NMR |
|---|---|---|---|
| 27 | —CH3 | 4-(chloromethyl)-2-methyl-thiazol-yl (CH2—Cl on thiazole, methyl) | 277-281 |
| 28 | —CH3 | 4-(aminomethyl)-2-methyl-thiazol-yl (CH2—NH2 on thiazole, methyl) | 261-266 |
| 29 | —CH3 | 4-(pyrrolidin-1-ylmethyl)-2-methyl-thiazol-yl (CH2—N(pyrrolidine) on thiazole, methyl) | 222-226 |
| 30 | —CH3 | 4-((dimethylamino)methyl)-2-methyl-thiazol-yl (CH2—N(CH3)2 on thiazole, methyl) | NMR |
| 31 | —CH3 | 4-((methoxycarbonyl)methyl)-2-methyl-thiazol-yl (CH2—COOCH3 on thiazole, methyl) | 198-201 |
| 32 | —CH3 | 4-(carboxymethyl)-2-methyl-thiazol-yl (CH2—COOH on thiazole, methyl) | 234-239 |
| 33 | —CH3 | 5-methyl-oxazol-yl | 170-174 |

TABLE I-continued
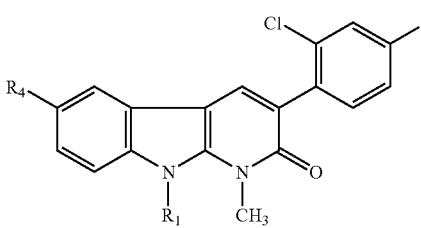
(I)
| Compounds No. | R₁ | R₄ | Mp °C. NMR |
|---|---|---|---|
| 34 | —CH₃ | 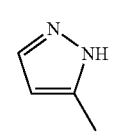 | 240-245 |
| 35 | H | 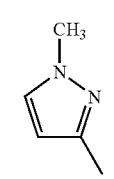 | 320-323 |
| 36 | H | 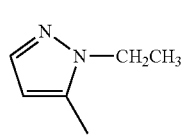 | 246-250 |
| 37 | H | 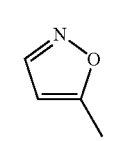 | 129-135 |
| 38 | H | 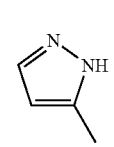 | 255-258 |
| 39 | —CH₃ | 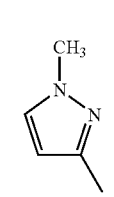 | 241-242 |
| 40 | —CH₃ | 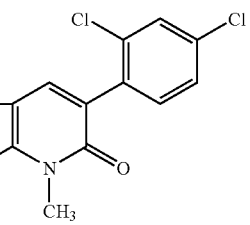 | 281-282 |
| 41 | —CH₃ |  | 287-290 |
TABLE I-continued
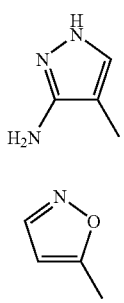
(I)
| Compounds No. | R₁ | R₄ | Mp °C. NMR |
|---|---|---|---|
| 42 | —CH₃ | 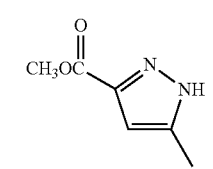 | 230-232 |
| 43 | —CH₃ | 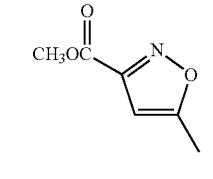 | 232-233 |
| 44 | —CH₃ | 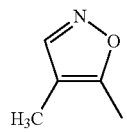 | 290-292 |
| 45 | —CH₃ | 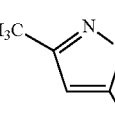 | 280-281 |
| 46 | —CH₃ |  | 233-234 |
| 47 | —CH₃ |  | 309-310 |

TABLE I-continued

[Structure (I): R4-substituted indole fused pyridinone with 2,4-dichlorophenyl at position 3, N-CH3 and N-R1]

| Compounds No. | R₁ | R₄ | Mp °C. NMR |
|---|---|---|---|
| 48 | —CH₃ | 4-methyl-1H-1,2,3-triazol-5-yl | 274-275 |
| 49 | —CH₃ | 5-methyl-2-amino-1,3,4-thiadiazol-yl (H₂N-, S, methyl) | 321-323 |
| 50 | —CH₃ | 5-methyl-oxazol-2-yl (H₃C-oxazole) | 289-292 |

The table which follows illustrates the chemical structures and the physical properties of some examples of compounds according to the invention.

TABLE II

[Structure: R4-substituted indole fused pyridinone with R3 at position 3, N-CH3 and N-R1]

| | R1 | R4 | R3 | |
|---|---|---|---|---|
| 51 | —CH₃ | 1-(2-hydroxyethyl)-3-methyl-pyrazol-5-yl, (CH2)2—OH | 2,4-dichlorophenyl | NMR |
| 52 | —CH₃ | 1-ethyl-4,5-dimethyl-pyrazol-3-yl (N-CH2-CH3, CH3, CH3) | 2,4-dichlorophenyl | NMR |
| 53 | CH₃ | 4-methyl-1H-pyrazol-3-yl (NH, CH3) | 2,4-dichlorophenyl | NMR |
| 54 | CH₃ | 3-methyl-5-methyl-isoxazol-4-yl (CH3, CH3) | 2,4-dichlorophenyl | NMR |
| 55 | CH₃ | 5-amino-3-methyl-isoxazol-4-yl (NH2, CH3) | 2,4-dichlorophenyl | NMR |

TABLE II-continued
| | R1 | R4 | R3 | |
|---|---|---|---|---|
| 56 | CH₃ | 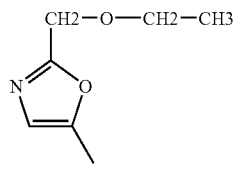 | 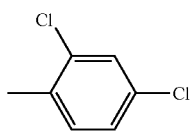 | NMR |
| 57 | CH₃ | 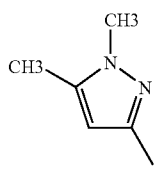 | 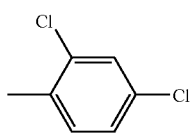 | NMR |
| 58 | CH₃ | 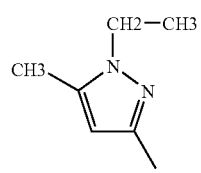 | 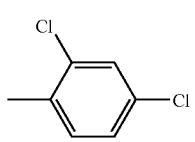 | NMR |
| 59 | CH₃ | 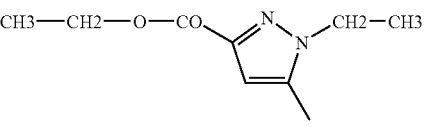 | 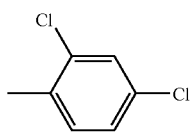 | NMR |
| 60 | CH₃ | 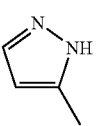 | 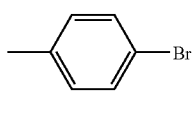 | NMR |
| 61 | CH₃ | 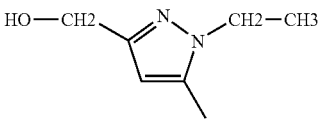 | 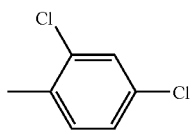 | NMR |
| 62 | CH₃ | 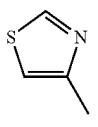 | 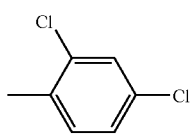 | NMR |
| 63 | CH₃ | 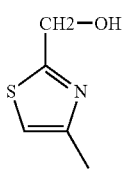 | 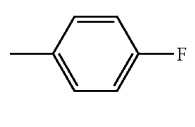 | NMR |
| 64 | CH₃ | 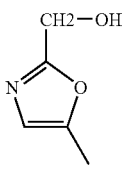 | 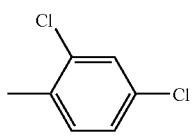 | NMR |
| 65 | CH₃ | 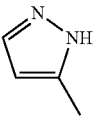 | 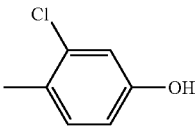 | NMR |

TABLE II-continued
| | R1 | R4 | R3 | |
|---|---|---|---|---|
| 66 | CH₃ | 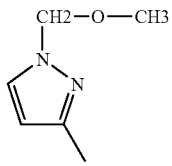 | 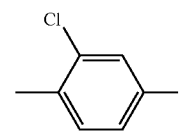 | NMR |
| 67 | CH₃ | 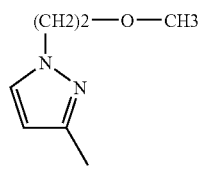 | 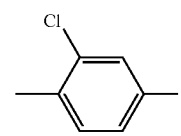 | NMR |
| 68 | CH₃ | 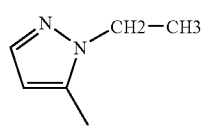 | 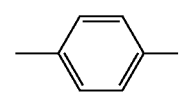 | NMR |
| 69 | CH₃ | 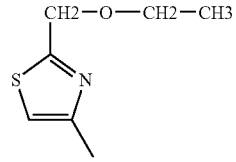 | 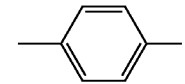 | NMR |
| 70 | CH₃ | 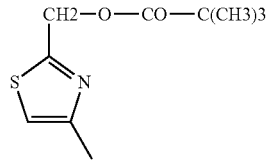 | 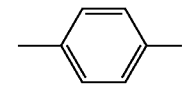 | NMR |
| 71 | CH₃ | 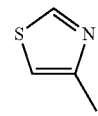 | 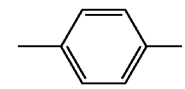 | NMR |
| 72 | CH₃ | 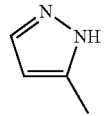 | 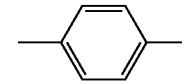 | NMR |
| 73 | CH₃ | 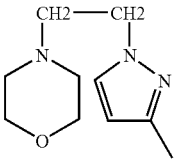 | 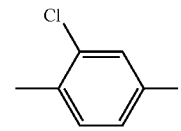 | NMR |
| 74 | CH₃ | 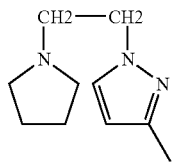 | 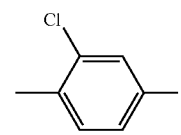 | NMR |
| 75 | CH₃ | 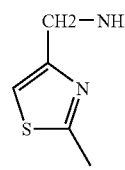 | 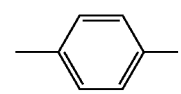 | NMR |

TABLE II-continued
| | R1 | R4 | R3 | |
|---|---|---|---|---|
| 76 | CH₃ | 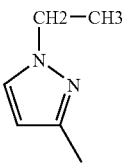 | 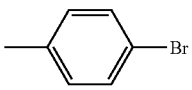 | NMR |
| 77 | CH₃ | 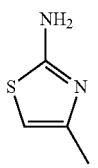 | 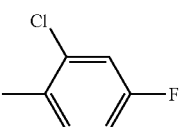 | NMR |
| 78 | CH₃ | 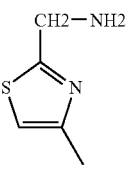 | 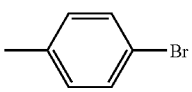 | NMR |
| 79 | CH₃ | 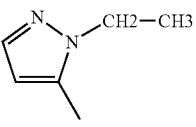 | 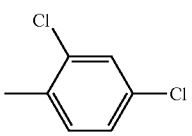 | NMR |
| 80 | CH₃ | 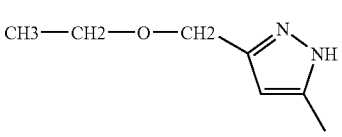 | 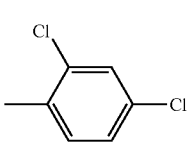 | NMR |
| 81 | CH₃ | 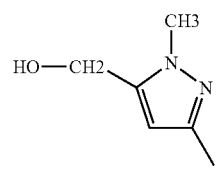 | 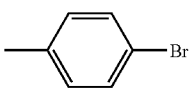 | NMR |
| 82 | CH₃ | 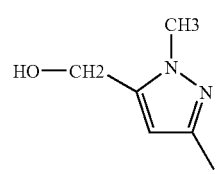 | 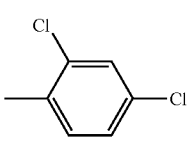 | NMR |
| 83 | CH₃ | 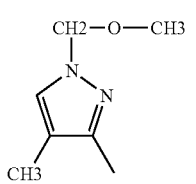 | 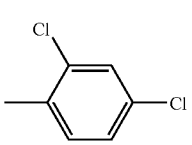 | NMR |
| 84 | CH₃ | 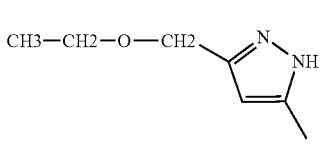 | 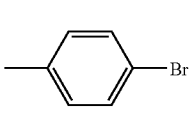 | NMR |

TABLE II-continued

| | R1 | R4 | R3 | |
|---|---|---|---|---|
| 85 | CH₃ | 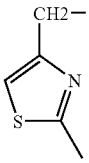 CH2—NH—CO—C(CH3)3 (2-methyl-thiazol-4-yl) |  4-Br-phenyl | NMR |
| 86 | CH₃ | 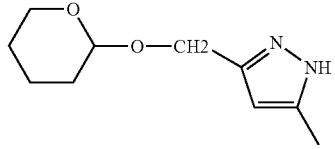 tetrahydropyran-2-yloxy-CH2-(5-methyl-1H-pyrazol-3-yl) |  4-Br-phenyl | NMR |
| 87 | CH₃ | 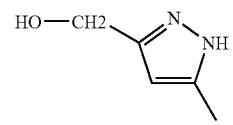 HO—CH2-(5-methyl-1H-pyrazol-3-yl) |  4-Br-phenyl | NMR |
| 88 | CH₃ | 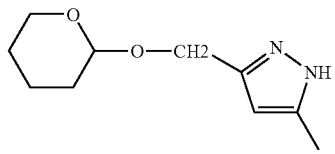 tetrahydropyran-2-yloxy-CH2-(5-methyl-1H-pyrazol-3-yl) | 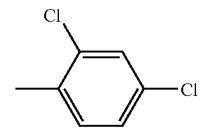 2,4-diCl-phenyl | NMR |
| 89 | CH₃ | 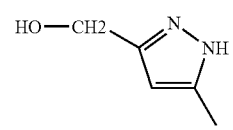 HO—CH2-(5-methyl-1H-pyrazol-3-yl) | 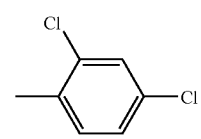 2,4-diCl-phenyl | NMR |
| 90 | CN | 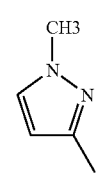 1-methyl-3-methyl-pyrazole | 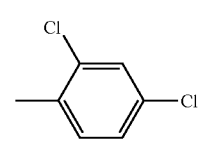 2,4-diCl-phenyl | NMR |
| 91 | CH₃ | 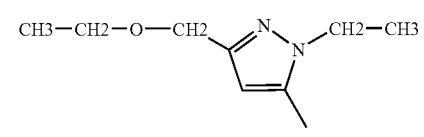 CH3—CH2—O—CH2-(1-ethyl-5-methyl-pyrazol-3-yl) | 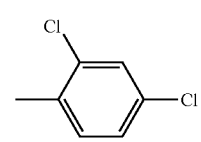 2,4-diCl-phenyl | NMR |
| 92 | CH₃ | 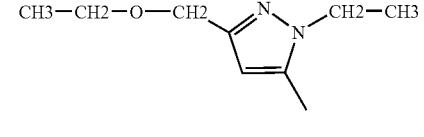 CH3—CH2—O—CH2-(1-ethyl-5-methyl-pyrazol-3-yl) | 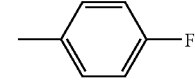 4-F-phenyl | NMR |
| 93 | CH₃ | 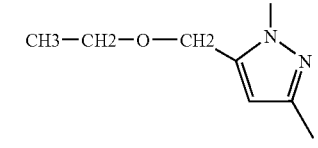 CH3—CH2—O—CH2-(1-methyl-3-methyl-pyrazol-5-yl) | 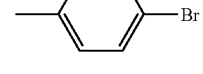 4-Br-phenyl | NMR |
| 94 | CH₃ | 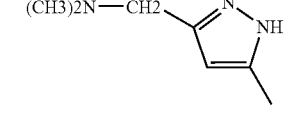 (CH3)2N—CH2-(5-methyl-1H-pyrazol-3-yl) | 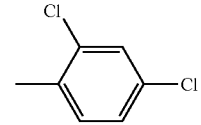 2,4-diCl-phenyl | NMR |

TABLE II-continued

| | R1 | R4 | R3 | |
|---|---|---|---|---|
| 95 | CH₃ | CH2—OH, thiazole (2-methyl, 4-position) | 2,4-dichlorophenyl | NMR |
| 96 | CH₃ | (CH3)3—C—CO—O—CH2-thiazole (4-methyl, 2-position) | 2,4-dichlorophenyl | NMR |
| 97 | CN | (CH3)3—C—CO—O—CH2-thiazole (4-methyl, 2-position) | 2,4-dichlorophenyl | NMR |
| 98 | CH₃ | CH3—O—CH2-thiazole (4-methyl, 2-position) | 2,4-dichlorophenyl | NMR |
| 99 | CH₃ | CO—C—(CH3)3 on pyrazole N (3,4-dimethyl) | 2,4-dichlorophenyl | NMR |
| 100 | CH₃ | HO—CH2-thiazole (2-methyl, 4-position) | 4-fluorophenyl | NMR |
| 101 | CH₃ | CH3—O—CH2-thiazole (2-methyl, 4-position) | 4-fluorophenyl | NMR |
| 102 | CH₃ | CH3—O—CH2-thiazole (2-methyl, 4-position) | 2,4-dichlorophenyl | NMR |
| 103 | CH₃ | CH3—CH2—O—CH2-thiazole (2-methyl, 4-position) | 2,4-dichlorophenyl | NMR |

TABLE II-continued
| | R1 | R4 | R3 | |
|---|---|---|---|---|
| 104 | CH₃ | 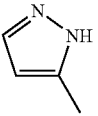 | 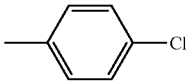 | NMR |
| 105 | CH₃ | 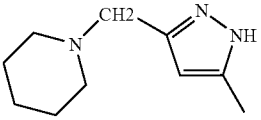 | 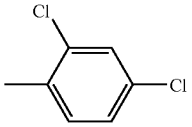 | NMR |
| 106 | CH₃ | 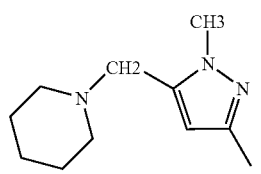 | 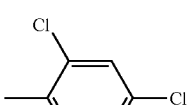 | NMR |
| 107 | CH₃ | 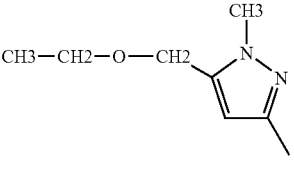 | 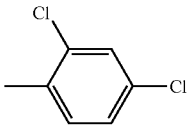 | NMR |
| 108 | CH₃ | 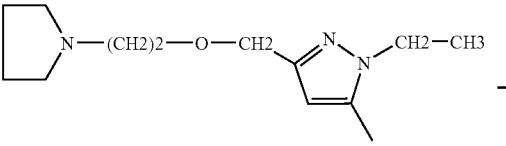 | 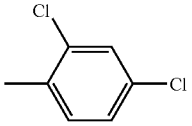 | NMR |
| 109 | H | 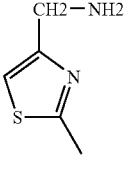 | 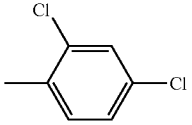 | NMR |
| 110 | CH₃ | 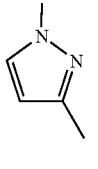 |  | NMR |
| 111 | CH₃ | 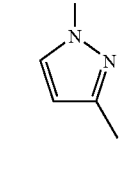 | 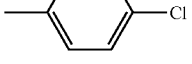 | NMR |
| 112 | CH₃ |  | 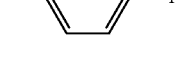 | NMR |

TABLE II-continued
| | R1 | R4 | R3 | |
|---|---|---|---|---|
| 113 | CH₃ | 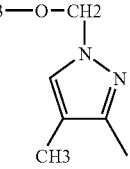 | 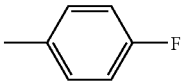 | NMR |
| 114 | CH₃ | 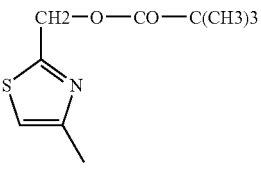 | 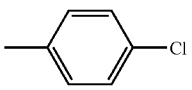 | NMR |
| 115 | CH₃ | 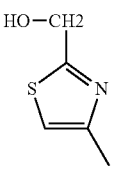 | 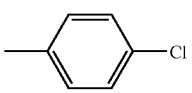 | NMR |
| 116 | CH₃ | 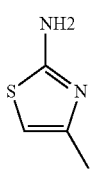 | 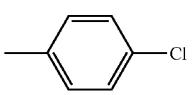 | NMR |
| 117 | CH₃ | 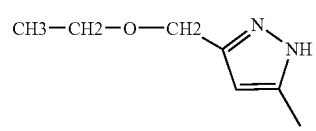 | 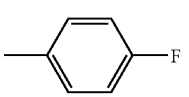 | NMR |
| 118 | CH₃ | 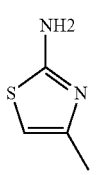 | 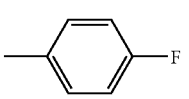 | NMR |
| 119 | CH₃ | 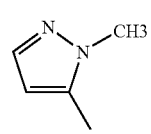 | 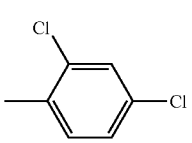 | NMR |
| 120 | CH₃ | 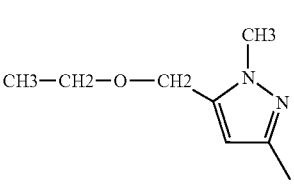 | 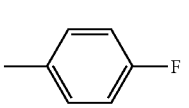 | NMR |
| 121 | CH₃ | 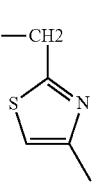 | 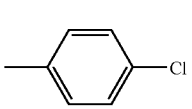 | NMR |

TABLE II-continued

| | R1 | R4 | R3 | |
|---|---|---|---|---|
| 122 | CH₃ | morpholine-N-CH2-(1-CH3, 3-methyl-pyrazol-5-yl) | 2,4-dichlorophenyl | NMR |
| 123 | CH₃ | CH3-N(piperazine)N-CH2-(1-CH3, 3-methyl-pyrazol-5-yl) | 2,4-dichlorophenyl | NMR |
| 124 | CH₃ | morpholine-N-CH2-CH2-N-CH2-(1-CH3, 3-methyl-pyrazol-5-yl) | 2,4-dichlorophenyl | NMR |
| 125 | CH₃ | cyclopropyl-CH2-O-(CH2)2-(3-methyl-pyrazol-1-yl) | 2,4-dichlorophenyl | NMR |
| 126 | CH₃ | CH3-CH2-O-(CH2)2-O-(CH2)2-(3-methyl-pyrazol-1-yl) | 2,4-dichlorophenyl | NMR |
| 127 | CH₃ | CH3-CH2-O-(CH2)2-O-CH2-(1-CH3, 3-methyl-pyrazol-5-yl) | 2,4-dichlorophenyl | NMR |
| 128 | CH₃ | morpholine-N-(CH2)2-NH-CH2-(4-methyl-thiazol-2-yl) | 2,4-dichlorophenyl | NMR |
| 129 | CH₃ | CH3-O-(CH2)2-O-CH2-(3-methyl-pyrazol-1-yl) | 2,4-dichlorophenyl | NMR |

TABLE II-continued

| | R1 | R4 | R3 | |
|---|---|---|---|---|
| 130 | CH₃ | 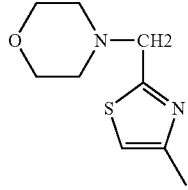 morpholine-N-CH2-(4-methylthiazol-2-yl) | 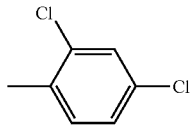 2,4-dichlorophenyl | NMR |
| 131 | CH₃ | 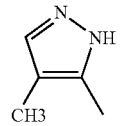 4,5-dimethyl-1H-pyrazol-3-yl |  4-chlorophenyl | NMR |
| 132 | CH₃ | 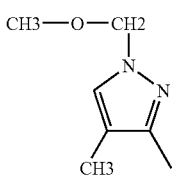 CH3-O-CH2-N(pyrazole with CH3) |  4-chlorophenyl | NMR |
| 133 | CH₃ | 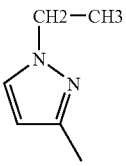 CH2-CH3 N-pyrazole-CH3 |  4-fluorophenyl | NMR |
| 134 | CH₃ | 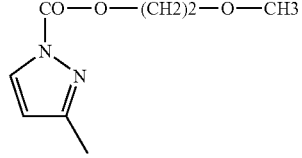 CO-O-(CH2)2-O-CH3 pyrazole | 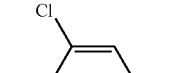 2,4-dichlorophenyl | NMR |
| 135 | CH₃ | 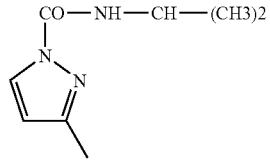 CO-NH-CH-(CH3)2 pyrazole | 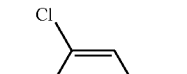 2,4-dichlorophenyl | NMR |
| 136 | CH₃ | 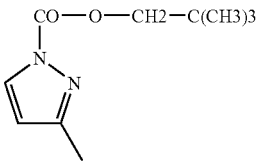 CO-O-CH2-C(CH3)3 pyrazole | 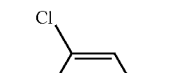 2,4-dichlorophenyl | NMR |
| 137 | CH₃ | 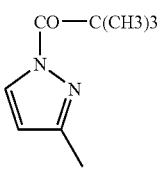 CO-C(CH3)3 pyrazole | 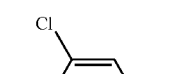 2,4-dichlorophenyl | NMR |
| 138 | CH₃ | 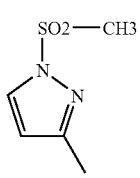 SO2-CH3 pyrazole | 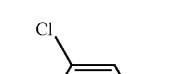 2,4-dichlorophenyl | NMR |

TABLE II-continued

| | R1 | R4 | R3 | |
|---|---|---|---|---|
| 139 | CH₃ | 2-(2-hydroxypropan-2-yl)-4-methylthiazole [C(CH3)2—OH on thiazole] | 2,4-dichlorophenyl | NMR |
| 140 | CH₃ | 1-cyclohexyl-5-methyl-1H-pyrazole | 2,4-dichlorophenyl | NMR |
| 141 | CH₃ | 5-methyl-1H-pyrazole | 2-fluoro-4-chlorophenyl | NMR |
| 142 | CH₃ | 1-ethyl-3-methyl-1H-pyrazole [CH2—CH3] | 2-fluoro-4-chlorophenyl | NMR |
| 143 | CH₃ | 1-(2-methoxyethyl)-5-methyl-1H-pyrazole [(CH2)2—O—CH3] | 2,4-dichlorophenyl | NMR |
| 144 | CH₃ | 1-(ethoxymethyl)-3-methyl-1H-pyrazole [CH2—O—CH2—CH3] | 2,4-dichlorophenyl | NMR |
| 145 | CH₃ | 1-acetyl-3-methyl-1H-pyrazole [CO—CH3] | 2,4-dichlorophenyl | NMR |
| 146 | CH₃ | 2-(aminomethyl)-4-methylthiazole [CH2—NH2] | 2,4-dichlorophenyl | NMR |
| 147 | CH₃ | N-((4-methylthiazol-2-yl)methyl)methanesulfonamide [CH2—NH—SO2—CH3] | 2,4-dichlorophenyl | NMR |

TABLE II-continued
| | R1 | R4 | R3 | |
|---|---|---|---|---|
| 148 | CH₃ | 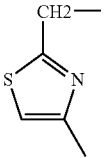 | 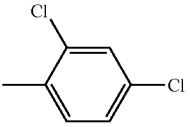 | NMR |
| 149 | CH₃ | 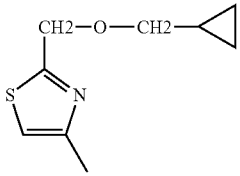 | 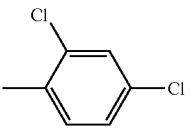 | NMR |
| 150 | CH₃ | 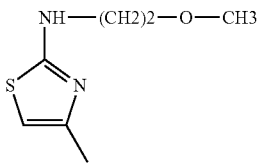 | 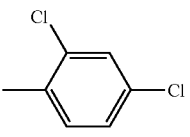 | NMR |
| 151 | CHF2 | 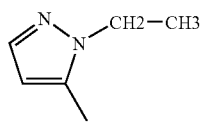 | 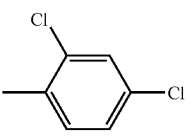 | NMR |
| 152 | CH₃ | 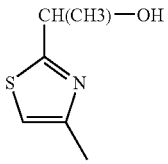 | 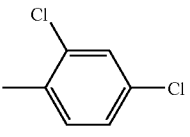 | NMR |
| 153 | CH₃ | 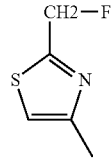 | 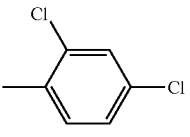 | NMR |
| 154 | CH₃ | 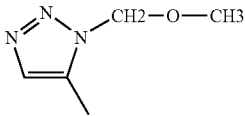 | 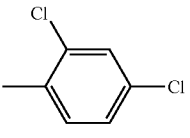 | NMR |
| 155 | CH₃ | 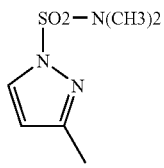 | 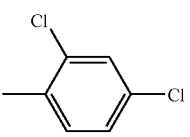 | NMR |
| 156 | CH₃ | 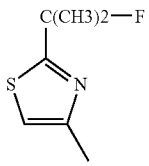 | 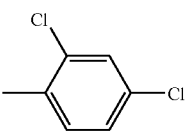 | NMR |

TABLE II-continued

| | R1 | R4 | R3 | |
|---|---|---|---|---|
| 157 | CH₃ | 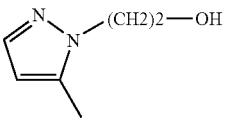 (CH2)2—OH on pyrazole N, methyl on pyrazole | 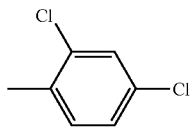 2,4-Cl₂-phenyl | NMR |
| 158 | CH₃ | 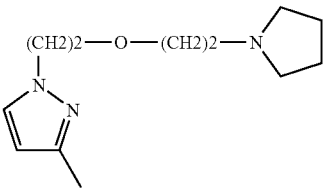 (CH2)2—O—(CH2)2—N(pyrrolidine) on pyrazole, methyl on pyrazole | 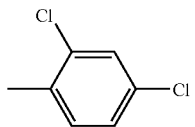 2,4-Cl₂-phenyl | NMR |
| 159 | CH₃ | 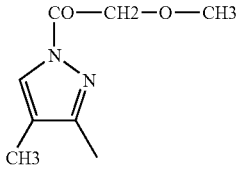 CO—CH2—O—CH3 on pyrazole N, CH3 substituent | 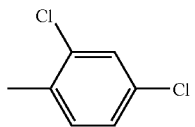 2,4-Cl₂-phenyl | NMR |
| 160 | CH₃ | 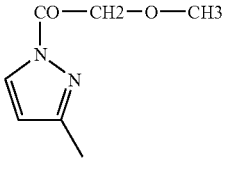 CO—CH2—O—CH3 on pyrazole N | 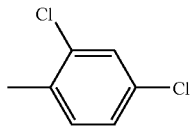 2,4-Cl₂-phenyl | NMR |
| 161 | CHF₂ | 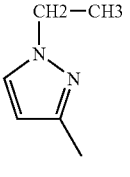 CH2—CH3 on pyrazole N | 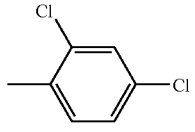 2,4-Cl₂-phenyl | NMR |
| 162 | CH₃ | 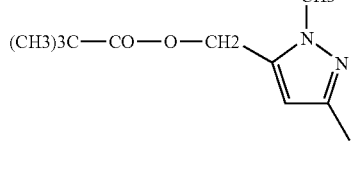 (CH3)3C—CO—O—CH2-pyrazole with CH3 groups | 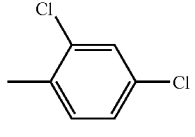 2,4-Cl₂-phenyl | NMR |
| 163 | CH₃ | 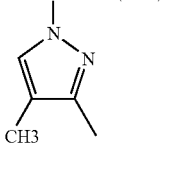 CO—C(CH3)3 on pyrazole N, CH3 substituent | 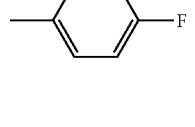 4-F-phenyl | NMR |
| 164 | CH₃ | 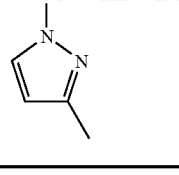 CO—CH2—CF3 on pyrazole N | 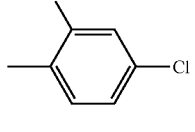 2,4-Cl₂-phenyl | NMR |

The compounds of formula (I) according to the present invention were tested in vitro and on a human breast cancer cell line: the MDA-MB-231 line available from the American Type Culture Collection (reference HTB26).

The evaluation of the antiproliferative effect is carried out according to J. M. Derocq et al., FEBS Letters, 1998, 425, 419-425: the rate of incorporation of [3H]thymidine into the DNA of the treated cells, after incubation for 96 hours with a compound of formula (I), is measured. The inhibitory concentration 50 (IC50) is defined as the concentration which inhibits the cell proliferation by 50%.

The compounds according to the invention have an IC50 which is generally less than 10 µM on the MDA-MB-231 line.

The compounds of formula (I) were also tested on another human breast cancer line, referred to as an MDR (multi-drug-resistant) line, and called MDA-A1. This line is described by E. Coliomb, C. Dussert and P. M. Martin in Cytometry, 1991, 12(1), 15-25.

The term "multi-drug-resistant" which describes this line means that said line is not very sensitive, in general, to the chemotherapy drugs commonly used, and in particular to the antimitotics of natural origin such as paclitaxel, vincristine, vinblastine.

The compounds according to the invention have an IC50 which is generally less than 10 µM on the multi-drug-resistant line MDA-A1.

Thus, according to the present invention, it appears that the compounds of formula (I) inhibit the proliferation of tumor cells, including that of cells exhibiting a multi-drug resistance. It therefore appears that the compounds according to the invention have an anticancer activity.

Thus, according to another of its aspects, a subject of the invention is medicaments which comprise a compound of formula (I), or an addition salt of the latter with a pharmaceutically acceptable acid or else a hydrate or a solvate of the compound of formula (I).

These medicaments can be used in therapeutics, in particular in the treatment or prevention of diseases caused or exacerbated by tumor cell proliferation. As an inhibitor of tumor cell proliferation, these compounds can be used in the treatment of all types of neoplasmas, of all origins, whether they are solid or non-solid, benign or malignant, primary or metastatic, carcinomas, sarcomas, adenomas, adenocarcinomas, in particular: breast cancer; lung cancer; cancer of the small intestine, cancer of the colon and rectum; cancer of the respiratory pathways, of the oropharynx and of the hypopharynx; esophageal cancer; liver cancer, stomach cancer, cancer of the bowel ducts, gallbladder cancer, pancreatic cancer; cancer of the urinary tracts, including kidney, urothelium and bladder; cancers of the female genital tract, including uterine cancer, cervical cancer, ovarian cancer, choriocarcinoma and trophoblastoma; cancers of the male genital tract, including prostate cancer, cancer of the seminal vesicles, testicular cancer, germinal cell tumors; cancers of the endocrine glands, including cancer of the thyroid, of the pituitary gland, of the adrenal glands; skin cancers, including haemangiomas, melanomas, sarcomas, including Kaposi's sarcoma; brain tumors, tumors of the nerves, of the eyes, of the meninges, including astrocytomas, gliomas, glioblastomas, retinoblastomas, neurinomas, neuroblastomas, schwannomas, meningiomas; tumors originating from malignant haematopoietic tumors, including leukaemias, chloromas, plasmacytomas, mycosis fongoides, T-cell leukaemia or lymphoma, non-Hodgkin's lymphoma, malignant haemopathies, myelomas.

According to another of its aspects, the present invention relates to pharmaceutical compositions comprising, as active ingredient, a compound according to the invention. These pharmaceutical compositions contain an effective does of at least one compound according to the invention, or a pharmaceutically acceptable salt, a hydrate or solvate of said compound, and also at least one pharmaceutically acceptable excipient.

Said excipients are selected according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its possible salt, solvate or hydrate, can be administered in unit administration form, as a mixture with conventional pharmaceutical excipients, to animals or to humans for the prophylaxis or treatment of the conditions or diseases above.

The appropriate unit administration forms include forms for oral administration, such as tablets, soft or hard gelatine capsules, powders, granules, and oral solutions or suspensions, forms for sublingual, buccal, intratracheal, intraocular, intranasal administration, forms for administration by inhalation, forms for topical, transdermal, subcutaneous, intramuscular or intravenous administration, forms for rectal administration, and implants. For topical application, the compounds according to the invention can be used in creams, gels, ointments or lotions.

The compounds of formula (I) above can be used at daily doses of 0.002 to 2000 mg per kilogram of body weight of the mammal to be treated, preferably at daily doses of 0.1 to 300 mg/kg. In human beings, the dose can range preferably from 0.02 to 10 000 mg per day, more particularly from 1 to 3000 mg, according to the age of the individual to be treated or the type of treatment: prophylactic or curative.

There may be specific cases where higher or lower doses are appropriate: such dosages do not depart from the scope of the invention. According to the usual practice, the dosage appropriate for each patient is determined by the physician according to the method of administration and the weight and response of said patient.

According to another of its aspects, the present invention also relates to a method of treating the pathologies indicated above, which comprises the administration, to a patient, of an effective dose of a compound according to the invention, or one of its pharmaceutically acceptable salts or hydrates or solvates.

According to the present invention, the compound(s) of formula (I) can be administered in combination with one (or more) anticancer active ingredient(s), chosen from those described in the literature or known to those skilled in the art: mention may be made in particular of antitumor compounds such as alkylating agents, for instance alkyl sulphonates (busulfane), dacarbazine, procarbazine, nitrogenous mustards (chloromethane, melphalan, chlorambucil), cyclophosphamide, ifosfamide; nitrosoureas such as carmustine, lomustine, semustine, streptozocin; antineoplastic alkaloids such as vincristine, vinblastine; taxanes such as paclitaxel or taxotere; antineoplastic antibiotics such as actinomycin; intercalating agents, antineoplastic antimetabolites, foliate antagonists, methotrexate; purine synthesis inhibitors; purine analogues such as mercaptopurine, 6-thioguanine; pyrimidine synthesis inhibitors, aromatase inhibitors, capecitabine, pyrimidine analogues such as fluorouracil, gemcitabine, cytarabine and cytosine arabinoside; brequinar; topoisomerase inhibitors such as camptothecin or etoposide; anticancer hormone agonists and antagonists including tamoxifen; kinase inhibitors, imatinib, sutinib, sorafenib; growth factor inhibi-

What is claimed is:

1. A compound of formula (I):

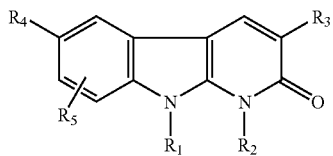

in which:
R₁ is a hydrogen atom or a (C₁-C₄)alkyl, CN, CF₃ or CHF₂ group;
R₂ is a hydrogen atom or a (C₁-C₄)alkyl group;
R₃ is a phenyl which is unsubstituted or substituted one or more times with substituents selected independently from a halogen atom, a (C₁-C₄)alkyl group and a (C₁-C₄)alkoxy group;
R₄ is a heterocyclic radical selected from:

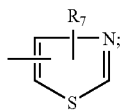 (A)

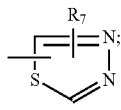 (B)

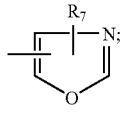 (C)

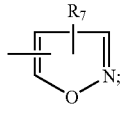 (D)

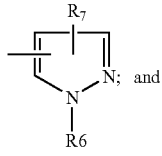 (E) and

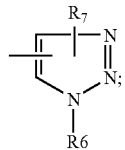 (F)

R₅ is a hydrogen atom, a halogen atom, a (C₁-C₄)alkyl group or a (C₁-C₄) alkoxy group;
R6 is selected from the group consisting of:
a hydrogen atom,
a —SO₂—R₁₂ group,
a (C₁-C₆)alkyl group,
a (C₁-C₆) mono or perfluoro alkyl group,
a —(CH₂)ₙ—NR8R9,
a —(CH₂)ₙ—NH—CO—(C₁-C₄)alkyl group,
a —(CH₂)ₙ—NH—SO₂—(C₁-C₄)alkyl group,
a —(CH₂)ₙ—NH—(CH₂)ₘ—NR8R9 group,
a —(CH₂)ₙ—NH—(CH₂)ₘ—OR10 group,
a —(CH₂)ₙ—O—(CH₂)ₘ—NR8R9 group,
a —(CH₂)ₙ—O—(CH₂)ₘ—O—(C₁-C₄)alkyl group,
a —(CH₂)ₙHal group,
a —(C₁-C₆)alkyl-O—R10 group,
a —CO₂—(CH₂)ₘ—O—R10 group,
a —(CH₂)ₙ—COOR11 group,
a (C₁-C₆)alkylcarbonyl-group,
a (C₁-C₆) mono or perfluoro alkylcarbonyl-group,
a —CO—NH—R10 group, and
a —CO—(C₁-C₆)alkyl-O—(C₁-C₄)alkyl group;
R7 is selected from the group consisting of:
a hydrogen atom,
a (C₁-C₆)alkyl group,
a (C₁-C₆) mono or perfluoro alkyl group,
a —(CH₂)ₙ—NR8R9 group,
a —(CH₂)ₙ—NH—CO—(C₁-C₄)alkyl group,
a —(CH₂)ₙ—NH—SO₂—(C₁-C₄)alkyl group,
a —(CH₂)ₙ—NH—(CH₂)ₘ—NR8R9 group,
a —(CH₂)ₙ—NH—(CH₂)ₘ—OR10 group,
a —(CH₂)ₙ—O—(CH₂)ₘ—NR8R9 group,
a —(CH₂)ₙ—O—(CH₂)ₘ—O—(C₁-C₄) alkyl group,
a —(CH₂)ₙHal group,
a —(C₁-C₆)alkyl-O—R10 group,
a —CO₂—(CH₂)ₘ—O—R10 group,
a —(CH₂)ₙ—COOR11 group,
a (C₁-C₆)alkylcarbonyl-group,
a (C₁-C₆) mono or perfluoro alkylcarbonyl-group,
a —CO—NH—R10 group, and
a —CO—(C₁-C₆)alkyl-O—(C₁-C₄)alkyl group;
R8 and R9 are each, independently of one another, a hydrogen atom or a (C₁-C₄)alkyl group;
or else R₈ and R₉, together with the nitrogen atom to which they are attached, constitute a heterocyclic radical selected from pyrrolidin-1-yl, piperidin-1-yl, morpholin-4-yl and piperazinyl optionally substituted on its second nitrogen atom;
R₁₀ is a hydrogen atom, a (C₁-C₄)alkyl group, a (C₁-C₄)alkylcarbonyl-group, a (C₃-C₆)cycloalkylcarbonyl-group, a (C₃-C₆)cycloalkyl(C₁-C₄)alkylcarbonyl-group, a (C₃-C₆)cycloalkyl group, a (C₅-C₆)heterocycloalkyl group, a (C₁-C₆) mono or perfluoro alkyl group, or a (C₃-C₆)cycloalkyl(C₁-C₄)alkyl group;
R₁₁ is a hydrogen atom or a (C₁-C₆)alkyl group;

$R_{12}$ is a $(C_1-C_6)$alkyl group, a $(C_1-C_6)$ mono or perfluoro alkyl group, a cycloalkyl group, a cycloalkylalkyl-group, or a $(C_1-C_6)$alkyl-O—$(C_1-C_4)$alkyl-group;

m is 1 or 2;

n is 0, 1 or 2;

Hal is a halogen atom;

or an acid addition salt thereof.

2. A compound of formula (I) according to claim 1, in which:

$R_1$ is a hydrogen atom or a $(C_1-C_4)$ alkyl group;

$R_2$ is a hydrogen atom or a $(C_1-C_4)$ alkyl group;

$R_3$ is a phenyl which is unsubstituted or substituted one or more times with substituents selected independently from a halogen atom, a $(C_1-C_4)$ alkyl group and a $(C_1-C_4)$ alkoxy group;

$R_4$ is a heterocyclic radical selected from:

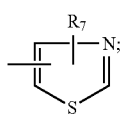
(A)

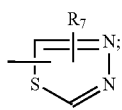
(B)

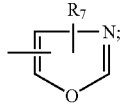
(C)

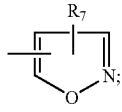
(D)

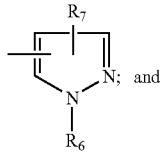
(E)

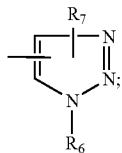
(F)

$R_5$ is a hydrogen atom, a halogen atom, a $(C_1-C_4)$ alkyl group or a $(C_1-C_4)$ alkoxy group;

$R_6$ is a hydrogen atom or a $(C_1-C_4)$ alkyl group;

$R_7$ is a hydrogen atom, a $(C_1-C_4)$ alkyl group, a —$(CH_2)_n$—$NR_8R_9$ group, a —$(CH_2)_n$Hal group, a —$CH_2$—O—$R_{10}$ group or a —$(CH_2)_n$—$COOR_{11}$ group;

$R_8$ and $R_9$ are each, independently of one another, a hydrogen atom or a $(C_1-C_4)$ alkyl group;

or else $R_8$ and $R_9$, together with the nitrogen atom to which they are attached, constitute a heterocyclic radical selected from pyrrolidin-1-yl, piperidin-1-yl and morpholin-4-yl;

$R_{10}$ is a hydrogen atom, a $(C_1-C_4)$ alkyl group, a $(C_1-C_4)$ alkylcarbonyl group or a $(C_3-C_6)$ cycloalkylcarbonyl group;

$R_{11}$ is a hydrogen atom or a $(C_1-C_4)$ alkyl group;

n is 0 or 1;

Hal is a halogen atom;

or an acid addition salt thereof.

3. A compound of formula (I) according to claim 1, wherein $R_4$ is:

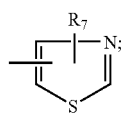
(A)

and the substituents $R_1$ to $R_7$ are as defined for the compounds of formula (I) in claim 1;

or an acid addition salt thereof.

4. A compound of formula (I) according to claim 1, wherein $R_4$ is:

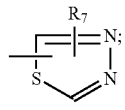
(B)

and the substituents $R_1$ to $R_7$ are as defined for the compounds of formula (I) in claim 1;

or an acid addition salt thereof.

5. A compound of formula (I) according to claim 1, wherein $R_4$ is:

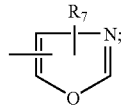
(C)

and the substituents $R_1$ to $R_7$ are as defined for the compounds of formula (I) in claim 1;

or an acid addition salt thereof.

6. A compound of formula (I) according to claim 1, wherein $R_4$ is:

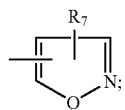
(D)

and the substituents $R_1$ to $R_7$ are as defined for the compounds of formula (I) in claim 1;

or an acid addition salt thereof.

7. A compound of formula (I) according to claim 1, wherein

R$_4$ is:

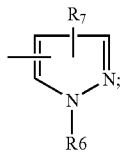

(E)

and the substituents R$_1$ to R$_7$ are as defined for the compounds of formula (I) in claim 1;

or an acid addition salt thereof.

8. A compound of formula (I) according to claim 1, wherein

R$_4$ is:

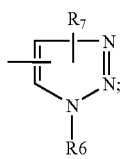

(F)

and the substituents R$_1$ to R$_7$ are as defined for the compounds of formula (I) in claim 1;

or an acid addition salt thereof.

9. A compound of formula (I) according to claim 1 in which:

R$_1$ is a hydrogen atom or a methyl;

R$_2$ is a methyl;

R$_3$ is a 2,4-dichlorophenyl;

R$_4$ is a heterocyclic radical selected from:

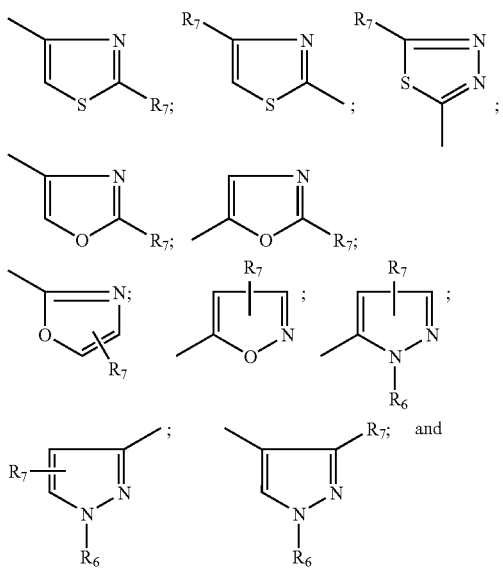

-continued

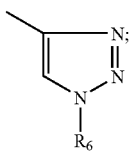

R$_5$ is a hydrogen atom;

R$_6$ is a hydrogen atom, a methyl or an ethyl;

R$_7$ is a hydrogen atom, a methyl, an amino, a methylamino, an aminomethyl, a (dimethylamino)methyl, a pyrrolidin-1-ylmethyl, a chloromethyl, a hydroxymethyl, an ethoxymethyl, a [(2,2-dimethylpropanoyl)oxy]methyl, a [(cyclopropylcarbonyl)oxy]methyl, a methoxycarbonyl, a 2-methoxy-2-oxoethyl or a carboxymethyl;

or an acid addition salt thereof.

10. A compound of formula (I) according to claim 1, in which:

R$_1$ is a hydrogen atom or a methyl;

R$_2$ is a methyl;

R$_3$ is a 2,4-dichlorophenyl;

R$_4$ is:

a 2-methyl-1,3-thiazol-4-yl, a 2-amino-1,3-thiazol-4-yl, a 2-(methylamino)-1,3-thiazol-4-yl, a 2-(hydroxymethyl)-1,3-thiazol-4-yl, a 2-(ethoxymethyl)-1,3-thiazol-4-yl, a 2-[[(2,2-dimethylpropanoyl)oxy]methyl]-1,3-thiazol-4-yl, or a 2-[(cyclopropylcarbonyl)oxy]methyl;

a 1,3-thiazol-2-yl, a 4-methyl-1,3-thiazol-2-yl, a 4-amino-1,3-thiazol-2-yl, a 4-(aminomethyl)-1,3-thiazol-2-yl, a 4-[(dimethylamino)methyl]-1,3-thiazol-2-yl, a 4-(pyrrolidin-1-ylmethyl)-1,3-thiazol-2-yl, a 4-(chloromethyl)-1,3-thiazol-2-yl, a 4-(2-methoxy-2-oxoethyl)-1,3-thiazol-2-yl, or a 4-(carboxymethyl)-1,3-thiazol-2-yl;

a 1,3-oxazol-4-yl, a 2-methyl-1,3-oxazol-4-yl, a 2-amino-1,3-oxazol-4-yl, a 2-(hydroxymethyl)-1,3-oxazol-4-yl, a 2-(ethoxymethyl)-1,3-oxazol-4-yl, or a 2-[[(2,2-dimethylpropanoyl)oxy]methyl]-1,3-oxazol-4-yl;

a 1,3-oxazol-5-yl, a 2-methyl-1,3-oxazol-5-yl, or a 2-(ethoxymethyl)-1,3-oxazol-5-yl;

a 1,3-oxazol-2-yl, a 4-methyl-1,3-oxazol-2-yl, or a 5-methyl-1,3-oxazol-2-yl;

an isoxazol-5-yl, a 4-methylisoxazol-5-yl, or a 3-(methoxycarbonyl)isoxazol-5-yl;

a 1H-pyrazol-5-yl, a 1-ethyl-1H-pyrazol-5-yl, a 3-(methoxycarbonyl)-1H-pyrazol-5-yl, a 3-methyl-1H-pyrazol-5-yl, or a 3-amino-1H-pyrazol-5-yl;

a 1-methyl-1H-pyrazol-3-yl, or a 1-ethyl-1H-pyrazol-3-yl;

a 3-amino-1H-pyrazol-4-yl;

a 5-amino-1,3,4-thiadiazol-2-yl; or a 1H-1,2,3-triazol-4-yl;

R$_5$ is a hydrogen atom;

or an acid addition salt thereof.

11. A compound of formula (I) according to claim 1, selected from the group consisting of:

6-(2-amino-1,3-thiazol-4-yl)-3-(2,4-dichlorophenyl)-1-methyl-1,9-dihydro-2H-pyrido[2,3-b]indol-2-one;

3-(2,4-dichlorophenyl)-6-[2-(hydroxymethyl)-1,3-thiazol-4-yl]-1-methyl-1,9-dihydro-2H-pyrido[2,3-b]indol-2-one;

3-(2,4-dichlorophenyl)-1,9-dimethyl-6-(2-methyl-1,3-thiazol-4-yl)-1,9-dihydro-2H-pyrido[2,3-b]indol-2-one;

[4-[3-(2,4-dichlorophenyl)-1,9-dimethyl-2-oxo-2,9-dihydro-1H-pyrido[2,3-b]indol-6-yl]-1,3-thiazol-2-yl]methyl pivalate;

3-(2,4-dichlorophenyl)-6-[2-(ethoxymethyl)-1,3-thiazol-4-yl]-1,9-dimethyl-1,9-dihydro-2H-pyrido[2,3-b]indol-2-one;

3-(2,4-dichlorophenyl)-1,9-dimethyl-6-(2-methyl-1,3-oxazol-4-yl)-1,9-dihydro-2H-pyrido[2,3-b]indol-2-one;

3-(2,4-dichlorophenyl)-1,9-dimethyl-6-(2-methyl-1,3-oxazol-5-yl)-1,9-dihydro-2H-pyrido[2,3-b]indol-2-one;

6-(3-amino-1H-pyrazol-5-yl)-3-(2,4-dichlorophenyl)-1,9-dimethyl-1,9-dihydro-2H-pyrido[2,3-b]indol-2-one;

6-[4-(aminomethyl)-1,3-thiazol-2-yl]-3-(2,4-dichlorophenyl)-1,9-dimethyl-1,9-dihydro-2H-pyrido[2,3-b]indol-2-one;

6-(3-amino-1H-pyrazol-4-yl)-3-(2,4-dichlorophenyl)-1,9-dimethyl-1,9-dihydro-2H-pyrido[2,3-b]indol-2-one; and 3-(2,4-dichlorophenyl)-1,9-dimethyl-6-(1H-pyrazol-5-yl)-1,9-dihydro-2H-pyrido[2,3-b]indol-2-one;

or an acid addition salt thereof.

12. A compound of formula (I) according to claim 1, selected from the group consisting of:

3-(2,4-dichlorophenyl)-6-(1-methoxymethyl-1H-pyrazol-3-yl)-1,9-dimethyl-1,9-dihydropyrido[2,3-b]indol-2-one;

3-(4-bromophenyl)-6-(1-ethyl-1H-pyrazol-3-yl)-1,9-dimethyl-1,9-dihydropyrido[2,3-b]indol-2-one;

6-(2-aminothiazol-5-yl)-3-(2-chloro-4-fluorophenyl)-1,9-dimethyl-1,9-dihydropyrido[2,3-b]indol-2-one;

3-(2,4-dichlorophenyl)-6-(2-methoxymethylthiazol-4-yl)-1,9-dimethyl-1,9-dihydropyrido[2,3-b]indol-2-one;

3-(2,4-dichlorophenyl)-6-[1-(2,2-dimethylpropionyl)-4-methyl-1H-pyrazol-3-yl]-1,9-dimethyl-1,9-dihydropyrido[2,3-b]indol-2-one;

3-(2,4-dichlorophenyl)-6-(5-ethoxymethyl-1-methyl-1H-pyrazol-3-yl)-1,9-dimethyl-1,9-dihydropyrido[2,3-b]indol-2-one;

3-(4-fluorophenyl)-6-(1-methoxymethyl-1H-pyrazol-3-yl)-1,9-dimethyl-1,9-dihydropyrido[2,3-b]indol-2-one;

3-(4-fluorophenyl)-6-(1-methoxymethyl-4-methyl-1H-pyrazol-3-yl)-1,9-dimethyl-1,9-dihydropyrido[2,3-b]indol-2-one;

3-(4-chlorophenyl)-6-(2-ethoxymethylthiazol-4-yl)-1,9-dimethyl-1,9-dihydropyrido[2,3-b]indol-2-one;

3-(2,4-dichlorophenyl)-6-[1-(2,2-dimethylpropionyl)-1H-pyrazol-3-yl]-1,9-dimethyl-1,9-dihydropyrido[2,3-b]indol-2-one; and 3-(2,4-dichlorophenyl)-6-(1-methoxymethyl-1H-[1,2,3]triazol-4-yl)-1,9-dimethyl-1,9-dihydropyrido[2,3-b]indol-2-one;

or an acid addition salt thereof.

13. A process for preparing a compound of formula (I) according to claim 1
in which:

$R_4 = $ [4-methyl-thiazol-2-yl with $R_7$]

said process comprising reacting a compound of formula:

(II)

[structure with Hal-CH$_2$-C(=O)- group, $R_3$, $R_5$, $R_1$, $R_2$, =O]

in which $R_1$, $R_2$, $R_3$ and $R_5$ are as defined for a compound of formula (I) in claim 1 and Hal is a halogen atom, with a compound of formula:

(III)

$$R_7-\overset{S}{\underset{\|}{C}}-NH_2$$

in which $R_7$ is as defined for a compound of formula (I) in claim 1.

14. A process for preparing a compound of formula (I) according to claim 1 in which:

$R_4 = $ [thiazol-4-yl with $R_7$, 2-methyl]

said process comprising reacting a compound of formula:

(IV)

[structure with H$_2$N-C(=S)- group, $R_3$, $R_5$, $R_1$, $R_2$, =O]

in which $R_1$, $R_2$, $R_3$ and $R_5$ are as defined for a compound of formula (I) in claim 1, with a compound of formula:

(V)

$$R_7-\overset{O}{\underset{\|}{C}}-CH_2-Hal$$

in which $R_7$ is as defined for a compound of formula (I) and Hal is a halogen atom.

15. A process for preparing a compound of formula (I) according to claim 1 in which:

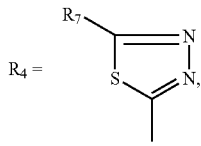

said process comprising reacting a compound of formula:

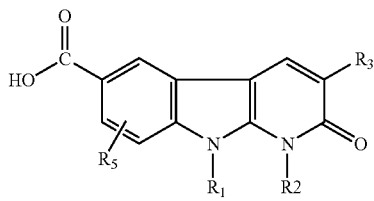

(VII)

in which $R_1$, $R_2$, $R_3$ and $R_5$ are as defined for a compound of formula (I) in claim 1,
with a compound of formula:

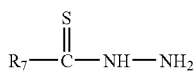

(VIII)

in which $R_7$ is as defined for a compound of formula (I) in claim 1.

16. A process for preparing a compound of formula (I) according to claim 1
in which:

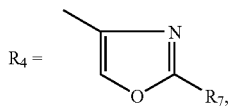

said process comprising reacting a compound of formula:

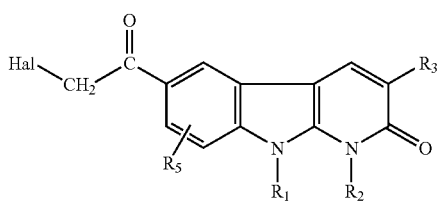

(II)

in which $R_1$, $R_2$, $R_3$ and $R_5$ are as defined for a compound of formula (I) in claim 1 and Hal is a halogen atom, with a compound of formula:

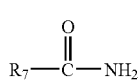

(IX)

in which $R_7$ is as defined for a compound of formula (I) in claim 1.

17. A process for preparing a compound of formula (I) according to claim 1
in which:

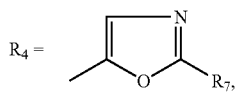

said process comprising the steps of:
A) reacting a compound of formula:

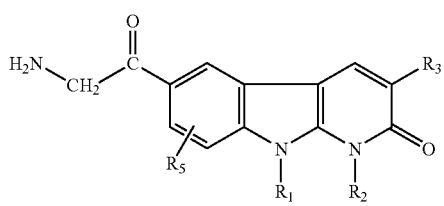

(X)

in which $R_1$, $R_2$, $R_3$ and $R_5$ are as defined for a compound of formula (I) in claim 1,
with a functional derivative of an acid of formula:

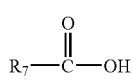

(XI)

in which $R_7$ is as defined for a compound formula (I) in claim 1, so as to obtain a compound of formula:

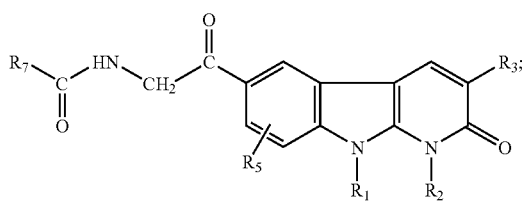

B) and cyclizing the compound of formula (XII) through the action of an acid.

18. A process for preparing a compound of formula (I) according to claim 1
in which:

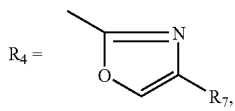

said process comprising reacting a compound of formula:

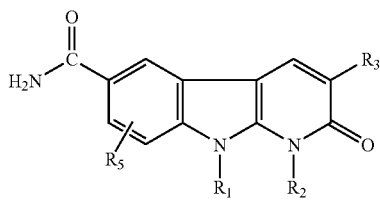

in which $R_1$, $R_2$, $R_3$ and $R_5$ are as defined for a compound of formula (I) in claim 1,
with a compound of formula:

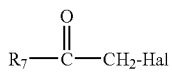

in which $R_7$ is as defined for a compound of formula (I) in claim 1 and Hal is a halogen atom.

19. A process for preparing a compound of formula (I) according to claim 1
in which:

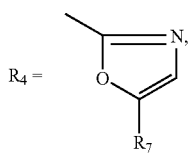

said process comprising reacting a compound of formula:

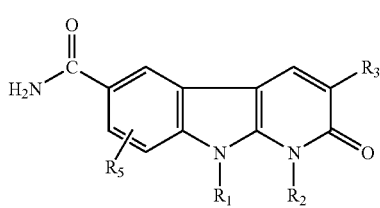

in which $R_1$, $R_2$, $R_3$ and $R_5$ are as defined for a compound of formula (I), with a compound of formula:

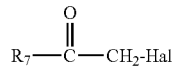

in which $R_7$ is as defined for a compound of formula (I) and Hal is a halogen atom.

20. A process for preparing a compound of formula (I) according to claim 1
in which:

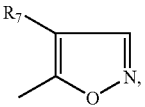

said process comprising reacting a compound of formula:

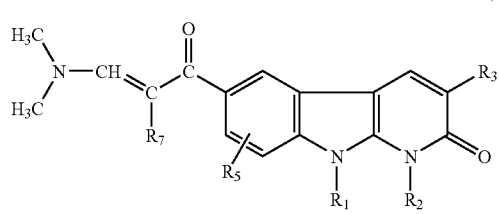

in which $R_1$, $R_2$, $R_3$, $R_5$ and $R_7$ are as defined for a compound of formula (I) in claim 1,
with hydroxylamine.

21. A process for preparing a compound of formula (I) according to claim 1 in which

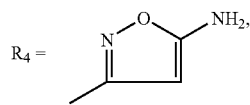

said process comprising reacting a compound of formula (XX):

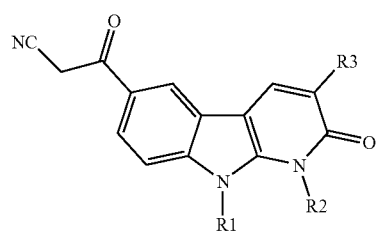

in which $R_1$, $R_2$ and $R_3$ are as defined for a compound of formula (I) in claim 1, with hydroxylamine.

22. A process for preparing a compound of formula (I) according to claim 1
in which:

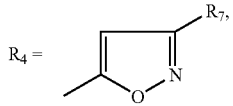

said process comprising reacting a compound of formula:

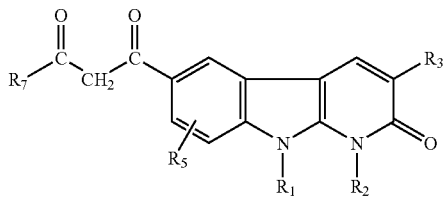

(XVIII)

in which $R_1$, $R_2$, $R_3$, $R_5$ and $R_7$ are as defined for a compound of formula (I) in claim 1,
with hydroxylamine.

23. A process for preparing a compound of formula (I) according to claim 1
in which:

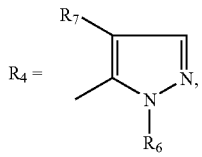

said process comprising reacting a compound of formula:

(XVII)

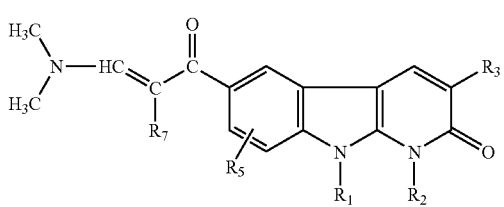

in which $R_1$, $R_2$, $R_3$, $R_5$ and $R_7$ are as defined for a compound of formula (I) in claim 1,
with a compound of formula:

NH$_2$—NH—R$_6$      (XIX)

in which $R_6$ is as defined for a compound of formula (I) in claim 1.

24. A process for preparing a compound of formula (I) according to claim 1
in which:

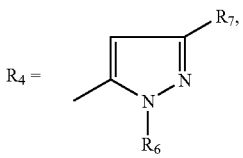

said process comprising reacting a compound of formula:

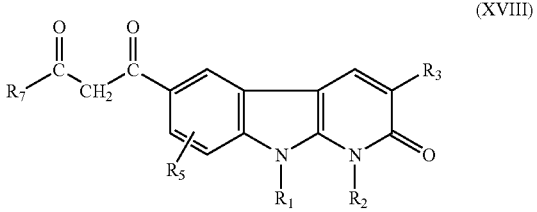

(XVIII)

in which $R_1$, $R_2$, $R_3$, $R_5$ and $R_7$ are as defined for a compound of formula (I) in claim 1,
with a hydrazine of formula:

NH—NH—R$_6$      (XIX)

25. A process for preparing a compound of formula (I) according to claim 1
in which:

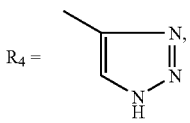

said process comprising reacting a compound of formula (XXII):

(XXII)

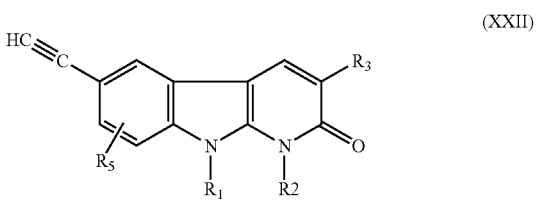

in which $R_1$, $R_2$, $R_3$ and $R_5$ are as defined for a compound of formula (I) in claim 1,
with sodium azide.

26. A pharmaceutical composition comprising a compound of formula (I) according to claim 1, or a pharmaceutically acceptable salt of the compound, and at least one pharmaceutically acceptable excipient.

27. A method of treating breast cancer; said method comprising administering to a patient in need thereof a therapeutically effective amount of a compound according to claim 1, or a pharmaceutically acceptable salt of the compound.

* * * * *